United States Patent [19]
Koezuka et al.

[11] Patent Number: 5,767,092
[45] Date of Patent: Jun. 16, 1998

[54] TREATMENT OF RADIATION-DAMAGED BONE MARROW USING GALACTOSYL CERAMIDES

[75] Inventors: Yasuhiko Koezuka; Koji Kabaya; Kazuhiro Motoki, all of Takasaki, Japan

[73] Assignee: Kirin Beer Kabushiki Kaisha, Tokyo-to, Japan

[21] Appl. No.: 406,061

[22] Filed: Mar. 17, 1995

Related U.S. Application Data

[63] Continuation of Ser. No. 91,979, Jul. 15, 1993, abandoned.

[30] Foreign Application Priority Data

Jul. 16, 1992 [JP] Japan ................................. 4-212015
Mar. 19, 1993 [JP] Japan ................................. 5-85219

[51] Int. Cl.$^6$ ........................................................ A61K 31/70
[52] U.S. Cl. ........................................ 514/25; 536/17.9
[58] Field of Search ................................. 536/17.9; 514/25

[56] References Cited

U.S. PATENT DOCUMENTS

| | | | |
|---|---|---|---|
| 4,952,683 | 8/1990 | Tschannen | 536/18.6 |
| 5,073,543 | 12/1991 | Marshall | 514/21 |

FOREIGN PATENT DOCUMENTS

| | | |
|---|---|---|
| 1093562 | 4/1989 | Japan . |
| 05009193 | 1/1993 | Japan . |
| 9305055 | 3/1993 | WIPO . |

OTHER PUBLICATIONS

Honda, M. et al. "Syntheses of a New ..." Chem. Pharm. Bull. vol. 39 (8) 1385–1391 (1991).
Isobe, R. et al. Biomedical and Environmental Mass Spectrometry vol. 13, 585–594 (1986).
Tsunematsu, H. et al. Biochemical and Biophysical Research Communications vol. 146 No. 2, 907–911, (1987).
Komori, T. et al. Mass Spectrometry Reviews 1985, 4, 255–293.
Kalechman, Y. et al. The Journal of Immunology vol. 145, 1512–1517, Sep. 1, 1990.
Hall, E.J. Radiobiology for the Radiologist 1978 pp. 3–12, 173–175, 205–215.
Tanikawa, S. et al. Blood vol. 76 No. 3 Aug. 1, 1990 pp. 445–449.
Okano, A. et al. Transplantation vol. 47 No. 4 pp. 738–740 (Apr. 1989).
Tamura, M. et al. Transplantation vol. 51 No. 6, pp. 1166–1170 (Jun. 1991).
Atkinson, K. et al. Blood vol. 77 No. 6 Mar. 15, 1991 pp. 1376–1382.
Kodo, H. et al. The Lancet Jul. 2, 1988 pp. 38–39.
Blazer, B. et al. Blood vol. 74 No. 6 Nov. 1, 1989 pp. 2264–2269.
Sheridan, W.P. et al. The Lancet, Oct. 14, 1989, pp. 891–895.
Brandt, S.J. The New England Journal of Medicine, vol. 318, Apr. 7, 1988 pp. 869–876.
Teshima, H. Exp. Hematol. vol. 17 1989 pp. 853–858.
Souza, L.M. et al. Science vol. 232 pp. 61–65 (Apr. 1986).
Nienhuis, A.W. The Journal of Clinical Investigation vol. 8, Aug. 1987, 573–577.
Monroy, R.L. Blood vol. 70 No. 5 Nov. 1987 pp. 1696–1699.
Shiio, T. Jpn J. Cancer Chemother. 15(3) Mar. 1988 pp. 481–485.
Taguchi, T. Jpn. J. Cancer Chemother. 12(2) Feb. 1985 pp. 366–378.

*Primary Examiner*—Kathleen K. Fonda
*Attorney, Agent, or Firm*—Ladas & Parry

[57] ABSTRACT

The present invention relates to a pharmaceutical composition (a marrow cell proliferation accelerator, a radioprotective agent, a therapeutic agent for thrombocytopenia) comprising a compound represented by the following formula (A), and to a therapeutic or prophylactic method (a method for accelerating marrow cell proliferation, a method for protecting human against radiation damage, a method for the treatment of thrombocytopenia) characterized in that an effective amount of a compound represented by the following formula (A) is administered to human:

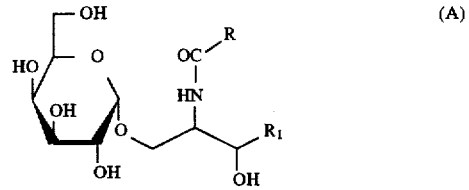

(A)

wherein $R_2$ represents

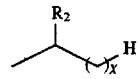

26) or —$(CH_2)_7CH=CH(CH_2)_7CH_3$, and $R_1$, is one of the substituents defined by the following (a) to (d):

(a) —$CH_2(CH_2)_yCH_3$, (b) —$CH(OH)(CH_2)_y(CH_3)_2$, and (c) —$CH(OH)(CH_2)_yCH(CH_3)_2$, and (d) —$CH=CH(CH_2)_yCH_3$
(wherein Y is an integer of 5–17).

22 Claims, 16 Drawing Sheets

SYNTHETIC ROUTE A

SYNTHESIS OF COMPOUND 9

SYNTHESIS OF COMPOUND 7

SYNTHESIS OF COMPOUND 5

SYNTHESIS OF COMPOUND 1

SYNTHESIS OF COMPOUND 5

SYNTHESIS OF COMPOUND 22

TREATMENT OF RADIATION-DAMAGED BONE MARROW USING GALACTOSYL CERAMIDES

This is a continuation of application Ser. No. 08/091,979 filed on Jul. 15, 1993, now abandoned.

BACKGROUND OF THE INVENTION

1. Field of the Invention

The present invention relates to a medicine comprising as an active ingredient a specific α-galactosylceramide, and a therapeutic method. More specifically, the present invention relates to a marrow cell proliferation accelerator having potent therapeutic effects on various diseases caused by the damage to marrow cells; a radiation damage protector which has a life-span-increasing effect on those who have been exposed to a lethal dose of radiation, and which is effective for prophylaxis and remedy of side effects caused upon radiotherapy; and a therapeutic agent for thrombocytopenia, capable of increasing the number of blood platelets or inhibiting a reduction in the number of blood platelets. Further, the present invention relates to a method of marrow cell proliferation, a method for protecting a human against radiation damage, and a method for the treatment of thrombocytopenia, comprising administering an effective amount of a specific α-galactosylceramide to a human.

2. Related Art

It is known that marrow cells are damaged and their number is decreased by irradiation with a large dose of radiation, or by administration of a large amount of chemotherapeutic agent.

Further, it is known that hypoplastic anemia, osteomyelodysplasia and the like are diseases caused by a functional disorder (including a decrease in the number) or hypofunction of marrow cells. The marrow cells herein refer to those cells which are present in bone marrow, and include red blood cells, neutrophiles, eosinophils, basophils, monocytes, lymphocytes, and various cells, such as blood platelets, in various differentiated stages.

In order to overcome the damage to marrow cells, which is a cause of the above-described conditions of diseases or diseases, bone marrow transplantation or administration of various hematopoietic factors has been attempted, and, in addition, the exploration of novel marrow-cell-proliferating factors is now being made energetically.

As mentioned above, various diseases or conditions of diseases are caused by the damage to marrow cells. Since a decrease in the number of marrow cells is one of the causes of the diseases, there is a high possibility that a marrow-cell-proliferation-accelerating material can ameliorate the above diseases or conditions of diseases.

rays, β-rays and γ-rays emitted from a radioactive substance, or radiations such as artificially produced potent X-rays, proton rays, neutron rays and electron beams, are indispensable for the treatment or diagnosis of diseases such as cancer. However, when more than a permissible dose of radiation is used, or when normal tissues or organs in the body are irradiated during treatment, the numbers of white blood cells, red blood cells and the like are decreased as a side effect of radiation. Therefore, radiotherapy cannot always be conducted completely.

Moreover, irradiation with ultraviolet rays, which is a kind of radiation, also causes various diseases.

Various methods which can prevent such radiation damages and side effects thereof have been studied.

For instance, in a chemical protection method using a medicine, a material capable of revivifying the immunological function of immunocytes which have been inhibited by radiation, for example, cepharanthine or Sonifilan; or an agent for activating respiration of cell tissues, for example, cytochrome C, Solcoselin or adenine have been used. In the present situation that the above materials show only a slight effect on preventing the side effects caused by irradiation with radiation.

Further, with respect to radiation damage, a radiation protector containing a processed material of Streptococcus lactis which can eliminate free radicals or active oxygen produced by the ionizing effect of radiation has been proposed (Japanese Laid-Open Patent Publication No. 103023/1987). However, this agent cannot be expected to have excellent effects such as a life-span-increasing effect on those who are exposed to a lethal dose of radiation.

A method in which a material having a macrobiotic effect on those who are exposed to a lethal dose of radiation has been proposed recently. For instance, a method using 2-phenyl-1,2-benzoisoserenazol-3(2H)-on (Japanese Laid-Open Patent Publication No. 135718/1989), a method using a Cimetidine-copper complex (Japanese Laid-Open Patent Publication No. 153640/1989), and a method using a nonapeptide which is known as a serum thymic factor (Japanese Laid-Open Patent Publication No. 36126/1990) have been proposed. However, there are continuous demands for more excellent radioprotective agents.

Blood platelets are a blood cell component which play an important role in the mechanism of hemostasis of the organism. Specific symptoms of thrombocytopenia are hemorrhage and abnormal blood coagulation.

Hereditary thrombocytopenia, idiopathic thrombocytopenic purpura, hypoplastic anemia and the like have been known as thrombocytopenia in which the number of blood platelets decreases. However, a clinical problem in recent years is thrombocytopenia caused as a side effect of a chemotherapeutic agent or radiotherapy used for the treatment of cancer.

All of the chemotherapeutic agents currently used have a potent bone-marrow-suppressive effect, so that administration of such an agent induces a remarkable decrease in the number of white blood cells or blood platelets. There are therefore many cases where the treatment has to be suspended because of this side effect. X-rays or γ-rays, which are used in radiotherapy, also adversely act on hemopoietic tissues such as bone marrow and bring about a drastic decrease in the number of white blood cells or blood platelets as in the case where the chemotherapeutic agent is administered. For this reason, irradiation with radiation is often forced to be discontinued.

Platelet transfusion and bone marrow transplantation are known as therapeutic methods which are often used presently for the treatment of thrombocytopenia caused by the above-described chemotherapy or radiotherapy for cancer.

However, in the case of the above platelet transfusion, it is necessary to conduct transfusion frequently because the life span of white blood cells or blood platelets is short. In addition, the transfusion is attended with the danger of infection by cytomegalovirus or the like. Further, in the case of bone marrow transplantation, it is difficult to find a donor of bone marrow which is compatible with the bone marrow of a patient. Moreover, even after the transplantation of bone marrow, several months are required for the number of blood platelets to be normal.

Under such circumstances, muramyldipeptide derivatives (Laid-Open Publication No. WO 89/01778), humanmacrophage-colony-stimulating factors (Japanese Laid-Open Patent Publication No. 207244/1989), interleukin-1 and derivatives thereof (Japanese Laid-Open Patent Publication No. 138224/1990), human BCDF (Japanese Laid-Open Patent Publication No. 101624/1991) and the like are now being developed as therapeutic agents for the above-described thrombocytopenia. However, none of the above agents can sufficiently fulfill the demands.

Therefore, more efficacious therapeutic agents for thrombocytopenia are demanded presently.

SUMMARY OF THE INVENTION

As mentioned above, a medicine, or a therapeutic or prophylactic method effective for the treatment or prophylaxis of the damage to marrow cells, radiation damage and thrombocytopenia has been demanded.

An object of the present invention is to provide a marrow-cell-proliferation-accelerating agent or method which is highly effective for ameliorating various diseases or conditions of diseases caused by the damage to marrow cells.

Another object of the present invention is to develop a radioprotective agent which is extremely effective for the organism, thereby providing an agent or a method for protecting a human against radiation damage which can minimize the influence of irradiation with radiation to the organism, and which shows a high life-span-increasing effect on those who are exposed to a lethal dose of radiation.

A further object of the present invention is to develop, in consideration of the aforementioned present situation, a novel therapeutic agent for thrombocytopenia, thereby providing a therapeutic agent effective for various types of thrombocytopenia, and also providing a medicine or a method capable of mitigating a decrease of blood platelets which is a limiting factor upon chemotherapy and radiotherapy for cancer.

Specific α-galactosylceramides were applied to cultured cells and animals, and their influences were studied. As a result, the following points were found: (1) the compounds have a marrow-cell-proliferation-accelerating effect, (2) they can be an effective protective means against irradiation with radiation, (3) they are excellent in a blood-platelet-increasing effect and a blood-platelet-decrease-inhibitory effect, and, in addition, they are quite safe even when administered to the organism. The present invention has been accomplished on the basis of the above findings.

The pharmaceutical composition (a marrow cell proliferation accelerator, a radioprotective agent and a therapeutic agent for thrombocytopenia) according to the present invention comprises one or more α-galactosylceramides represented by the following formula (A) as active ingredients together with a carrier or a diluent:

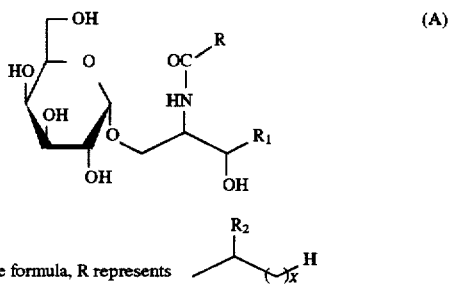

In the formula, R represents 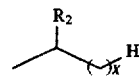

(wherein $R_2$ represents H or OH, X is an integer of 0–26) or $—(CH_2)_7CH=CH(CH_2)_7CH_3$, and $R_1$ is one of the substituents defined by the following (a) to (d): (a) $—CH_2(CH_2)_yCH_3$, (b) $—CH(OH)(CH_2)_yCH_3$, (c) $—CH(OH)(CH_2)_yCH(CH_3)_2$, and (d) $—CH=CH(CH_2)_yCH_3$ (wherein Y is an integer of 5–17).

In the above formula (A), (1) when R is

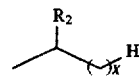

the compound is represented by the following formula (I), and (2) when R is $—(CH_2)_7CH=CH(CH_2)_7CH_3$, the compound is represented by the following formula (XXI):

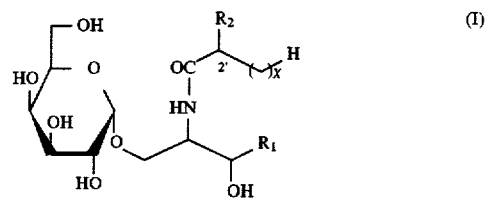

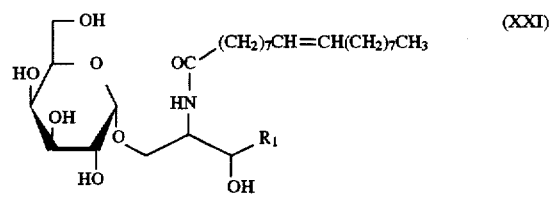

In the method according to the present invention, the method for proliferating marrow cell is characterized by administering an effective amount of the compound represented by the above formula (A) (formula (I) or (XXI)) to a patient who needs marrow cell proliferation; the method for protecting human against radiation damage is characterized by administering an effective amount of the compound represented by the above formula (A) (formula (I) or (XXI)) to a human who needs protection against radiation damage; and the method for the treatment of thrombocytopenia is characterized by administering an effective amount of the compound represented by the above formula (A) (formula (I) or (XXI)) to a patient who needs inhibition of a reduction in number of blood platelets or an increase in the number of blood platelets.

DETAILED DESCRIPTION OF THE INVENTION COMPOUNDS REPRESENTED BY FORMULA (A)

Figure 1:
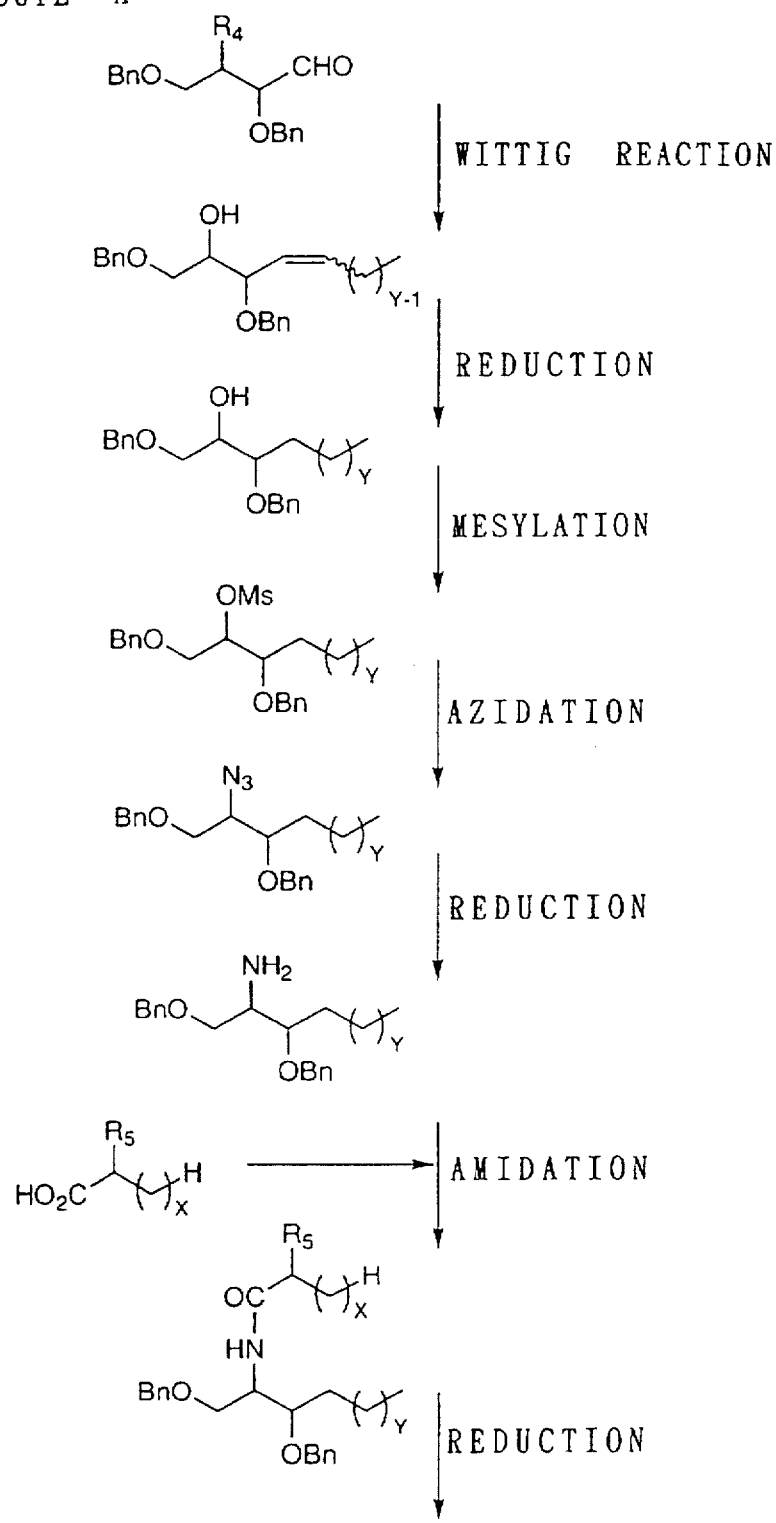
FIG. 1 (a and b) is a diagram showing a reaction route (synthesis route A) for synthesizing a compound represented by the formula (A), using as a starting material an aldehyde compound.
Figure 1:
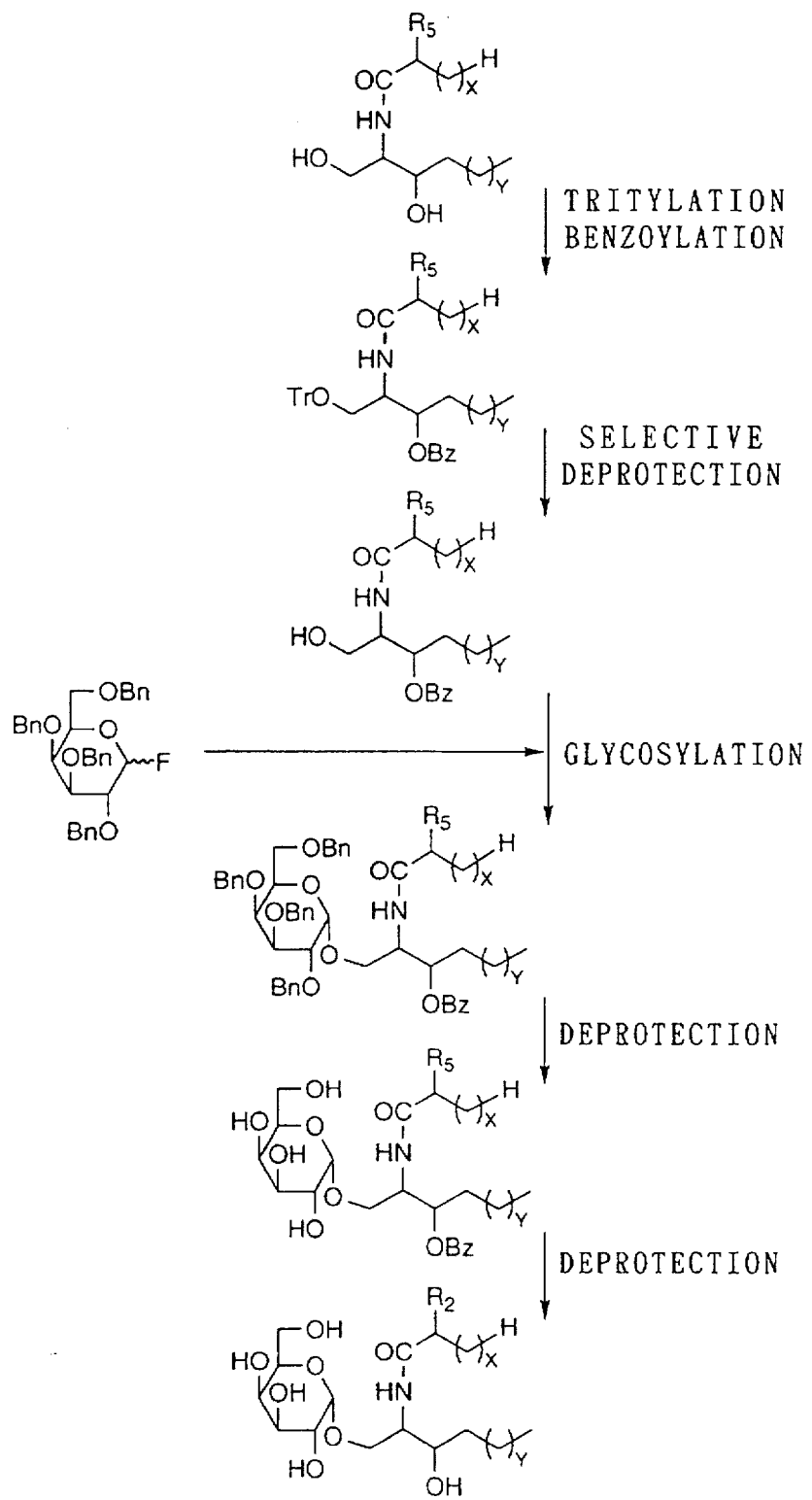

As mentioned previously, a compound used for the medicine and the therapeutic (or prophylactic) method according to the present invention is one having a chemical structure represented by the formula (A) (i.e. the formulas (I) and (XXI)). It is preferable that $R_1$ in the formula (I) be one of the following (a) to (d):

(a) —$CH_2(CH_2)_xCH_3$

In the above, when $R_2$ is H, it is preferable that X be an integer of 0 to 24 and Y be an integer of 7 to 15; and when $R_2$ is OH, it is preferable that X be an integer of 20 to 24 and Y be an integer of 11 to 15. Further, when $R_2$ is H, it is particularly preferable that X be an integer of 8 to 22 and Y be an integer of 9 to 13; and when $R_2$ is OH, it is particularly preferable that X be an integer of 21 to 23 and Y be an integer of 12 to 14. (b) —$CH(OH)(CH_2)YCH_3$ In the above, when $R_2$ is H, it is preferable that X be an integer of 18 to 26 and Y be an integer of 5 to 15; and when $R_2$ is OH, it is preferable that X be an integer of 18 to 26 and Y be an integer of 5 to 17. Further, when $R_2$ is H, it is particularly preferable that X be an integer of 21 to 25 and Y be an integer of 6 to 14; and when $R_2$ is OH, it is particularly preferable that X be an integer of 21 to 25 and Y be an integer of 6 to 16. (c) —$CH(OH)(CH_2)YCH(CH_3)_2$ In the above, when $R_2$ is H, it is preferable that X be an integer of 20 to 24 and Y be an integer of 9 to 13; and when $R_2$ is OH, it is preferable that X be an integer of 20 to 24 and Y be an integer of 9 to 13. Further, when $R_2$ is H, it is particularly preferable that X be an integer of 21 to 23 and Y be an integer of 10 to 12; and when $R_2$ is OH, it is particularly preferable that X be an integer of 21 to 23 and Y be an integer of 10 to 12. (d) —$CH=CH(CH_2)YCH_3$ In the above, it is preferable that $R_2$ be H, X be an integer of 10 to 18, and Y be an integer of 10 to 14. Further, it is particularly preferable that X be an integer of 11 to 17 and Y be an integer of 11 to 13.

On the other hand, it is preferable that $R_1$ in the formula (XXI) be —$CH_2(CH_2)_xCH_3$. In this formula, Y is preferably an integer of 11 to 15, and an integer of 12 to 14 is particularly preferred.

Further, among the compounds of the present invention, those compounds which are of 2- or 3-coordination as represented by the formula (II) that will be shown later are particularly preferred.

More specific and preferred embodiments of the compounds represented by the formula (A) (the formulas (I) and (XXI)) can be explained by the following definitions (1) to (35). (1) α-Galactosylceramides of the formula (I), represented by the following formula (II):

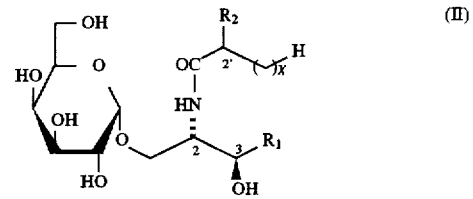

In the formula, $R_1$ is one of the substituents defined by the following (a) to (e), and $R_2$ represents H or OH (X is defined in the following (a) to (e)). (a) —$CH_2(CH_2)yCH_3$ When $R_2$ is H, X is an integer of 0 to 24 and Y is an integer of 7 to 15; and when $R_2$ is OH, X is an integer of to 24 and Y is an integer of 11 to 15. (b) —$CH(OH)(CH_2)YCH_3$ When $R_2$ is H, X is an integer of 18 to 26 and Y is an integer of 5 to 15; and when $R_2$ is OH, X is an integer of 18 to 26 and Y is an integer of 5 to 17. (c) —$CH(OH)(CH_2)YCH(CH_3)_2$ When $R_2$ is H, X is an integer of 20 to 24 and Y is an integer of 9 to 13; and when $R_2$ is OH, X is an integer of 20 to 24 and Y is an integer of 9 to 13. (d) —$CH=CH—(CH_2)yCH_3$ $R_2$ is H, X is an integer of 10 to 18, and Y is an integer of 0 to 14. (2) α-Galactosylceramides of the formula (I), represented by the following formula (III):

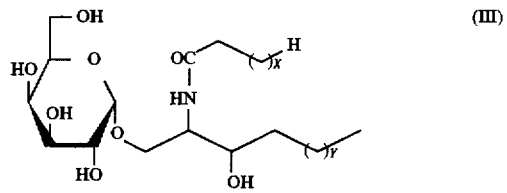

(In the formula, X is an integer of 0 to 24, and Y is an integer of 7 to 15.) (3) More preferably, α-galactosylceramides described in the above (2), wherein X is an integer of 8 to 22 and Y is an integer of 9 to 13. (4) Still more preferably, α-galactosylceramides described in the above (2), represented by the following formula (IV):

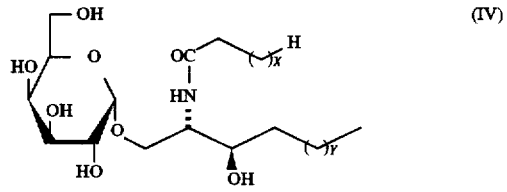

In the formula, X represents an integer of 0 to 24, and Y represents an integer of 7 to 15. (5) Most preferably, α-galactosylceramides described in the above (4), wherein X is an integer of 8 to 22 and Y is an integer of 9 to 13. (6) α-Galactosylceramides of the formula (I), represented by the following formula (V):

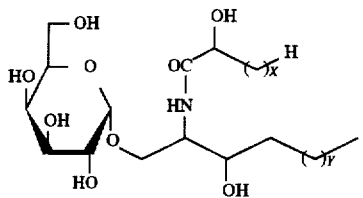

(V)

In the formula, X is an integer of 20 to 24, and Y is an integer of 11 to 15. (7) More preferably, α-galactosylceramides described in the above (6), wherein X is an integer of 21 to 23 and Y is an integer of 12 to 14. (8) Still more preferably, α-galactosylceramides described in the above (6), represented by the following formula (VI):

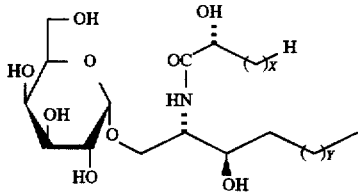

(VI)

In the formula, X is an integer of 20 to 24 and Y is an integer of 11 to 15. (9) Most preferably, α-galactosylceramides described in the above (8), wherein X is an integer of 21 to 23 and Y is an integer of 12 to 14. (10) α-Galactosylceramides of the formula (I), represented by the following formula (VII):

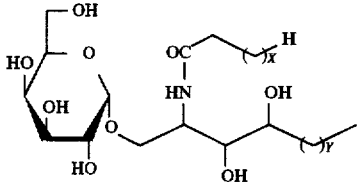

(VII)

In the formula, X is an integer of 18 to 26 and Y is an integer of 5 to 15. (11) More preferably, α-galactosylceramides described in the above (10), wherein X is an integer of 21 to 25 and Y is an integer of 6 to 14. (12) Still more preferably, α-galactosylceramides described in the above (10), represented by the following formula (VIII):

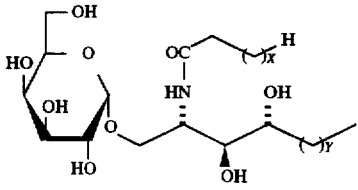

(VIII)

In the formula, X is an integer of 18 to 26 and Y is an integer of 5 to 15. (13) Most preferably, α-galactosylceramides described in the above (12), wherein X is an integer of 21 to 25 and Y is an integer of 6 to 14. (14) α-Galactosylceramides of the formula (I), i represented by the following formula (IX):

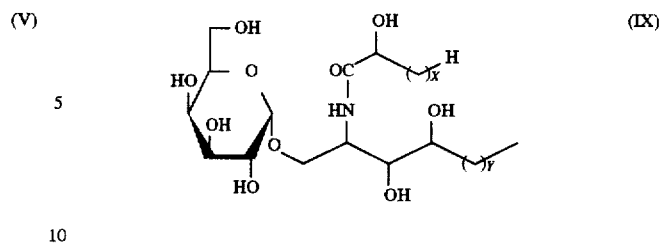

(IX)

In the formula, X is an integer of 18 to 26 and Y is an integer of 5 to 17. (15) More preferably, α-galactosylceramides described in the above (14), wherein X is an integer of 21 to 25 and Y is an integer of 6 to 16. (16) Still more preferably, α-galactosylceramides described in the above (14), represented by the following formula (X):

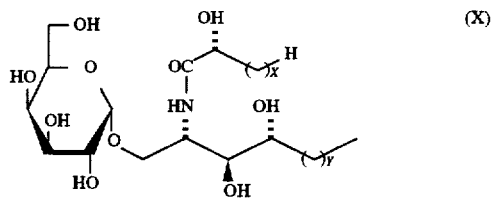

(X)

In the formula, X is an integer of 18 to 26 and Y is an integer of 5 to 17. (17) More preferably, α-galactosylceramides described in the above (14), represented by the following formula (X'):

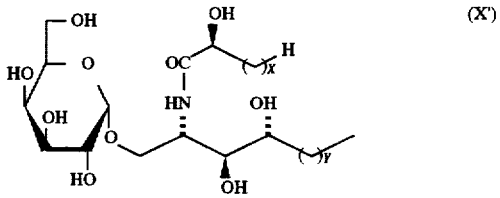

(X')

In the formula, X is an integer of 20 to 24 and Y is an integer of 10 to 14. (18) Most preferably, α-galactosylceramides described in the above (16), wherein X is an integer of 21 to 25 and Y is an integer of 6 to 16. (19) Most preferably, α-galactosylceramides described in the above (17), wherein X is an integer of 21 to 23 and Y is an integer of 11 to 13. (20) α-Galactosylceramides of the formula (I), represented by the following formula (XI):

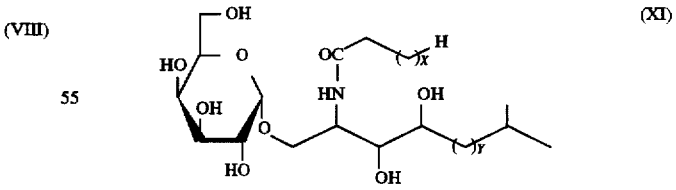

(XI)

In the formula, X is an integer of 20 to 24 and Y is an integer of 9 to 13. (21) More preferably, α-galactosylceramides described in the above (20), wherein X is an integer of 21 to 23 and Y is an integer of 10 to 12. (22) Still more preferably, α-galactosylceramides described in the above (20), represented by the following formula (XII):

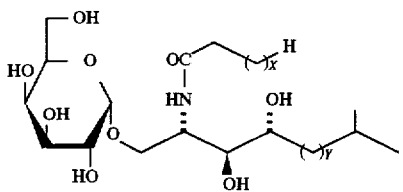
(XII)

In the formula X is an integer of 20 to 24 and Y is an integer of 9 to 13. (23) Most preferably, α-galactosylceramides described in the above (22), wherein X is an integer of 21 to 23 and Y is an integer of 10 to 12. (24) α-Galactosylceramides of the formula (I), represented by the following formula (XIII):

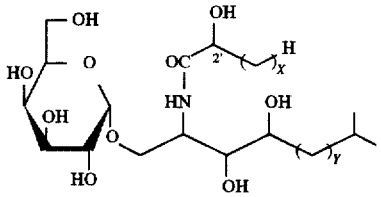
(XIII)

In the formula, X is an integer of 20 to 24 and Y is an integer of 9 to 13. (25) More preferably, -galactosylceramides described in the above (24), wherein X is an integer of 21 to 23 and Y is an integer of 10 to 12. (26) Still more preferably, α-galactosylceramides described in the above (24), represented by the following formula (XIV'):

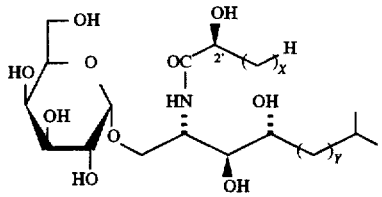
(XIV')

In the formula, X is an integer of 20 to 24 and Y is an integer of 9 to 13. (27) Most preferably, α-galactosylceramides described in 30 the above (26), wherein X is an integer of 21 to 23 and Y is an integer of 10 to 12. (28) α-Galactosylceramides of the formula (I), represented by the following formula (XV):

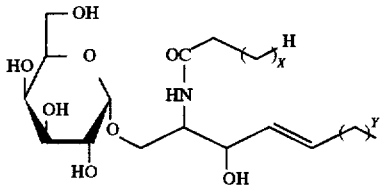
(XV)

In the formula, X is an integer of 10 to 18 and Y is an integer of 10 to 14. (29) More preferably, α-galactosylceramides described in the above (28), wherein X is an integer of 11 to 17 and Y is an integer of 11 to 13. (30) Still more preferably, α-galactosylceramides described in the above (28), represented by the following formula (XVI):

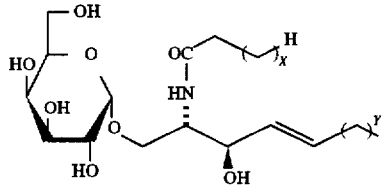
(XVI)

In the formula, X is an integer of 10 to 18 and Y is an integer of 10 to 14. (31) Most preferably, α-galactosylceramides described in the above (30), wherein X is an integer of 11 to 17 and Y is an integer of 11 to 13. (32) α-Galactosylceramides of the formula (XXI), represented by the following formula (XIX):

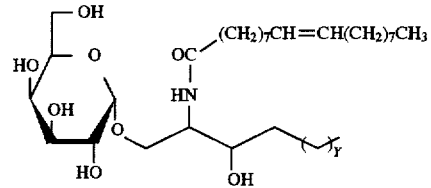
(XIX)

In the formula, Y is an integer of 11 to 15. (33) Preferably, α-galactosylceramides described in the above (32), wherein Y is an integer of 12 to 14. (34) More preferably, α-galactosylceramides described in the above (32), represented by the following formula (XX):

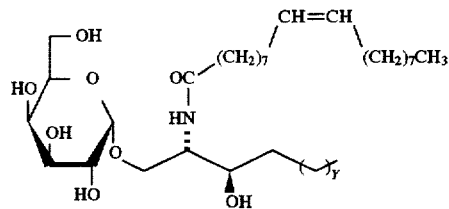
(XX)

In the formula, Y is an integer of 11 to 15. (35) Most preferably, α-galactosylceramides described in the above (34), wherein Y is an integer of 12 to 14.

Preferred, specific examples of the compounds represented by the formula (A) (the formulas (I) and (XXI)) are as follows. In each formula, X and Y are the same as before. (1) Compounds represented by the following formula (III) or (VI):

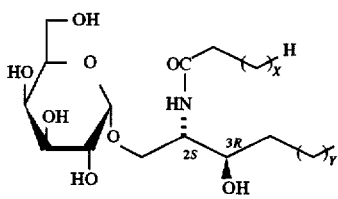
(IV)

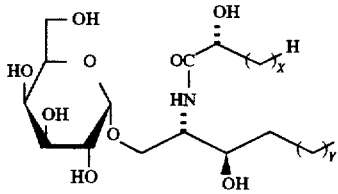
(VI)

Compound 1: (2S,3R)-1-(α-D-galactopyranosyloxy)-2-tetracosanoylamino-3-octadecanol, Compound 2: (2S,3R)-2-docosanoylamino-1-(α-D-galactopyranosyloxy)-3-octadecanol, Compound 3: (2S,3R)-1-(α-D-galactopyranosyloxy)-2-icosanoylamino-3-octadecanol.

Compound 4: (2S,3R)-1-(α-D-galactopyranosyloxy)-2-octadecanoylamino-3-octadecanol.

Compound 5: (2S,3R)-1-(α-D-galactopyranosyloxy)-2-tetradecanoylamino-3-octadecanol.

Compound 6: (2S,3R)-2-decanoylamino-1-(α-D-galactopyranosyloxy)-3-octadecanol.

Compound 7: (2S,3R)-1-(α-D-galactopyranosyloxy)-2-octanoylamino-3-octadecanol.

Compound 8: (2S,3R)-2-acetamino-1-(α-D-galactopyranosyloxy)-3-octadecanol.

Compound 9: (2S,3R)-1-(α-D-galactopyranosyloxy)-2-tetracosanoylamino-3-tetradecanol.

Compound 10: (2S,3R)-1-(α-D-galactopyranosyloxy)-2-tetradecanoylamino-3-hexadecanol.

Compound 11: (2R,3S)-1-(α-D-galactopyranosyloxy)-2-tetradecanoyiamino-3-hexadecanol.

Compound 12: (2S,3S)-1-(α-D-galactopyranosyloxy)-2-tetradecanoylamino-3-hexadecanol.

Compound 13: (2R,3R)-1-(α-D-galactopyranosyloxy)-2-tetradecanoylamino-3-hexadecanol, and Compound 14: (2S,3R)-1-(α-D-galactopyranosyloxy)-2-[(R)-2-hydroxytetracosanoylamino]-3-octadecanol.

Of these compounds, Compounds 1–10 and 14 are preferred because they are of 2- or 3-coordination. (2) Compounds represented by the following formula (XVI):

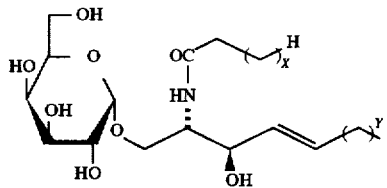

Compound 15: (2S,3R,4E)-1-(α-D-galactopyranosyloxy)-2-octadecanoylamino-4-octadecen-3-ol, and Compound 32: (2S,3R,4E)-1-(α-D-galactopyranosyloxy)-2-tetradecanoylamino-4-octadecen-3-ol.

(3) Compounds represented by the following formula (VIII):

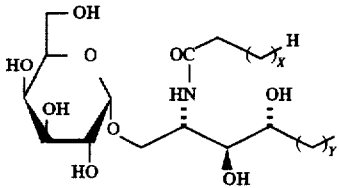

Compound 16: (2S,3S,4R)-1-(α-D-galactopyranosyloxy)-2-tetracosanoylamino-3,4-octadecanediol.

Compound 17: (2S,3S,4R)-1-(α-D-galactopyranosyloxy)-2-tetracosanoylamino-3,4-heptadecanediol.

Compound 18: (2S,3S,4R)-1-(α-D-galactopyranosyloxy)-2-tetracosanoylamino-3,4-pentadecanediol.

Compound 19: (2S,3S,4R)-1-(α-D-galactopyranosyloxy)-2-tetracosanoylamino-3,4-undecanediol.

Compound 20: (2S,3S,4R)-1-(α-D-galactopyranosyloxy)-2-hexacosanoylamino-3,4-heptadecanediol.

Compound 33: (2S,3S,4R)-1-(α-D-galactopyranosyloxy)-2-hexacosanoylamino-3,4-octadecanediol, and Compound 34: (2S,3S,4R)-1-(α-D-galactopyranosyloxy)-2-octacosanoylamino-3,4-heptadecanediol.

(4) Compounds represented by the following formula (X) or (X'):

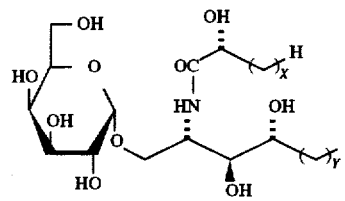

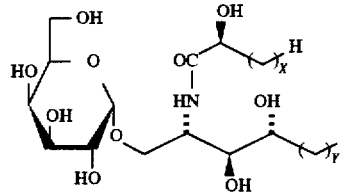

Compound 21: (2S,3S,4R)-1-(α-D-galactopyranosyloxy)-2-[(R)-2-hydroxytetracosanoylamino]-3,4-octadecanediol.

Compound 22: (2S,3S,4R)-1-(α-D-galactopyranosyloxy)-2-[(R)-2-hydroxytetracosanoylamino]-3,4-heptadecanediol.

Compound 23: (2S,3S,4R)-1-(α-D-galactopyranosyloxy)-2-[(R)-2-hydroxytetracosanoylamino]-3,4-pentadecanediol.

Compound 24: (2S,3S,4R)-1-(α-D-galactopyranosyloxy)-2-[(R)-2-hydroxytetracosanoylamino]-3,4-undecanediol.

Compound 25: (2S,3S,4R)-1-(α-D-galactopyranosyloxy)-2-[(R)-2-hydroxytetracosanoylamino]-3,4-octadecanediol.

Compound 26: (2S,3S,4R)-1-(α-D-galactopyranosyloxy)-2-[(R)-2-hydroxyhexacosanoylamino]-3,4-nonadecanediol.

Compound 27: (2S,3S,4R)-1-(α-D-galactopyranosyloxy)-2-[(R)-2-hydroxyhexacosanoylamino]-3,4-icosanediol, and Compound 28: (2S,3S,4R)-1-(α-D-galactopyranosyloxy)-2-[(S)-2-hydroxytetracosanoylamino]-3,4-heptadecanediol. (4) Compounds represented by the following formula (XII) or (XIV'):

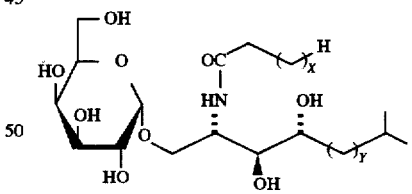

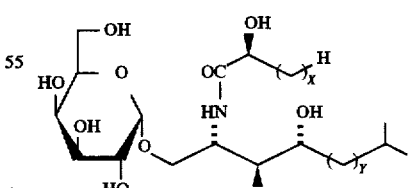

Compound 30: (2S,3S,4R)-1-(α-D-galactopyranosyloxy)-2-[(S)-2-hydroxytetracosanoylamino]-16-methyl-3,4-heptadecanediol, and Compound 31: (2S,3S,4R)-1-(α-D-galactopyranosyloxy)-16-methyl-2-tetracosanoylamino-3,4-heptadecanediol.

(5) Compound represented by the following formula (XIX):

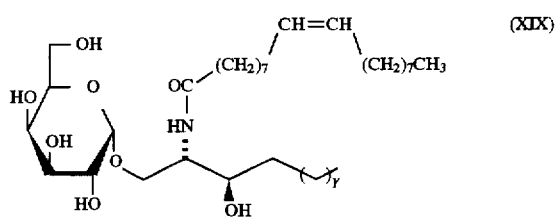

(XIX)

Compound 29: (2S,3R)-1-(α-D-galactopyranosyloxy)-2-oleoylamino-3-octadecanol.

Method for Preparing Compounds-Represented by Formula (A) (Outline)

These compounds can be chemically synthesized by the method described in the Application No. PCT/JP92/00561 which was filed by the inventors of the present invention.

An α-galactosylceramide represented by the above formula (A) (the formulas (I) and (XXI)) can be derived from sphingosine by applying thereto various chemical modifications. However, it is also possible to synthesize the α-galactosylceramide by a chemical synthesis method in which various general chemical reactions necessary for the synthesis of sphingoglycolipid are used in combination. There is no single route of synthesis and a desired compound can be derived from a different starting material via a different route. The compound can also be synthesized by utilizing a general chemical synthesis method regarding sphingoglycolipid, for example, by the method described in "Agricultural and Biological Chemistry", Vol. 54, No. 3, p. 663 (1990). It can also be synthesized, for example, by the method described in "Liebigs Annalen der Chemie", p. 663 (1988), in which method various saccharides are used as starting materials. In these synthesis methods, a protective group is removed after sugar is combined with a ceramide. However, it is also possible to adopt the method as described in "Liebigs Annalen der Chemie", p. 669 (1988), in which method sugar is firstly combined with a long-chain base and then amidation is conducted by introducing an amino group to obtain cerebroside. (Synthesis Route A)

As an example of the above-described synthesis can be mentioned the following process by which the compounds represented by the above formula (III), (V) or (XIX) can be synthesized (see FIG. 1, a and b).

In FIG. 1, the following abbreviations are used:

Bn: benzyl,

R4: hydroxyl group or formyloxy group,

Ms: methanesulfonyl,

R5: hydrogen atom or acyloxy group,

Tr: triphenylmethyl, and

Bz: benzoyl.

The aldehyde used as a starting material has 1 or 2 points of asymmetry. Amino acid or saccharide can be utilized as an asymmetry-causing source. In this example, a benzyl group is used as a hydroxy-protective group. However, any group which is fit for the purpose, such as an isopropylidene group, can also be used.

In particular, regarding the amidation in the route shown in the diagram, many reaction methods are known.

Instead of using carboxylic acid, an acid chloride or an acid anhydride can be used.

The reaction using carboxylic acid is a condensation reaction which is carried out in the presence of a proper condensation agent. Examples of the condensation agent herein used include dicyclohexylcarbodiimide (DCC), 2-ethoxy-1-ethoxycarbonyl-1,2-dihydroquinoline (EEDQ),
1-ethyl-3-(3-dimethylaminopropyl)-carbodiimide (WSC), chlorocarbonates and onium salts. In order to accelerate the reaction, an organic base such as triethylamine, pyridine, N-methylmorpholine, dimethylaniline, 4-dimethylaminopyridine, N-methylpiperidine or N-methylpyrrolidine is added. Any inert solvent which does not participate in the reaction can be used.

In general, a reaction using an acid chloride conveniently proceeds in the presence of a solvent. The reaction is usually carried out by using a proper solvent. However, when the reaction speed is low, it is suitable to carry out the reaction in the absence of a solvent. The reaction can thus be accelerated. Any solvent can be used as long as it is inert and does not participate in the reaction. In the case where the reaction speed is low, the addition of an organic base such as triethylamine, pyridine, N-methylmorpholine, dimethylaniline or 4-dimethylaminopyridine is sometimes useful for accelerating the reaction.

A reaction using an acid anhydride is preferably carried out in the presence of a proper base. A base herein used is triethylamine, pyridine or the like, and, in general, these bases also serve as solvents.

Further, many reaction methods regarding glycosylation are also known, and they are summarized in the following references: (1) "Organic Synthetic Chemistry", Vol. 38, No. 5, p. 473 (1980), (2) "Organic Synthetic Chemistry", Vol. 41, No. 8, p. 701 (1983) and (3) "Pure and Applied Chemistry", Vol. 61, No. 7, p. 1257 (1991).

Any of the above reactions can be employed. However, a method in which α-galactoside is preferentially obtained (for example, the method described on pages 431–432 of "Chemistry Letters" (1981)) is preferred. When an α-compound cannot be solely obtained, separation between α- and β-compounds is conducted. However, when it is difficult to conduct this separation, it is suitable to change a hydroxyl group to an acyl derivative (for example, acetyl). The separation between the α- and β-compounds is thus made possible. (Synthesis Route B)

Figure 2:
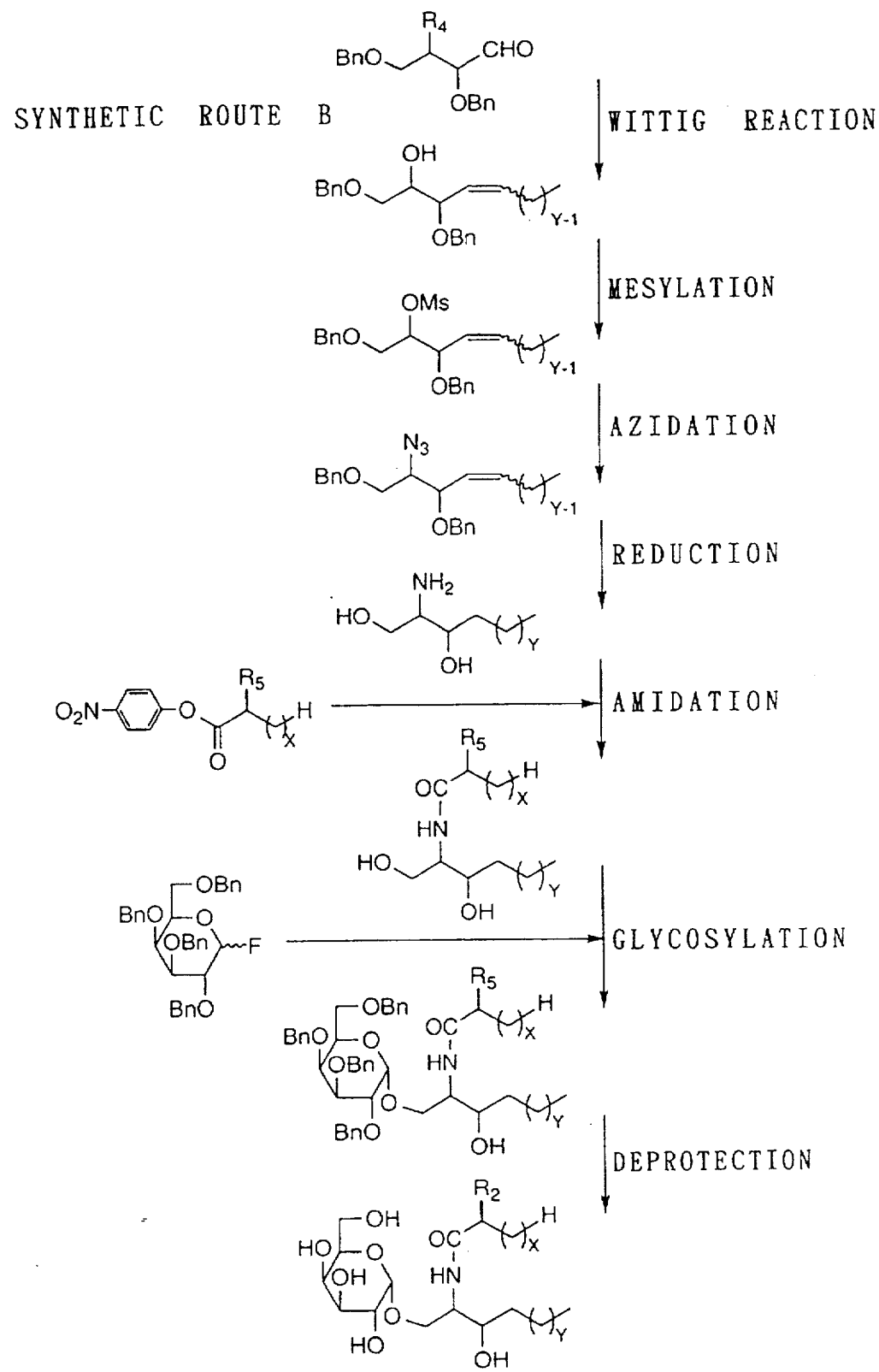
FIG. 2 is a diagram showing a reaction route (synthesis route B) for synthesizing a compound represented by the formula (A), using as a starting material an aldehyde compound as mentioned regarding FIG. 1, which route includes fewer steps than the synthesis route A.

The following reaction route can be presented as a shorter process starting with the same starting material as in the synthesis route A. The compounds represented by the above formula (III), (V) or (XIX) can also be synthesized by this method (see FIG. 2). The abbreviations used in FIG. 2 are the same as before. This route is characterized in that reduction of an azido group, elimination of a benzyl group and reduction of a double bond are simultaneously conducted upon reduction of an azide compound. The number of steps in the route is thus reduced. By the reduction, 2-amino-1,3-alkanediol can be obtained as an intermediate. Four respective isomers of this compound can be singly obtained by properly selecting an asymmetry-causing source for the aldehyde used as a starting material. The isomers obtained are separately subjected to amidation. In this process, various methods of amidation as described in the route A are employable. After this, glycosylation and deprotection are conducted in the same manner as in the route A to obtain a desired compound. (Synthesis Route C)

Figure 3:
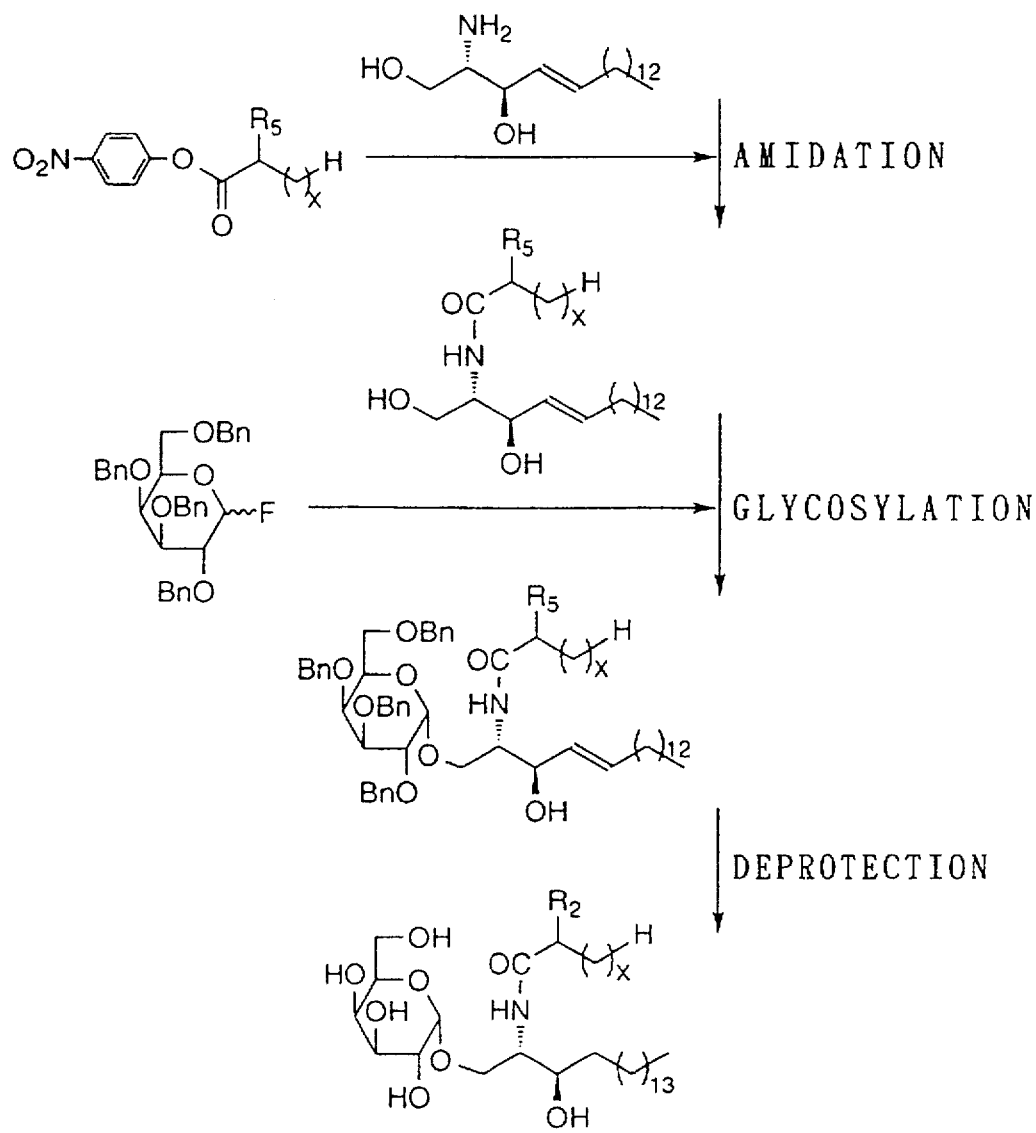
FIG. 3 is a diagram showing a reaction route (synthesis route C) for deriving a compound represented by the formula (A) from sphingosine, a starting material, by applying thereto various chemical modifications.

One example of synthesis in which compounds are derived from sphingosine by applying thereto various chemical modifications is the below-described process. Of the compounds represented by the above formula (IV), (VI), (XVI) or (XX), those compound whose long-chain base moiety contains 18 carbon atoms can also be synthesized by this process (see FIG. 3). The abbreviations used in FIG. 3 are the same as before. Sphingosine can be extracted from natural product. However, it is commercially available from Sigma Chemical Company, Funakoshi Co., Ltd. or the like. It can also be synthesized by one of various synthesis methods described in "Pharmacia", Vol. 27, p. 1164 (1991) and "Journal of the Chemical Society Perkin Transactions 1", p. 2279 (1991). Isomers of sphingosine which are different from natural products in the configuration can also be synthesized by the method described in "Helvetica Chimica cta", Vol. 40, p. 1145 (1957) or "Journal of the Chemical Society Chemical Communications", p. 820 (1991). In the latter reference cited, many synthesis examples are described. According to this route, it is possible to leave a double bond even after glycosylation. Namely, when catalytic reduction is carried out for final deprotection, a compound having no double bond can be obtained; and when a protected compound is treated with metal sodium in liquid ammonia for final deprotection, a compound with a double bond remaining can be obtained. A desired compound can thus be obtained. (Synthesis Route D)

Figure 4:
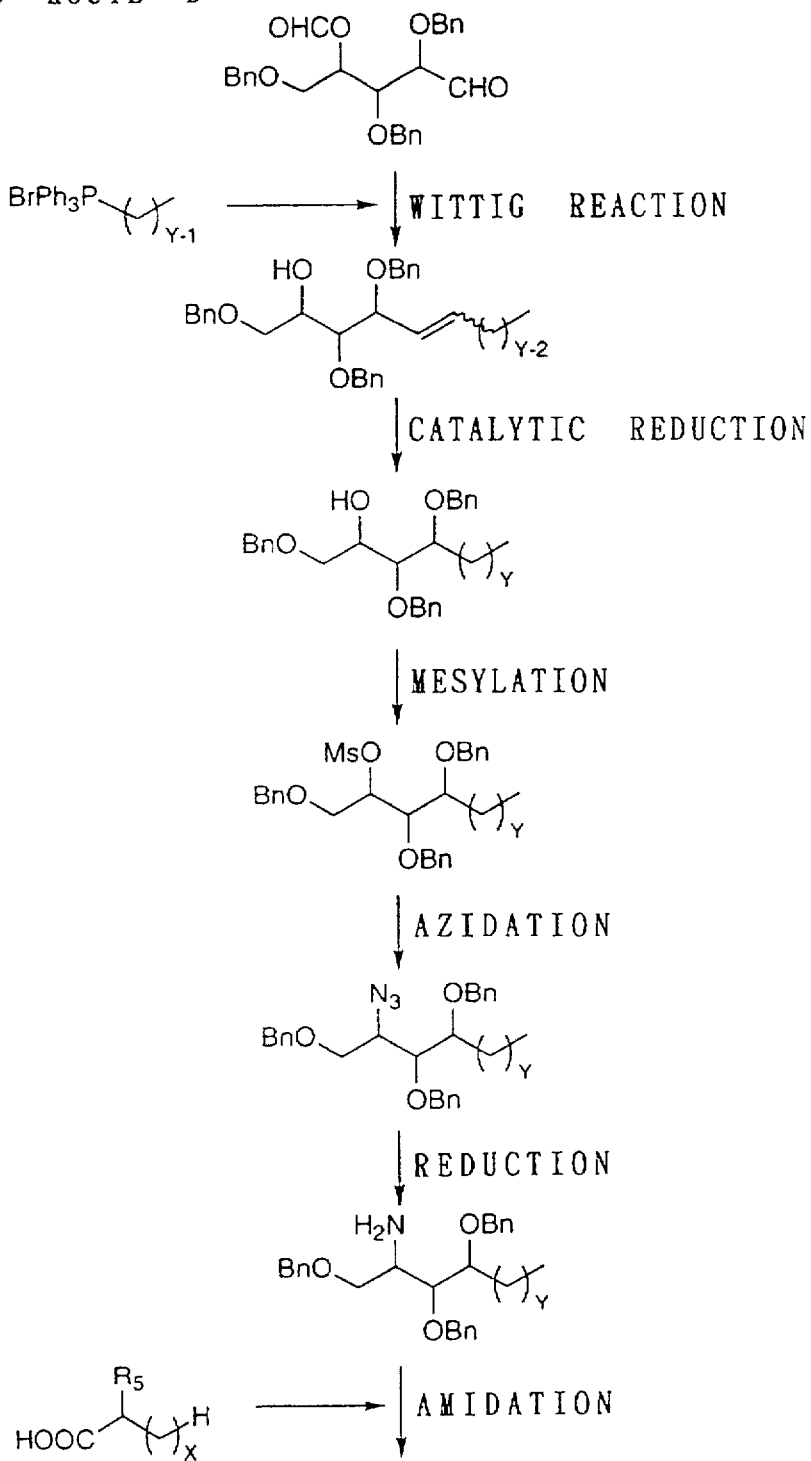
FIG. 4 (a–c) is a diagram showing a reaction route (synthesis route D) for synthesizing, using as a starting material an aldehyde compound, a compound represented by the formula (A) in which the 4-position of the long-chain base moiety is a hydroxyl group.
Figure 4:
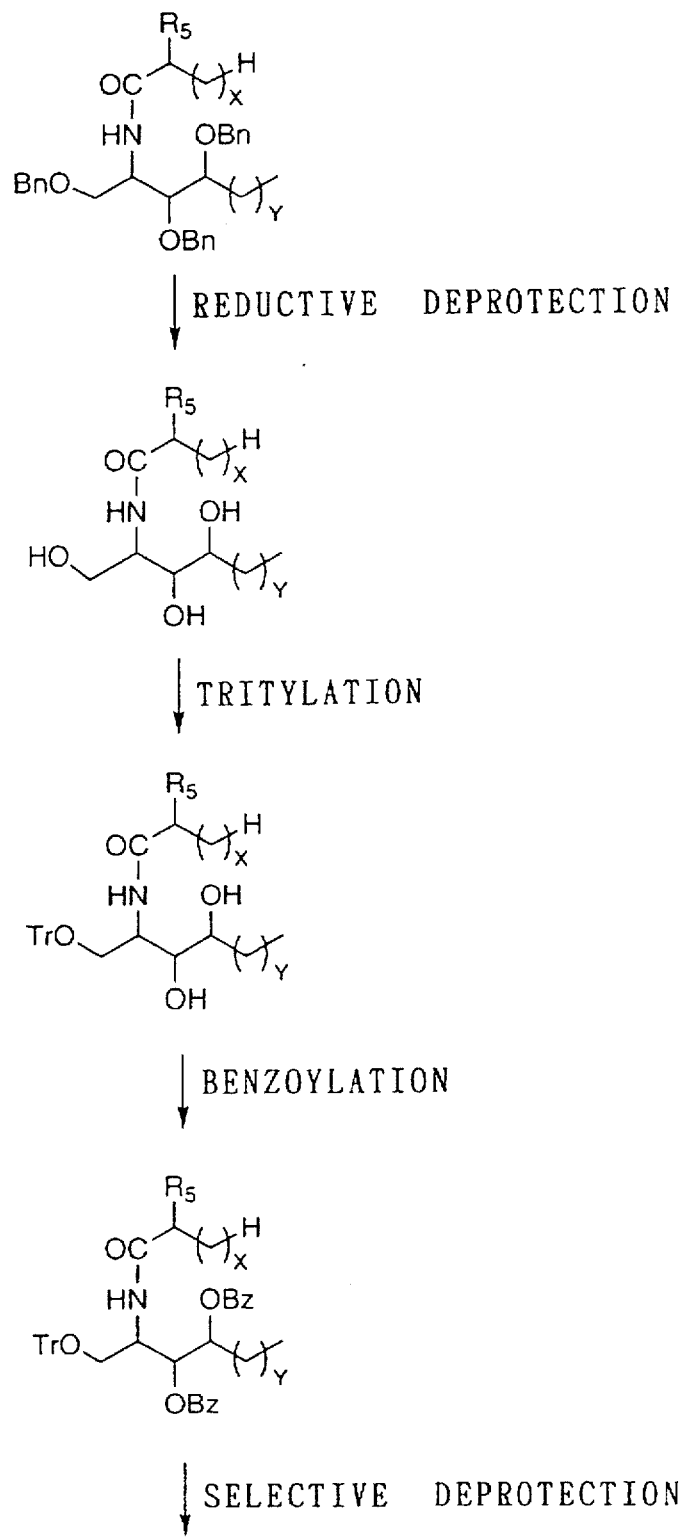
Figure 4:
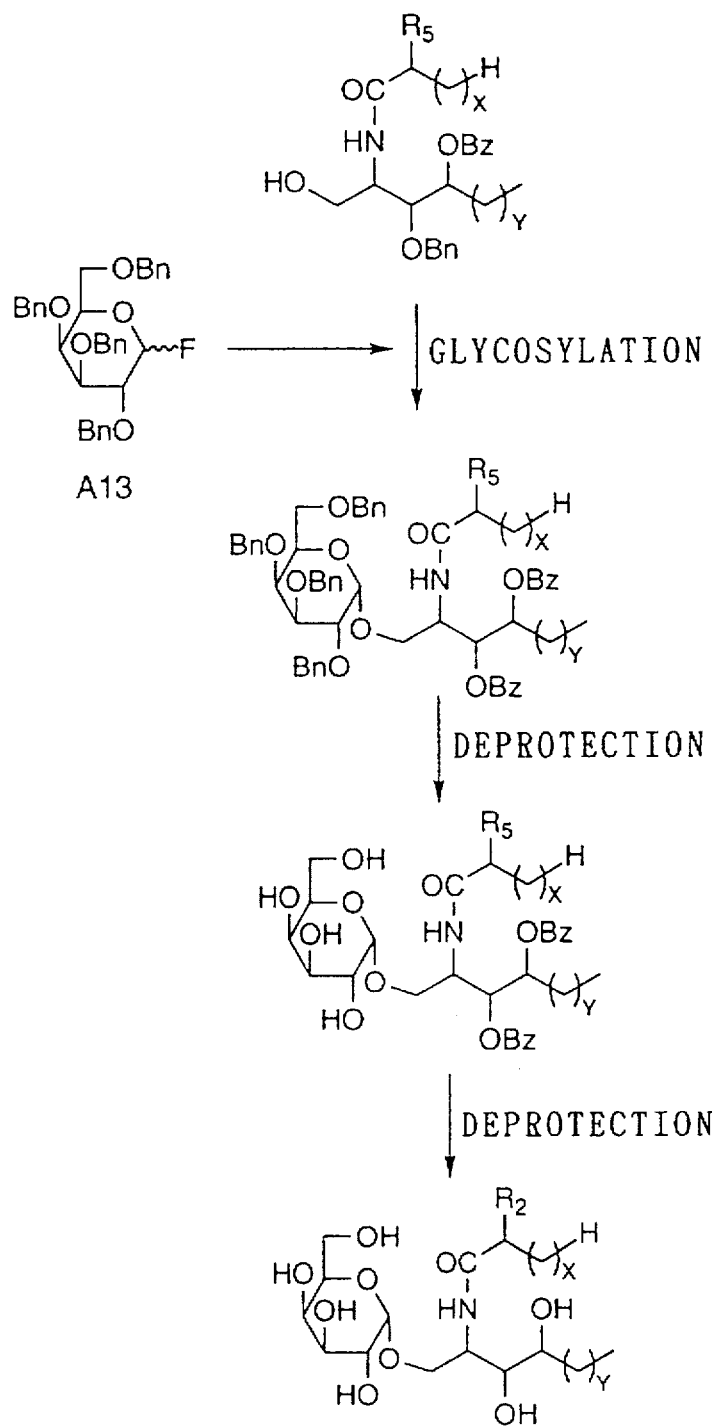
Figure 5:
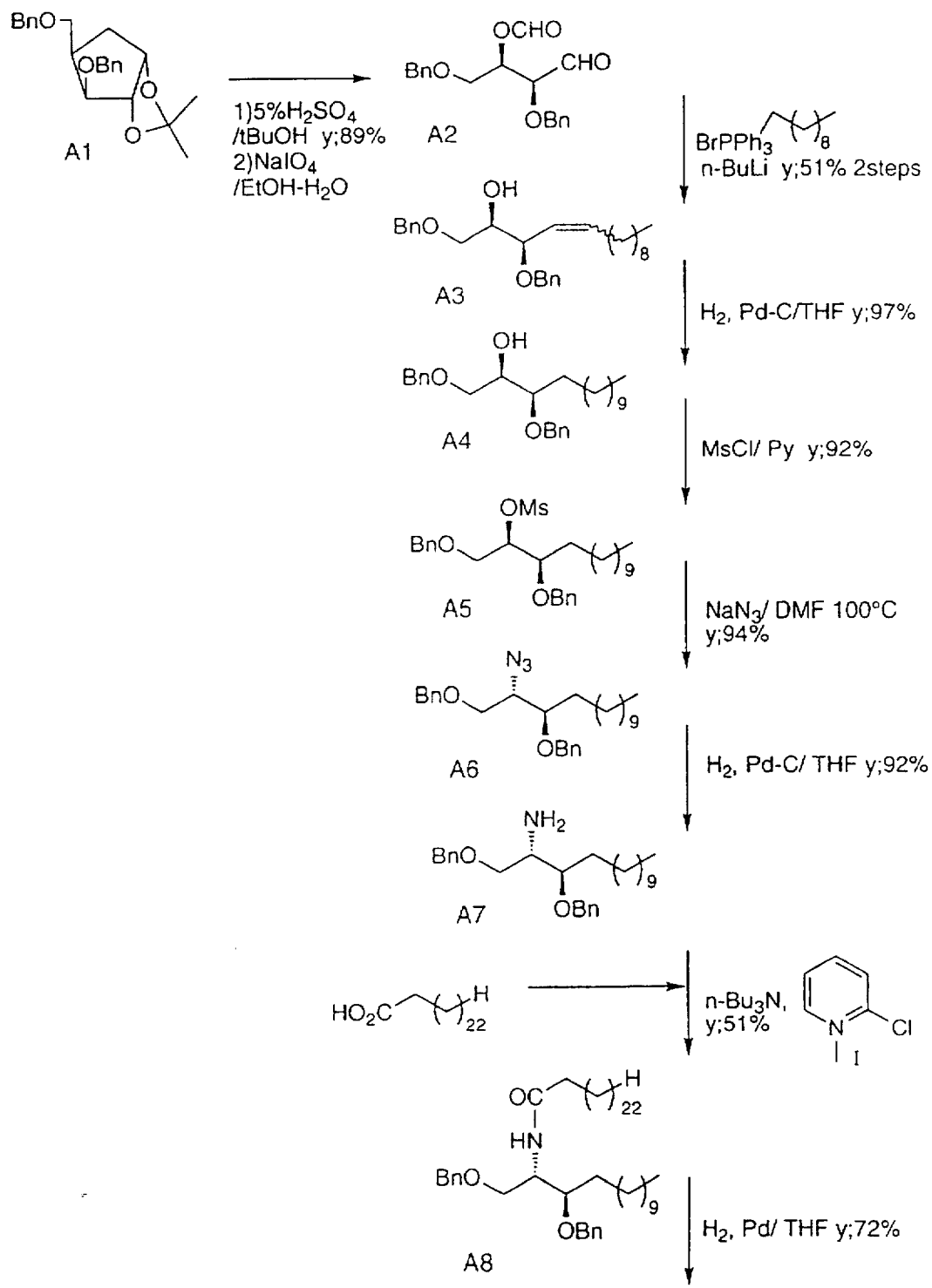
FIG. 5 (a and b) is a diagram showing a reaction route which shows a preferable method for synthesizing Compound 9 ((2S,3R)-1-(α-D-galactopyranosyloxy)-2-tetracosanoylamino-3-tetradecanol).
Figure 5:
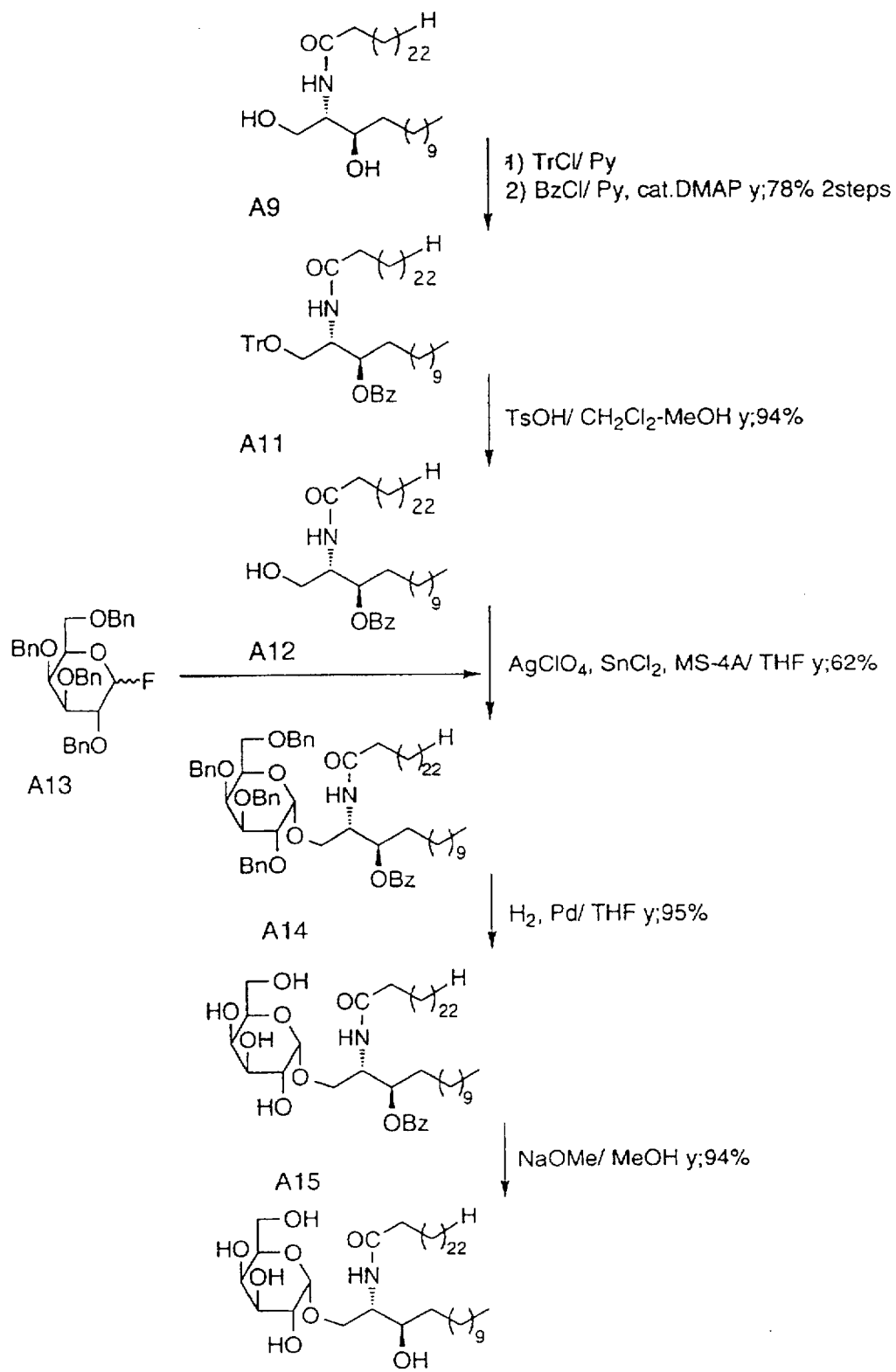
Figure 6:
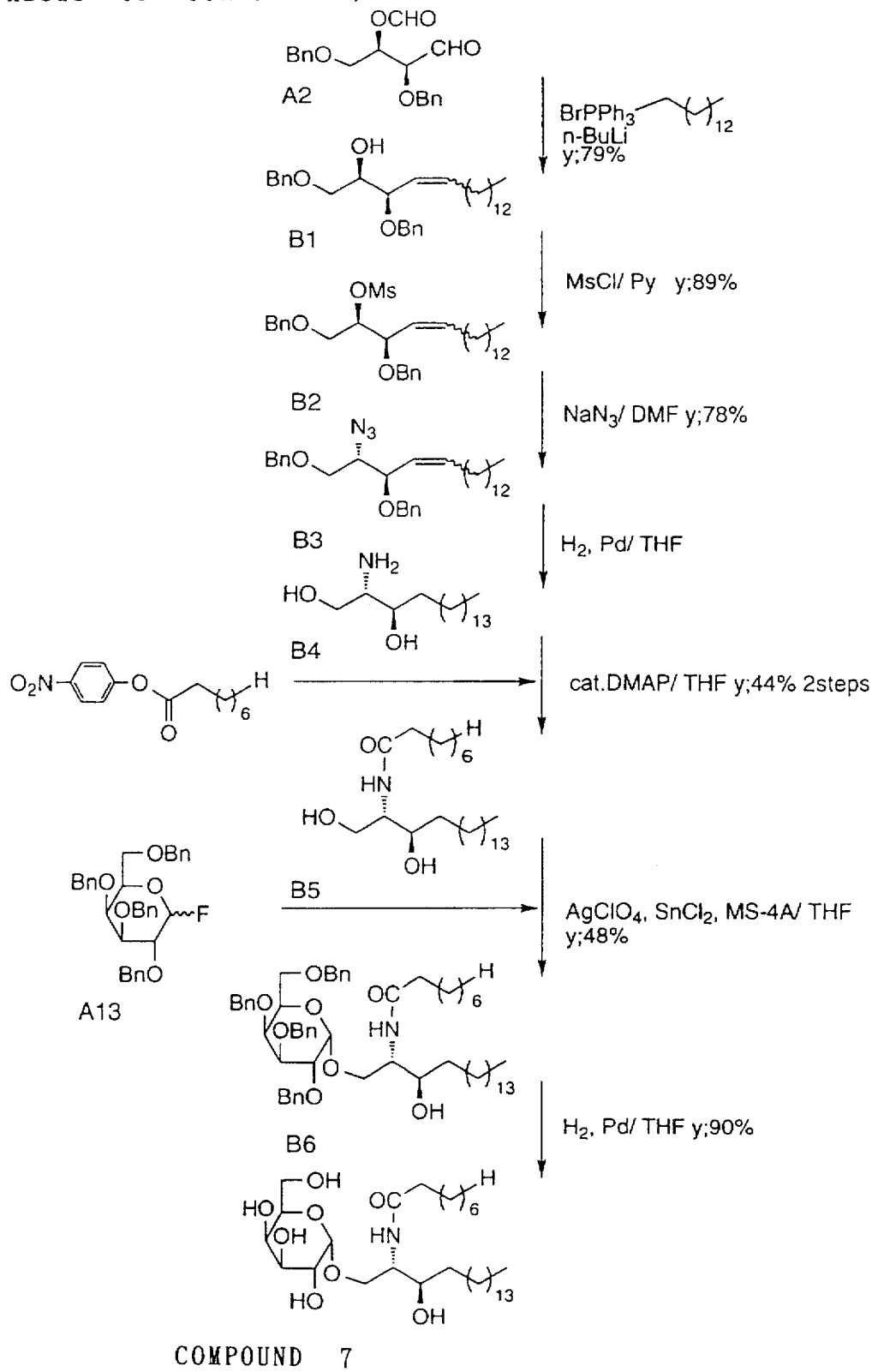
FIG. 6 is a diagram showing a reaction route which shows a preferable method for synthesizing Compound 7 ((2S,3R)-1-(α-D-galactopyranosyloxy)-2-octanoylamino-3-octadecanol).
Figure 7:
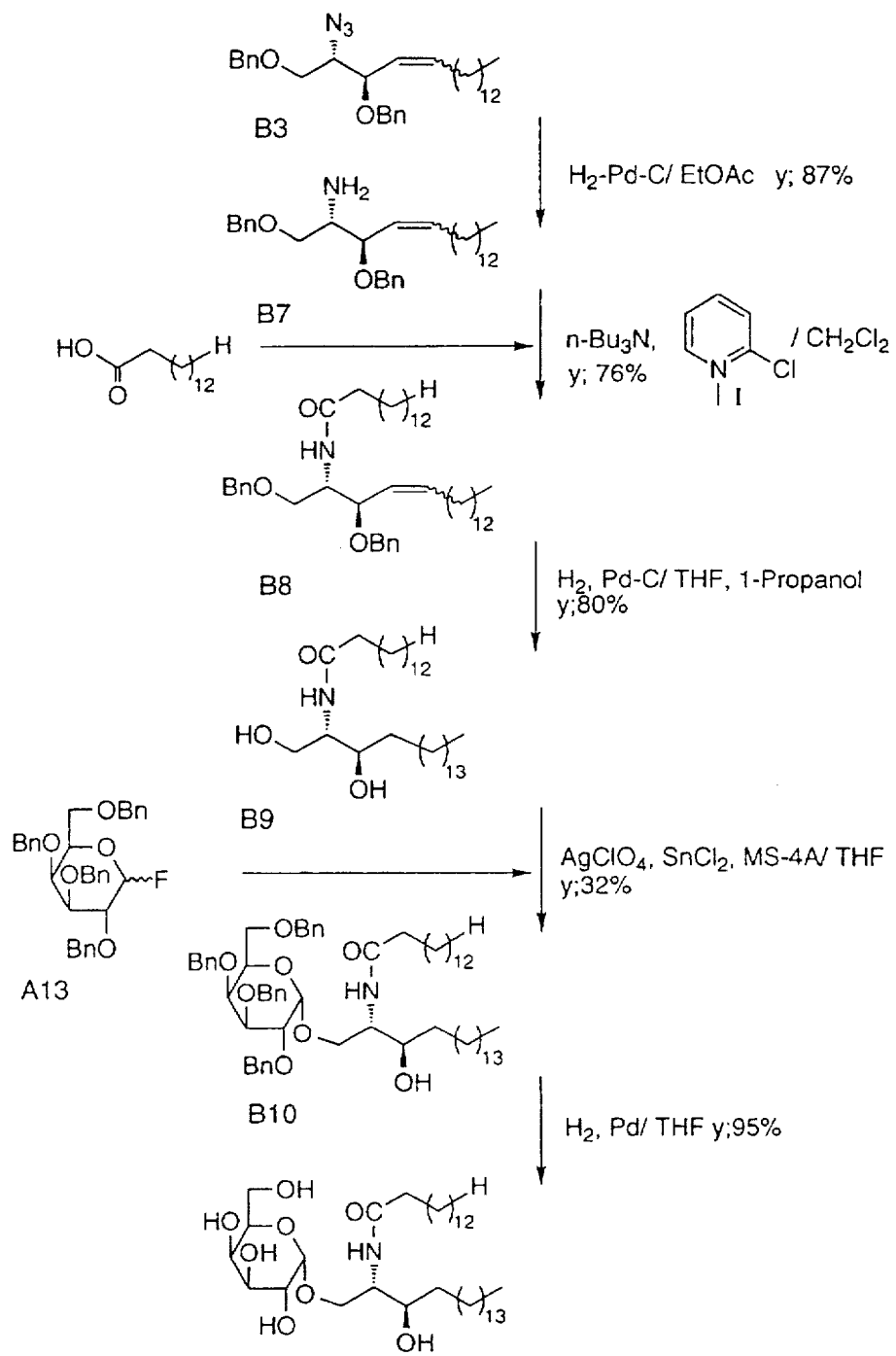
FIG. 7 is a diagram showing a reaction route which 30 shows a preferable method for synthesizing Compound 5 ((2S,3R)-1-(α-D-galactopyranosyloxy)-2-tetradecanoylamino-3-octadecanol).
Figure 8:
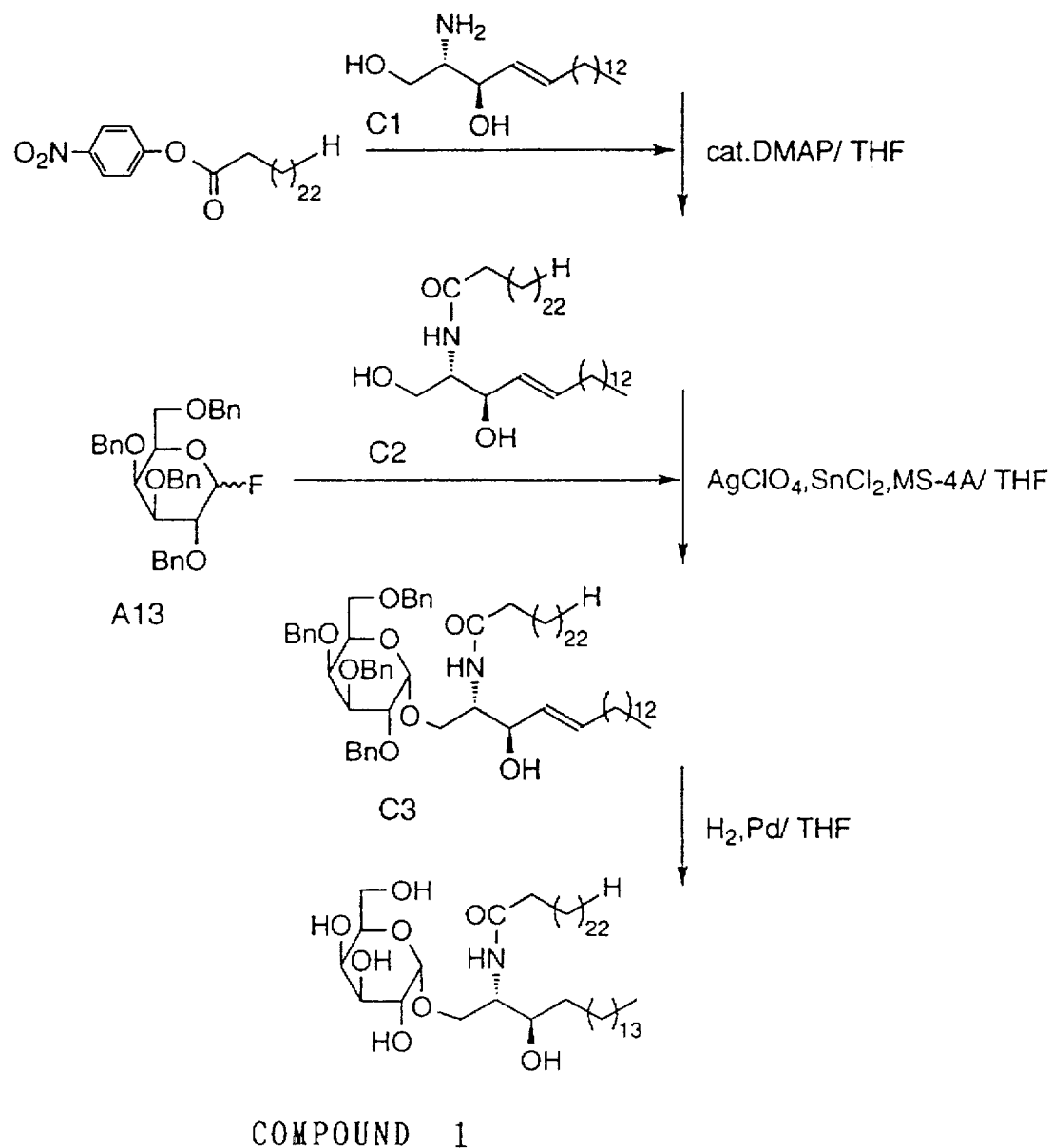
FIG. 8 is a diagram showing a reaction route which shows a preferable method for synthesizing Compound 1 ((2S,3R)-1-(α-D-galactopyranosyloxy)-2-tetracosanoyl-amino-3-octadecanol).
Figure 9:
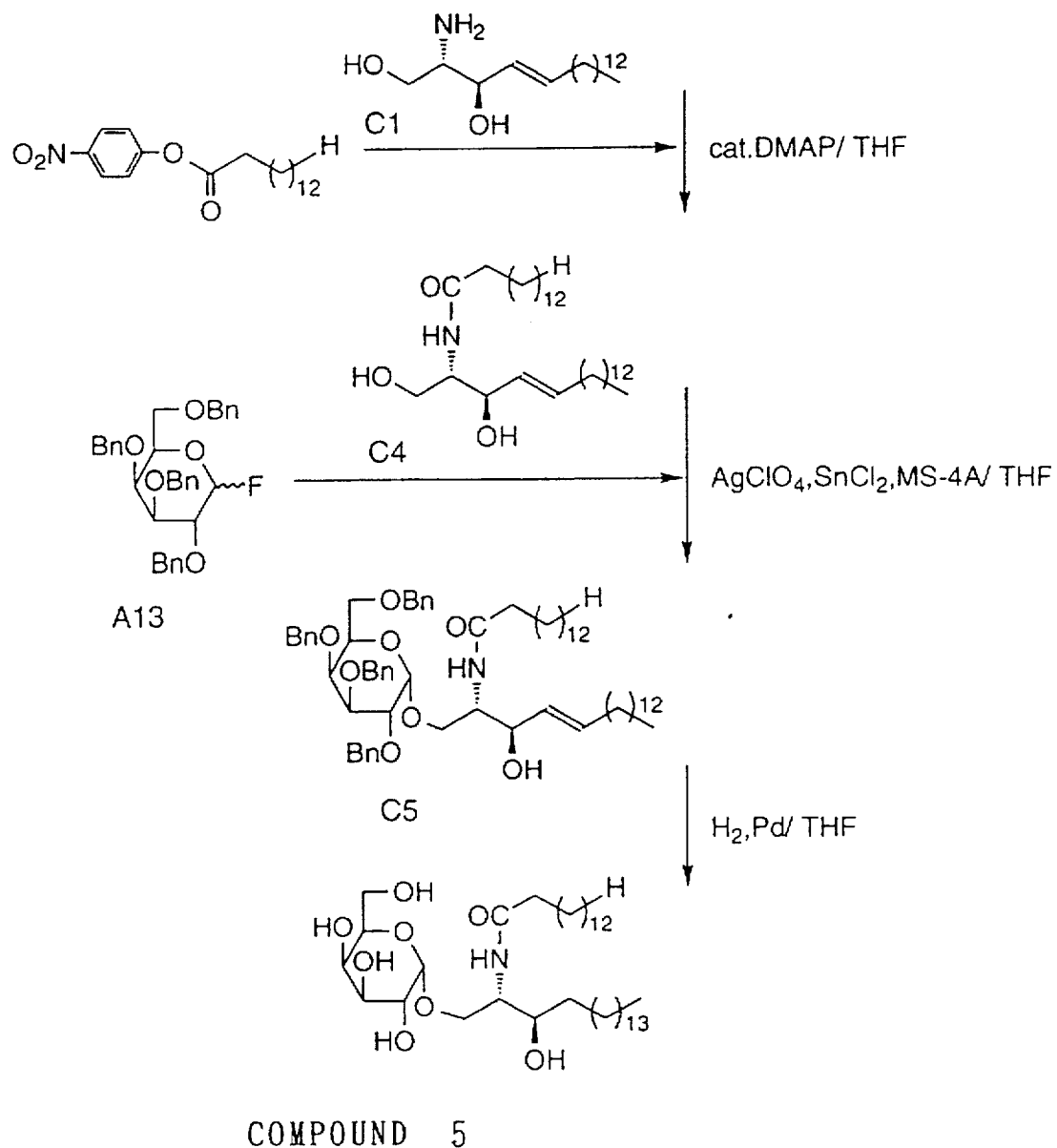
FIG. 9 is a diagram showing a reaction route which shows another preferable method for synthesizing Compound 5.
Figure 10:
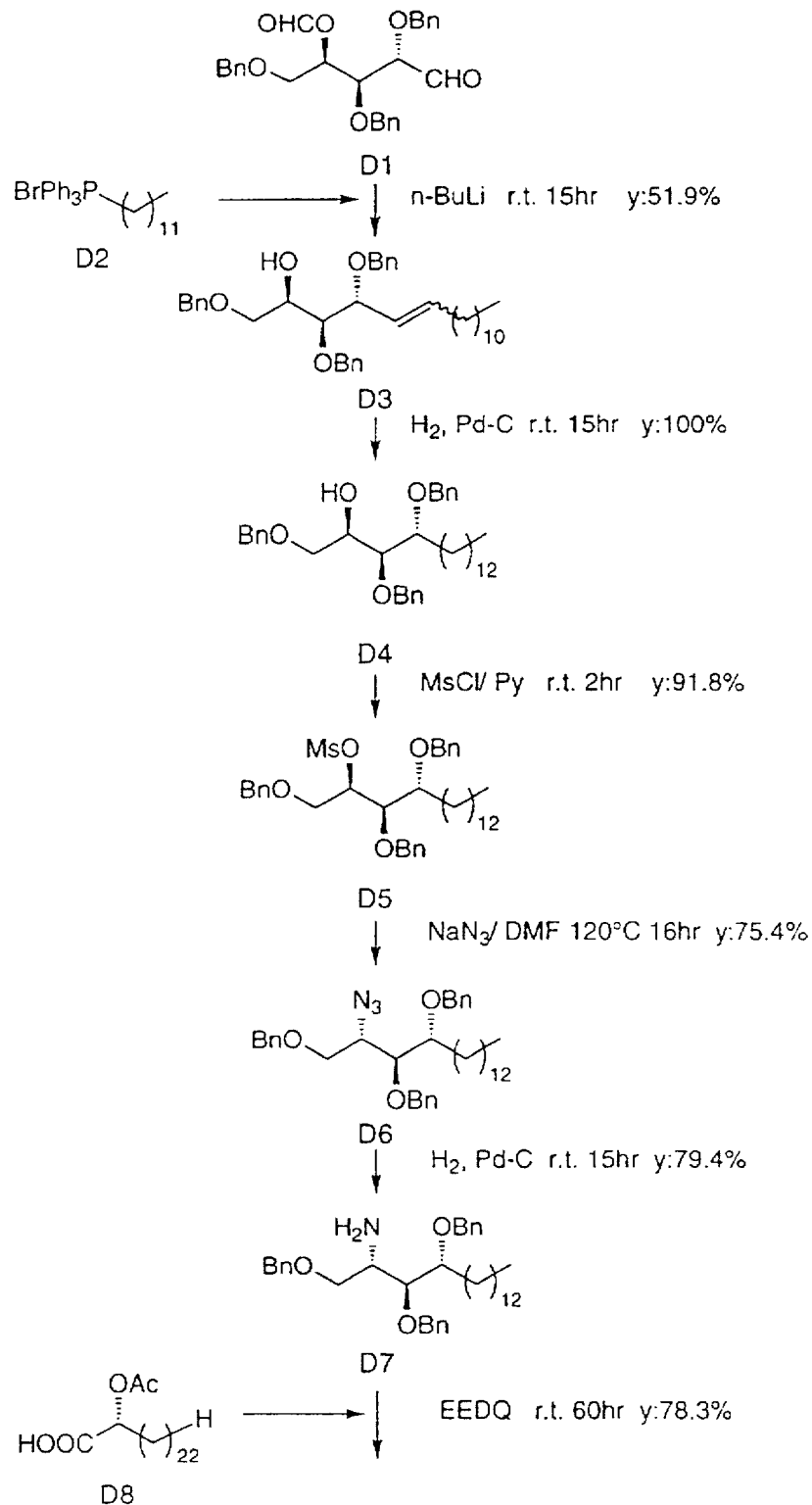
FIG. 10 (a–c) is a diagram showing a reaction route which shows a preferable method for synthesizing Compound 22 ((2S,3S,4R)-1-(α-D-galactopyranosyloxy)-2-[(R)-2-hydroxyltetracosanoylamino]-3,4-heptandecanediol).
Figure 10:
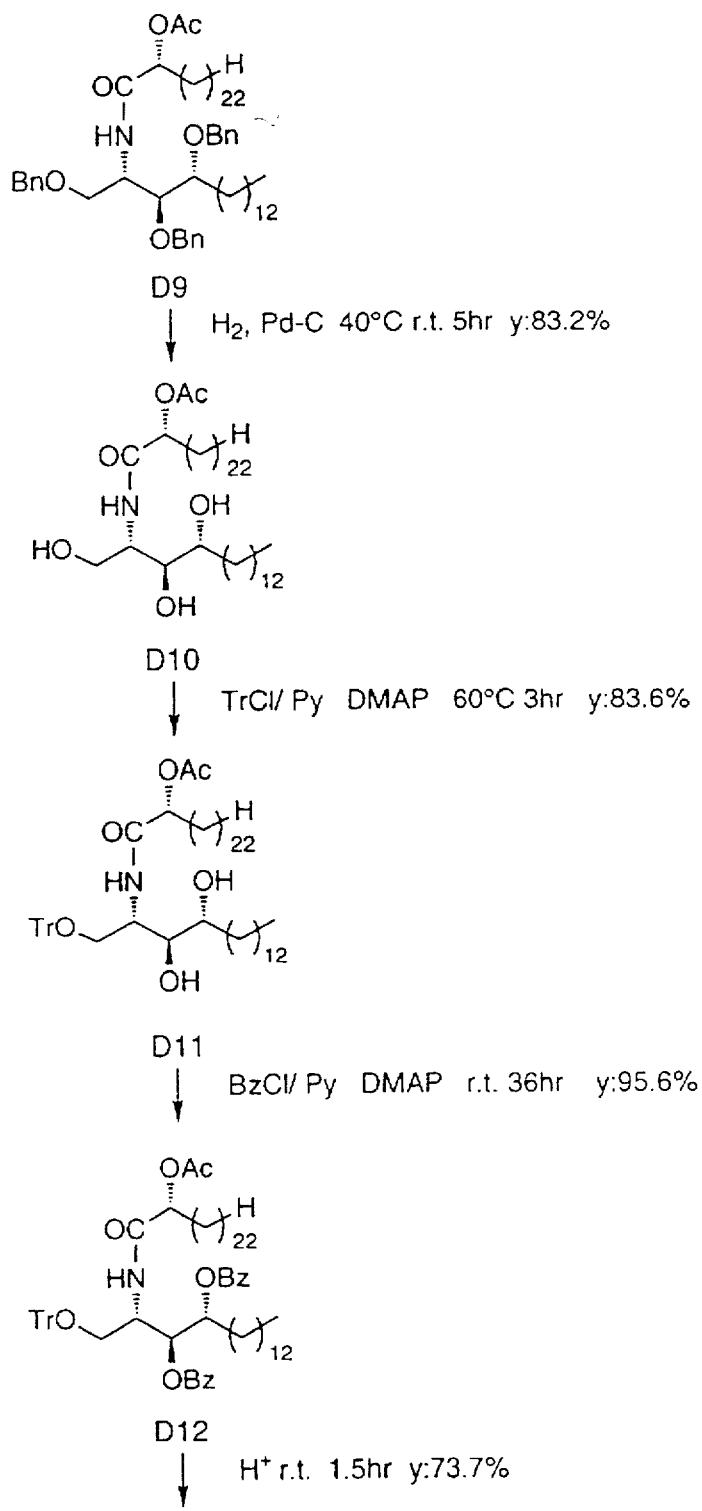
Figure 10:
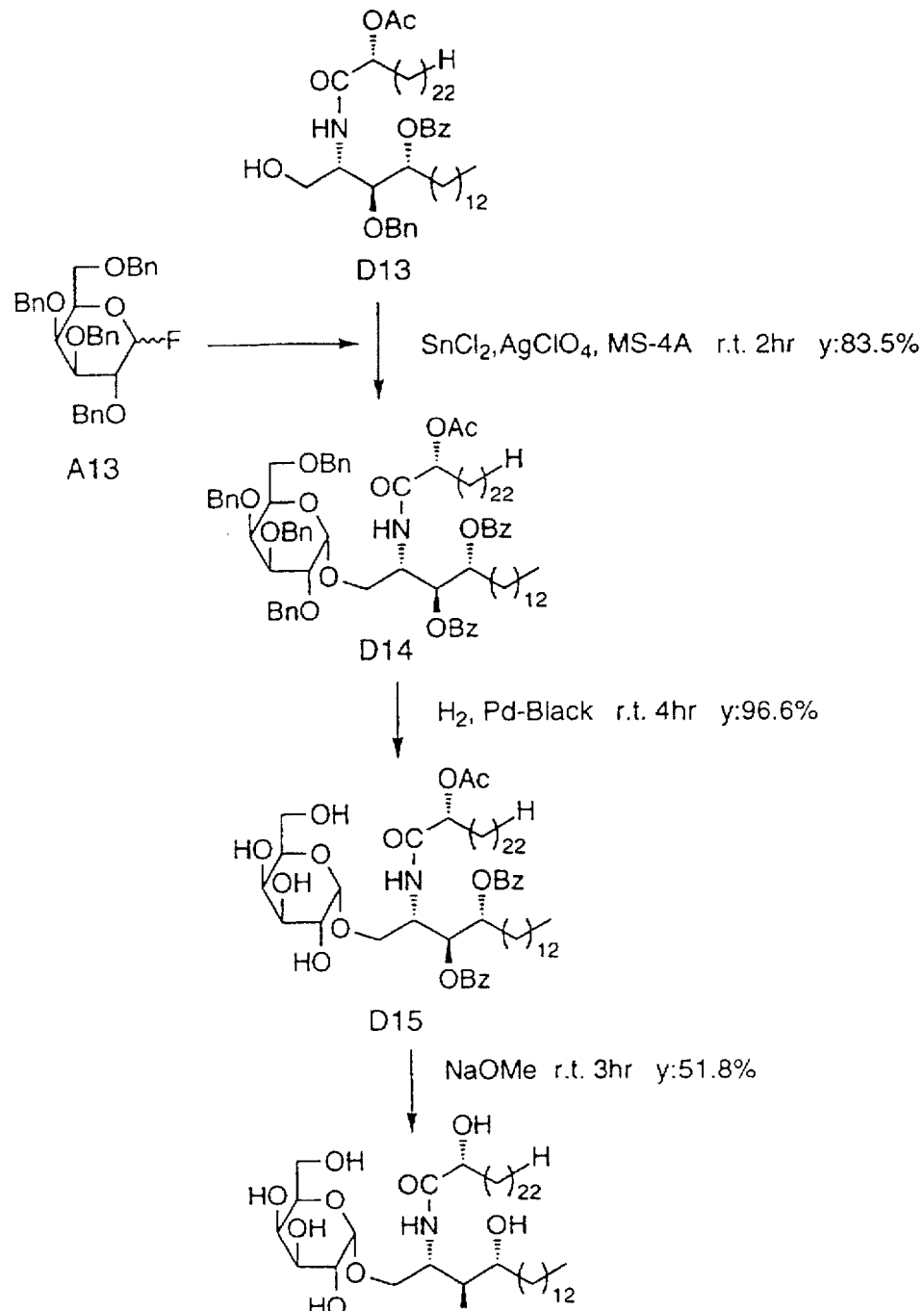

Of those compounds which have a hydroxyl group at the 4-position of a long-chain base in the formula (A), compounds represented by the formula (VII), (IX), (XI), (XIII) or (XVII) can also be synthesized via the following process (see FIG. 4(a–c)). The abbreviations used in FIG. 4 are the same as those used in the above process.

The aldehyde, a starting material, can be freely made into its isomers by properly selecting an asymmetry-causing source, and the respective isomers can be obtained singly. The isomers thus obtained are separately subjected to the subsequent Wittig reaction. It is easy to change the terminal end of the Wittig salt to an iso type, an anti-iso type or a straight-chain type. In general, the Wittig reaction using such an unstable ylide gives, as a main product, a compound having a cis-type double bond. However, a compound having a trans-type double bond is also produced. A mixture of such compounds is acceptable because the double bonds contained in the mixture are changed into single bonds in the step of catalytic reduction. Mesylation and azido inversion are conducted, followed by reduction to give an amino group which is subjected to amidation in the subsequent step to give a ceramide. Such a protected ceramide, an intermediate, can also be repared by using as a starting material Cereblin E (a roduct of Alfred Bader Chemicals or K & K Laboratories, Inc.), and protecting it with a protective group which is fit for the purpose. Further, in order to distinguish from the other groups a hydroxyl group with which sugar is combined, it is protected and deprotected, and then glycosylated and deprotected to give a desired compound (FIG. 4).

Pharmaceutical Composition and Therapeutic (or Prophylactic) Method

As mentioned previously, the pharmaceutical composition or medicine (a marrow cell proliferation accelerator, a radioprotective agent, a therapeutic agent for thrombocytopenia) according to the present invention comprises as an active ingredient at least one compound represented by the formula (A) (i.e. the formulas (I) and (XXI)) together with a carrier or a diluent; and the therapeutic or prophylactic method (a method for proliferating marrow cells, a method for protecting human against radiation damage, a method for the treatment of thrombocytopenia) according to the present invention comprises administering an effective amount of a compound represented by the formula (A) (the formula (I) or (XXI)) to human.

In the present invention, the compounds represented by the formula (A) have a marrow-cell-proliferation-accelerating effect, so that they are considered to be effective for the amelioration or treatment of severe infectious diseases, blood dyscrasia (e.g. leukemia and osteomyelodysplasia), liver cirrhosis, splenomegaly, systematic lupus erythematosus, and a drastic decrease in the number of marrow cells caused by administration of an anticancer agent, or upon radiotherapy, and to be useful for accelerating marrow cell proliferation at the time of bone marrow transplantation.

Further, in the present invention, the compounds represented by the formula (A) have a radioprotective effect. Therefore, they show extremely excellent prophylactic and therapeutic effects when they are administered before or after irradiation with radiation, and, in particular, show an excellent life-span-increasing effect against irradiation of a lethal dose of radiation.

Furthermore, in the present invention, the compounds represented by the formula (A) have excellent blood-platelet-increasing and blood-platelet-decrease-inhibitory effects. Therefore, when they are administered to a patient of thrombocytopenia, or to the organism whose blood platelets are decreased in the number due to chemotherapy or radiotherapy for cancer, they show an excellent blood-platelet-increasing effect or blood-platelet-decrease-inhibitory effect.

The compounds represented by the formula (A), used for the medicine or the method according to the present invention can be administered by any administration route -which is fit for the purpose. Specifically, the compounds can be administered to animals by any one of such methods as intraperitoneal administration, subcutaneous administration, vascular administration such as intravenous or intra-arterial administration, and topical administration by injection; and they can be administered to a human by any one of such methods as intravenous administration, intra-arterial administration, topical administration by injection, administration to peritoneal or pleural cavity, oral administration, subcutaneous administration, intramuscular administration, sublingual administration, percutaneous administration and rectal administration.

Further, the compounds represented by the formula (A), used for the medicine and the method according to the present invention can be administered in a form properly determined depending on the method and the purpose of administration, specifically in a form of injection, suspension, emulsion, tablet, granule, powder, capsule, troche, ointment, dry syrup or cream. Upon producing these preparations, a pharmaceutically acceptable additive such as a carrier or diluent, specifically, a solvent, a solubilizing agent, an isotonicating agent, a preservative, an antioxidant, an excipient, a binding agent, a lubricant, a stabilizer or the like may be added.

Examples of the solvent include distilled water for injections and physiological saline. Examples of the solubilizing agent include ethanol, Polysorbates and Macrotigols. Examples of the excipient include lactose, starch, crystalline cellulose, mannitol, maltose, calcium hydrogenphosphate, light silicic acid anhydride and calcium carbonate. Examples of the binding agent include starch, polyvinylpyrrolidone, hydroxypropylcellulose (HPC), ethylcellulose, carboxymethylcellulose and gum arabic. Examples of the disintegrator include starch and carboxymethylcellulose calcium (CMC—Ca). Examples of the lubricant include magnesium stearate, talc and hardened oil. Examples of the stabilizing agent include lactose, mannitol, maltose, Polysorbates, Macrogols and polyoxyethylene hardened castor oil. Further, glycerin, dimethylacetamide, 70% sodium lactate, a surface active agent, and a basic material (for example, ethylene diamine, ethanol amine, sodium carbonate, arginine, Meglumine, trisaminomethane) may also be added, if necessary. By using these ingredients, the above-described preparations can be obtained.

The dose of the compound represented by the formula (A) (i.e. the formulas (I) and (XXI)) used for the medicine and the method according to the present invention is determined, in consideration of the results obtained by tests using animals and the particular condition, so as not to exceed a predetermined amount when the compound is administered continuously or intermittently. It is needless to say that the specific dose varies depending on administration route, the state of a patient or a test animal, such as age, body weight, sex and sensitivity, diet, time for administration, drugs to be used in combination, and the condition of a patient or a disease. Further, the optimum dose and the frequency of administration under a certain condition should be determined by a specialist on the basis of the above-described guidelines and the results of an optimum dose determining test. The dose at which the compound represented by the formula (A) reveals its activity is, in general, approximately 0.01 to 100 mg/day per human adult. This range was determined on the basis of the dose for intravenous administration to a croo monkey, and that for oral administration to a mouse.

Referential Examples

The method for preparing specific compounds represented by the formula (A), used for the medicine and the method according to the present invention is described in the specification of the PCT Application (PCT/JP92/00561) mentioned previously.

The methods for synthesizing these compounds and the physicochemical properties of the compounds are as follows (see the synthesis routes shown in FIGS. 1 to 10):

(1) Synthetic route A

While this reaction route scheme is shown specifically with reference to the aforementioned compound 9, the compounds 1–8 and 10–14 according to the present invention can also be synthesized by applying this method (see FIGS. 5a and 5b).

In the above scheme, the following abbreviations are used.
DMAP: 4-dimethylaminopyridine, TsOH: p-toluenesulfonic acid, MS-4A: Molecular Sieves-4A (dehydrating agent).

The other abbreviations have the same meanings as in the previous route schemes.

Furthermore, the compound 29 leaving a double bond unreacted therein can be synthesized by the use of a fatty acid having a double bond as a starting material and by the deprotection at the final step with liquid ammonia and metallic sodium. [Synthesis of the compound 9 (FIGS. 5a and 5b)]

The compound A1 can be synthesized in accordance with the method described in Synthesis, 961–963, 1984. (i) Synthesis of the compound A2

To a solution of the compound A1 (2.89 g) in 2-methyl-2-propanol (25 ml) was added a 5% aqueous sulfuric acid solution (25 ml), and the mixture was stirred at 45° C. for 15 hours. After being neutralized with powdery sodium hydrogen carbonate under ice-cooling, the reaction mixture was concentrated. The residue, to which water (30 ml) was added, was extracted with ethyl acetate (three times), and the organic layer was concentrated. Purification on a silica gel column (Wako Gel C-200, 100 g) using hexane-acetone (2:1) as an eluent afforded a diol in an amount of 2.28 g (yield: 88.5%). MS: FDMS 330.

The mixture of the diol (2.25 g) with ethanol (50 ml), water (12 ml) and sodium metaperiodate (2.33 g) was stirred at room temperature for 10 hours. Precipitates were removed by filtration, and the filtrate was concentrated. The residue was diluted with chloroform and washed with brine. The organic layer was concentrated to give an aldehyde (compound A2) in an amount of 1.31 g. The aldehyde was directly used for the next reaction without purification. (ii) Synthesis of the compound A3

To decanetriphenylphosphonium bromide (8.0 g) was added tetrahydrofuran (20 ml) under an argon atmosphere. After adding a 2.8 N solution of n-butyllithium in hexane (6.2 ml) to the mixture at −10° C., stirring was continued for 30 minutes. After the addition of the aldehyde (compound A2, 1.31 g) dissolved in tetrahydrofuran (5 ml), the mixture was allowed to warm to room temperature and stirred for 15 hours and concentrated. The reaction mixture was diluted with brine, and extracted twice with ethyl acetate. The organic layer was washed with brine and concentrated. Purification of the residue on a silica gel column (Wako Gel C-200, 100 g) by eluting with hexane-ethyl acetate (5:1) gave the alcohol (compound A3) in an amount of 1.47 g (yield, 51.0%). Data of the compound A3 MS: FDMS 426. NMR: $^1$H (500 MHz, CDCl$_3$; 27° C.)

δ (Ppm) 7.25–7.35 (10H, m), 5.69–5.79 [1H, (5.75, dt, J=7.3, 11.0 Hz), (5.72, dt, J=6.7, 15.2 Hz)], 5.31–5.38 [1H, (5.36, bt, J=8.5 Hz), (5.33, bt, J=9.8 Hz)], 4.34–4.62 [2H, (4.61 & 4.35, ABq, J=11.6 Hz), (4.56 & 4.50, ABq, J=12.2 Hz), (4.55 & 4.52, ABq, J=11.6 Hz)], 4.28 (0.7H, dd, J=6.7, 9.7 Hz), 3.85 (0.3H, bt, J=7.9 Hz), 3.74–3.78 (1H, m), 3.56–3.60 [1H (3.59, dd, J=3.1, 9.8 Hz), (3.58, overlapped)], 3.47 (1H, dd, J=5.5, 9.8 Hz), 1.96–2.11 (1H, m), 1.25–1.57 (14H, m), 0.88 (3H, t, J=6.7 Hz).

(iii) Synthesis of the compound A4

The alcohol (compound A3, 0.83 g) was dissolved in tetrahydrofuran (10 ml). 10% Palladium on charcoal (1.0 g) was added, and the reaction vessel was purged with hydrogen. After the mixture was stirred at room temperature for 12 hours, it was filtered through celite and the filtrate was concentrated. Purification on a silica gel column (Wako Gel C-200, 30 g) eluting with hexane-ethyl acetate (5:1) afforded a reduction product (compound A4) in an amount of 0.81 g (yield, 97.1%). Data of the compound A4 MS: FDMS 428. NMR: $^1$H (500 MHz, CDCl$_3$; 27° C.)

δ (ppm) 7.25–7.46 (JOH, m), 4.50 & 4.62 (2H, ABq, J=11.0 Hz), 4.54 (2H, s), 3.79–3.83 (1H, m), 3.48–3.56 (3H, m), 2.42 (1H, d, J=6.1 Hz), 1.26–2.04 (20H, m), 0.88 (3H, t, J=7.3 Hz).

(iv) Synthesis of the compound A5

After adding methanesulfonyl chloride (0.29 ml) to the reduction product (compound A4, 0.80 g) in pyridine (15 ml), the mixture was stirred at room temperature for 16 hours. The reaction mixture was concentrated and distilled azeotropically with toluene. The residue dissolved in diethyl ether was washed with brine and concentrated. Purification on a silica gel column (Wako Gel C-200, 30 g) eluting with hexane-acetone (6:1) afforded a mesylated product (compound A5) in an amount of 0.87 g (yield, 91.9%). Data of the compound A5 MS: FDMS 504. NMR: $^1$H (500 MHz, CDCl$_3$; 27° C.)

δ (ppm) 7.27–7.38 (1OH, m), 4.81–4.84 (1H, m), 4.59 (2H, s), 4.55 & 4.50 (2H, ABq, J=11.6 Hz), 3.75 (1H, dd, J=3.1, 11.0 Hz), 3.71 (1H, dd, J=6.7, 11.0 Hz), 3.67 (1H, dt, J=4.3, 8.5 Hz), 2.99 (3H, s), 1.24–1.64 (20H, m), 0.88 (3H, t, J=7.3 Hz).

(v) Synthesis of compound A6

To the mesylated product (compound A5, 0.86 g) were added dimethylformamide (10 ml) and sodium azide (885 mg), and the mixture was stirred at 120° C for 15 hours. The reaction mixture was diluted with brine, extracted with ethyl acetate (three times), and then concentrated. Purification on a silica gel column (Wako Gel C-200, 30 g) eluting with hexane-ethyl acetate (40:1) afforded an azide (compound A6) in an amount of 0.73 g (yield, 94.3%). Data of the compound A6 MS: FDMS 453. NMR: $^1$H (500 MHz, CDCl$_3$; 27° C.)

δ (ppm) 7.27–7.44 (10H, m), 4.54 & 4.58 (2H, ABq, J=12.2 Hz), 4.52 & 4.57 (2H, ABq, J=11.0 Hz), 3.68–3.70 (2H, m), 3.63 (1H, dd, J=8.5, 11.0 Hz), 3.53 (1H, dt, J=4.3, 8.6 Hz), 1.25–1.64 (20H, m), 0.88 (3H, t, J=6.7 Hz).

(vi) Synthesis of the compound A7

To the azide (compound A6, 0.72 g) were added tetrahydrofuran (7 ml) and 10% palladium on charcoal (70 mg), and the mixture was stirred at room temperature after the reaction vessel was purged with hydrogen. The reaction mixture was filtered through celite, and the filtrate was concentrated. Purification on a silica gel column (Wako Gel C-200, 15 g) eluting with hexane-acetone (6:1) afforded an amine (compound A7) in an amount of 0.62 g (yield, 91.5%). Data of the compound A7 MS: FDMS 427. NMR: $^1$H (500 MHz, CDCl$_3$; 27° C.)

δ (ppm) 7.27–7.36 (10H, m), 4.51 & 4.54 (2H, ABq, J=11.6 Hz), 4.52 (2H, s), 3.58 (1H, dd, J=3.7, 9.2 Hz), 3.41–3.45 (2H, m), 3.20 (1H, dt, J=4.3, 7.3 Hz), 1.26–1.63 (20H, m), 0.88 (3H, t, J=6.7 Hz).

(vii) Synthesis of the compound A8

To the amine (compound A7, 0.61 g) were added methylene chloride (20 ml), 2-chloro-1-methylpyridinium iodide (483 mg) and n-tributylamine (0.45 ml). Tetracosanic acid (597 mg) was further added, and the mixture was heated under reflux for 2 hours. The reaction mixture was cooled to room temperature, washed sequentially with 5% aqueous sodium thiosulfate solution, 5% aqueous sodium hydrogen carbonate solution and brine, and then concentrated. Purification on silica gel column (Wako Gel C-200, 20 g) eluting with hexane-acetone (20:1) afforded an amide (compound A8) in an amount of 0.56 g (yield, 51.2%). Data of the compound A8 MS: FDMS 777. NMR: $^1$H (500 MHz, CDCl$_3$; 27° C.)

δ (ppm) 7.28–7.35 (10H, m), 5.66. (1H, d, J=9.2 Hz), 4.45 & 4.58 (2H, ABq, J=11.6 Hz), 4.48 (2H, s), 4.25–4.30 (1H, m), 3.73 (1H, dd, J=4.9, 9.8 Hz), 3.57 (1H, dt, J=5.5, 6.7 Hz), 3.52 (1H, dd, J=4.3, 9.8 Hz), 2.08 (2H, dt, J=3.1, 10.4 Hz), 1.26–1.58 (64H, m), 0.88 (6H, t, J=6.7 Hz).

(viii) Synthesis of the compound A9

To the amide (compound A8, 0.55 g) were added tetrahydrofuran (15 ml) and palladium black (55 mg). The reaction vessel was purged with hydrogen, and the mixture was stirred at room temperature for 16 hours. The reaction mixture was filtered through celite, and the filtrate was concentrated. Purification on a silica gel column (Wako Gel C-200, 20 g) eluting with chloroform-methanol (20:1) afforded a diol (compound A9) in an amount of 302 mg (yield, 71.6%). Data of the compound A9 MS: FDMS 597. NMR: $^1$H (500 MHz, C$_5$D$_5$N; 27° C.)

δ (ppm) 8.34 (1H, d, J=7.9 Hz), 4.62–4.67 (1H, m), 4.46 (1H, dd, J=4.9, 11.0 Hz), 4.30 (1H, dd, J=5.8, 11.6 Hz), 4.25–4.32 (1H, m), 2.48 (2H, dt, J=2.4, 7.3 Hz), 1.23–1.97 (62H, m), 0.88 (6H, t, J=6.7 Hz).

(ix) Synthesis of the compound A10

To the diol (compound A9, 70 mg) were added pyridine (5 ml), triphenylmethyl chloride (261 mg) and 4-dimethylaminopyridine (5 mg), and the mixture was stirred at 60° C. for 2 hours. The reaction mixture was diluted with chloroform, washed with brine and concentrated. Purification on a silica gel column (Wako Gel C-200, 10 g) eluting with chloroform-acetone (100:1) afforded a tritylated derivative (compound A10) in an amount of 90.2 mg (yield, 91.6%). Data of the compound A10 MS: FDMS 837. NMR: $^1$H (500 MHz, CDCl$_3$; 27° C.)

δ (ppm) 7.25–7.47 (15H, m), 6.28 (1H, d, J=7.9 Hz), 3.93–3.96 (1H, m), 3.58–3.61 (1H, m), 3.52 (1H, dd, J=3.1, 9.8 Hz), 3.26 (1H, dd, J=3.7, 9.8 Hz), 2.95 (1H, d, J=9.2 Hz), 2.24 (2H, t, J=7.3 Hz), 1.25–1.70 (62H, m), 0.88 (6H, t, J=7.3 Hz).

(x) Synthesis of the compound A11

To the trityl derivative (compound A10, 87 mg) in pyridine (3.0 ml) were added benzoyl chloride (24 μl) and 4-dimethylaminopyridine (3 mg), and the mixture was stirred for 4 hours. After the mixture to which ice-water had been added was stirred for 30 minutes, it was diluted with chloroform, washed with water and concentrated. Purification on a silica gel column (Wako Gel C-200, 10 g) eluting with hexane-ethyl acetate (10:1) afforded a benzoyl derivative (compound A11) in an amount of 83.4 mg (yield, 85.3%). Data of the compound A11 MS: FDMS 941. NMR: $^1$H (500 MHz, CDCl$_3$; 27° C.)

δ (ppm) 7.16–7.93 (20H, m), 5.74 (1H, d, J=9.2 Hz), 5.34–5.37 (1H, m), 4.39–4.48 (1H, m), 3.40 (1H, dd, J=3.7, 9.8 Hz), 3.19 (1H, dd, J=3.7, 9.8 Hz), 2.09 (2H, dt, J=2.5, 9.8 Hz), 1.25–1.74 (64H, m), 0.88 & 0.87 (each 3H, t, J=7.3 Hz).

(xi) Synthesis of the compound A12

To the benzoyl derivative (compound A11, 80 mg) were added methylene chloride (1.0 ml) and methanol (0.5 ml). p-Toluenesulfonic acid monohydrate (20 mg) was added, and the mixture was stirred at room temperature for 2 hours. The reaction mixture was diluted with ethyl acetate, washed with a 5% aqueous sodium hydrogen carbonate and brine, and then concentrated. Purification on a silica gel column (Wako Gel C-200, 5 g) eluting with hexane-ethyl acetate (2:1) afforded an alcohol (compound A12) in an amount of 58 mg (yield, 93.6%). Data of the compound A12 MS: FDMS 701. NMR: $^1$H (500 MHz, CDCl$_3$; 27° C.)

δ (ppm) 7.46–8.06 (5H, m), 6.25 (1H, d, J=8.5 Hz), 5.06–5.09 (1H, m), 4.15–4.19 (1H, m), 3.58–3.68 (2H, m), 2.23 (2H, t, J=6.7 Hz), 1.22–1.77 (62H, m), 0.88 & 0.87 (each 3H, t, J=7.3 Hz).

(xii) Synthesis of the compound A14

A solution of the alcohol (compound A12, 58 mg) in tetrahydrofuran (3.0 ml) was stirred with stannous chloride (37 mg), silver perchlorate (41 mg) and Molecular Sieves 4A powder (300 mg). After stirring for 30 minutes, the mixture was cooled to −10° C., and a solution of benzyl galactosyl fluoride (compound A13, 68 mg) in tetrahydrofuran (1.5 ml) was added. The mixture was allowed to warm gradually to room temperature, stirred for 2 hours and filtered through celite. The filtrate was concentrated. Purification on a silica gel column (Wako Gel C-200, 5 g) eluting with hexane-ethyl acetate (5:1) afforded an α-galactoside (compound A14) in an amount of 62.6 mg (yield, 61.8%). Data of the compound A14 MS: FDMS 1224. NMR: $^1$H (500 MHz, CDCl$_3$; 27° C.)

δ (ppm) 8.02 (2H, d, J=7.3 Hz), 7.56 (1H, t, J=7.9 Hz), 7.43 (2H, t, J=7.9 Hz), 7.23–7.39 (20H, m), 6.58 (1H, d, J=9.2 Hz), 5.30 (1H, dt, J=3.7, 7.9 Hz), 4.90 & 4.55 (2H, ABq, J=11.6 Hz), 4.77 & 4.69 (2H, ABq, J=11.6 Hz), 4.75 (1H, d, J=3.7 Hz), 4.73 & 4.65 (2H, ABq, J=12.2 Hz), 4.47 & 4.38 (2H, ABq, J=12.2 Hz), 4.30–4.34 (1H, m), 4.10–4.12 (1H, m), 4.01 (1H, dd, J=3.7, 9.8 Hz), 3.97 (1H, dd, J=3.7, 12.2 Hz), 3.84–3.93 (2H, m), 3.57 (1H, dd, J=3.1, 12.2 Hz), 3.52 (1H, dd, J=7.3, 9.2 Hz), 3.29 (1H, dd, J=4.3, 9.8 Hz), 1.98–2.09 (2H, m), 1.18–1.68 (62H, m), 0.88 (3H, t, J=6.7 Hz), 0.86 (3H, t, J=7.3 Hz).

(xiii) Synthesis of the compound A15

To the α-galactoside (compound A14, 56 mg) were added tetrahydrofuran (4.0 ml) and palladium black (15 mg), and the mixture was stirred at room temperature for 16 hours after the reaction vessel was purged with hydrogen. The reaction mixture was filtered through celite, concentrated and purified on a silica gel column (Wako Gel C-200, 2 g) eluting with chloroform-methanol (20:1) to give a tetraol (compound A15) in an amount of 37.4 mg (yield, 94.7%). Data of the compound A15 MS: FDMS 863. NMR: $^1$H (500 MHz, CDCl$_3$; 27° C.)

δ (ppm) 8.04 (2H, d, J=7.9 Hz), 7.62 (1H, t, J=7.9 Hz), 7.48 (2H, t, J=7.3 Hz), 6.16 (1H, d, J=9.2 Hz), 5.21–5.24 (1H, m), 4.81 (1H, d, J=2.4 Hz), 4.45–4.46 (1H, m), 4.08 (1H, bs), 3.91–3.94 (1H, m), 3.87 (1H, dd, J=2.4, 10.4 Hz), 3.75–3.85 (4H, m), 3.57 (1H, dd, J=5.5, 11.6 Hz), 2.22 (2H, dt, J=1.8, 7.3 Hz), 1.22–1.79 (62H, m), 0.88 (3H, t, J=7.3 Hz), 0.87 (3H, t, J=6.7 Hz).

(xiv) Synthesis of the compound 9

To the tetraol (compound A15, 36.0 mg) were added methanol (3 ml) and a 1N methanolic sodium methoxide solution (0.3 ml), and the mixture was stirred for 2 hours. The mixture was neutralized with resins (Dowex 50W, X8; manufactured by The Dow Chemical Company), and then filtered. The solids removed was washed sufficiently with chloroform-methanol (1:1), and the extract was combined with the filtrate, and then concentrated. Purification on a silica gel column (Wako Gel C-200, 2 g) eluting with chloroform-methanol (10:1) afforded the compound 9 in an amount of 29.7 mg (yield, 94.0%). Data of the compound 9 $[\alpha]^{23}_D$=+49.0° (pyridine, c=1.31) MS: FDMS 759. IR: (cm$^{-1}$, KBr) 3200, 2870, 2800, 1630, 1530, 1450, 1080. mp: 151°–155° C. NMR: $^1$H (500 MHz, C$_5$D$_5$N; 27° C.)

δ (ppm) 8.49 (1H, d, J=8.6 Hz), 6.11–6.52 (5H, m), 5.45 (1H, d, J=3.7 Hz), 4.73 (1H, m), 4.65 (1H, dd, J=3.8, 10.4 Hz), 4.53–4.57 (2H, m), 4.43–4.49 (4H, m), 4.36 (1H, dd, J=5.5, 10.4 Hz), 4.27 (1H, m), 2.47 (2H, t, J=6.7 Hz), 1.83–1.91 (4H, m), 1.23–1.56 (58H, m), 0.88 (6H, t, J-7.3 Hz).

$^{13}$C (125 MHz, C$_5$D$_5$N; 27° C.)

δ (ppm) 173.4 (s), 102.1 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 14.3 (q).

(2) Synthetic route B

While this scheme specifically illustrates the synthetic routes of the aforementioned compounds 7 and 5, the compounds according to the present invention (1–4, 6, 8–14) can also be synthesized by applying this method. [Synthesis of the compound 7 (FIG. 6)]

Abbreviations in the aforementioned scheme are the same as those in the previously described scheme. (i) Synthesis of the compound B1

To tetradecanetriphenylphosphonium bromide (213.7 g) was added tetrahydrofuran (630 ml), and the reaction vessel was purged with argon. A 2.3N solution of n-butyl lithium in hexane (173 ml) was added at –30° C., and the mixture was stirred for 3.5 hours. A (2R,3R) -aldehyde (compound A2, 31.73 g) dissolved in tetrahydrofuran (630 ml) was added dropwise, and the mixture was stirred for 2 hours and then concentrated. The residue was diluted with ethyl acetate, washed with water and brine, and then concentrated. Purification on a silica gel column (Wako Gel C-200, 850 g) eluting with hexane-ethyl acetate (9:1) afforded an alcohol (compound B1) in an amount of 36.31 g (yield, 79.0%). Data of the compound B1 MS: FDMS 481. NMR: $^1$H (500 MHz, CDCl$_3$; 27° C.)

δ (ppm) 7.26–7.46 (1OH, m), 5.69–5.78 (1H, m), 5.31–5.38 (1H, m), 4.34–4.63 (5H, m), 4.28 (0.7H, dd, J=6.7, 9.2 Hz), 3.85 (0.3H, t, J=7.3 Hz), 3.75–3.78 (1H, m), 3.56–3.60 (1H, m), 3.47 (1H, dd, J=5.5, 10.4 Hz), 1.98–2.11 (2H, m), 1.26–1.34 (22H, m), 0.88 (3H, t, J=6.7 Hz).

(ii) Synthesis of the compound B2

To a solution of the alcohol (compound B1, 5.03 g) in pyridine (50 ml) was added methanesulfonyl chloride (1.62 ml), and the mixture was stirred at room temperature for 16 hours. The mixture was concentrated and a residual acid chloride was distilled azeotropically together with toluene. The residue was diluted with diethyl ether, washed with brine, and then concentrated. Purification on a silica gel column (Wako Gel C-200, 200 g) eluting with hexane-acetone (10:1) afforded a mesyl derivative (compound B2) in an amount of 5.20 g (yield, 88.9%).

Data of the compound B2 MS: FDMS 558. MR: $^1$H (500 MHz, CDCl$_3$; 27° C.)

δ (pPm) 7.23–7.35 (1OH, m), 5.77–5.83 (1H, m), 5.26–5.35 (1H, m), 4.71–4.77 (1H, m), 4.33–4.62 (5H, m), 4.06 (0.3H, t, J=8.1 Hz), 3.74 (0.7H, dd, J=3.1, 11.0 Hz), 3.65–3.70 (1H, m), 2.964 (0.9H, s), 2.956 (2.1H, s), 1.99–2.17 (2H, m), 1.26–1.37 (22H, m), 0.88 (3H, t, J=6.8 Hz).

(iii) Synthesis of the compound B3

To the mesyl derivative (compound B2, 1.52 g) were added dimethylformamide (20 ml) and sodium azide (1.42 g). After stirring at 120° C. for 12 hours, the mixture was diluted with brine, extracted with ethyl acetate (three times), and then concentrated. Purification on a silica gel column (Wako Gel C-200, 50 g) eluting with hexane-ethyl acetate (40:1) afforded an azide derivative (compound B3) in an amount of 1.07 g (yield, 77.7%). Data of the compound B3 IR: (cm-$^1$, KBr) 2870, 2810, 2050, 1490, 1440. NMR: $^1$H (500 MHz, CDCl$_3$; 27° C.)

δ (ppm) 7.25–7.35 (1OH, m), 5.69–5.82 (1H, m), 5.35–5.43 (1H, m), 4.30–4.74 (4H, m), 3.89 (0.3H, dd, J=5.5, 8.5 Hz), 3.55–3.70 (3.7H, m), 1.97–2.10 (2H, m), 1.25–1.36 (22H, m), 0.88 (3H, t, J=6.8 Hz).

(iv) Synthesis of the compound B5

To a solution of the azide (compound B3, 0.45 g) in tetrahydrofuran (10 ml) were added a 10% methanolic hydrochloric acid solution (2 ml) and palladium black (0.25 g). After the reaction vessel was purged with hydrogen, the mixture was stirred at room temperature for 12 hours, and then filtered through celite. The filtrate was concentrated to give a white powdery amine (compound B4, 301 mg). Tetrahydrofuran (10 ml), p-nitrophenyl octanoate (260 mg) and triethylamine (0.15 ml) were added to the amine, the mixture was stirred at 60° C. for 12 ours. The reaction mixture was concentrated to give a yrup. Purification of the syrup on a silica gel column (Wako Gel C-200, 50 g) eluting with chloroform-methanol (20:1) afforded an amide derivative (compound B5) in an amount of 166 mg (yield based on the compound B3, 43.6%). Data of the compound B5 MS: FDMS 429. NMR: $^1$H (500 MHz, C$_5$D$_5$N; 27° C.)

δ (ppm) 8.37 (1H, d, J=7.9.Hz), 4.63–4.69 (1H, m), 4.44–4.49 (1H, m), 4.25–4.35 (2H, m), 2.46 (2H, dt, J=3.1, 7.9 Hz), 1.78–1.95 (4H, m), 1.16–1.59 (34H, m), 0.87 & 0.82 (each 3H, t, J=6.7 Hz).

(v) Synthesis of the compound B6

To a solution of the amide (compound B5, 48 mg) in tetrahydrofuran (1.0 ml) were added stannous chloride (75 mg), silver perchlorate (82 mg) and powdery Molecular Sieves 4A (200 mg), and the mixture was stirred for 30 minutes. The mixture was cooled to −10° C., and a solution of benzylgalactosyl fluoride (compound A13, 67 mg) in tetrahydrofuran (2.0 ml) was added thereto. The mixture was allowed to warm gradually to room temperature, stirred for 2 hours, and then filtered through celite. The solids removed were washed with a small amount of acetone and combined with the filtrate, and then concentrated. Purification on a silica gel column (Wako Gel C-200, 5 g), eluting with hexane-ethyl acetate (3:1), produced a crude α-galactoside (compound B6), which was subjected to the subsequent reaction.

(vi) Synthesis of the compound 7

To a solution of the α-galactoside (compound B6, 47 mg) in ethyl acetate (1.5 ml) was added palladium black (15 mg). After the reaction vessel was purged with hydrogen, the mixture was stirred at room temperature for 16 hours. The mixture was filtered through celite, and the filtrate was concentrated. Purification on a silica gel column (Wako Gel C-200, 2g),eluting with chloroform-methanol (10:1), produced the compound 7 in an amount of 25.1 mg (yield based on the compound B5, 37.9%). Data of the compound 7 $[\alpha]^{23}_D$=+58.20 (pyridine, $c$=0.56) MS: FDMS 591. IR: ($cm^{-1}$, KBr) 3300, 2870, 2810, 1640, 1535, 1460, 1060. mp: 155°–157° C. NMR: $^1H$ (500 MHz, $C_5D_5N$; 27° C.)

δ (ppm) 8.49 (1H, d, J=8.6 Hz), 6.52 (2H, m), 6.42 (1H, m), 6.33 (1H, bs), 6.12 (1H, bd, J=6.7 Hz), 5.46 (1H, d, 15 J=3.7 Hz), 4.73 (1H, m), 4.65 (1H, m), 4.53–4.57 (2H, m), 4.40–4.49 (5H, m), 4.36 (1H, dd, J=5.5, 10.4 Hz), 4.27 (1H, m), 2.45 (2H, dt, J=5.5, 7.9 Hz), 1.80–1.92 (4H, m), 1.18–1.58 (34H, m), 0.87 & 0.81 (each 3H, t, J=6.7 Hz).

$^{13}C$ (125 MHz, $C_5D_5N$; 27° C.)

δ (ppm) 173.4 (s), 102.2 (d), 73.1 (d), 72.0 (d), 71.7 (d), 71.0 (d), 70.8 (d), 70.5 (d), 69.7 (t), 62.7 (t), 54.9 (d), 36.8 (t), 35.1 (t), 32.1 (t), 31.9 (t), 25 30.2 (t), 30.1 (t), 30.0 (t), 29.9 (t), 29.64 (t), 29.61 (t), 29.4 (t), 26.6 (t), 26.4 (t), 22.93 (t), 22.86 (t), 14.3 (q), 14.2 (q).

[Synthesis of the compound 5 (FIG. 7)]

Abbreviations in the above scheme are the same as those in the previously described scheme.

(i) Synthesis of the compound B7

To a solution of the azide (compound B3, 3.9 g) in ethyl acetate (50 ml) was added 10% palladium on charcoal (1.2 g). After the reaction vessel was purged with hydrogen, the mixture was stirred at room temperature for 16 hours. The catalyst was filtered off, and the filtrate was concentrated and purified on a silica gel column (Wako Gel C-200, 300 g, hexane-acetone (6:1)) to give an amine, (compound B7) in an amount of 3.22 g (yield, 86.7%). MS: FDMS 480. NMR: $^1H$ (500 MHz, $CDCl_3$; 27° C.)

δ (ppm) 7.24–7.35 (1OH, m), 5.79 (0.7H, dt, J=7.3, 11.6 Hz), 5.71 (0.3 H, dt, J=6.7, 15.3 Hz), 5.34–5.41 (1H, m), 4.30–4.58 (4H, m), 4.17 (0.7H, dd, J=6.7, 9.8 Hz), 3.72 (0.3H, dd, J=6.7, 8.5 Hz), 3.42–3.66 (2H, m), 3.06–3.10 (1H, m), 2.01–2.14 (2H, m), 1.26–1.50 (22H, m), 0.88 (3H, t, J=6.7.Hz).

(ii) Synthesis of the compound B8

To a solution of the amine (compound B7, 2.22 g) in methylene chloride (50 ml), 2-chloro-1-methylpyridinium iodide (1.88 g) were added n-tributylamine (1.75 ml) and myristic acid (1.47 g), and the mixture was heated under reflux and stirred for 2 hours. The reaction mixture was washed sequentially with a 5% aqueous sodium thiosulfate solution and brine, and then concentrated. Purification on a silica gel column (Wako Gel C-200, 100 g) eluting with chloroform-acetone (200:1), produced an amide (compound B8) in an amount of 2.41 g (yield, 75.6%). MS: FDMS 691. NMR: $^1H$ (500 MHz, $CDCl_3$; 27° C.)

δ (ppm) 7.26–7.32 (1OH, m), 5.64–5.73 (2H, m), 5.33–5.41 (1H, m), 4.19–4.59 (6H, m), 3.79–3.89 (1H, m), 3.51–3.58 (1H, m), 1.98–2.13 (2H, m), 1.26–1.58 (46H, m), 0.88 (6H, t, J=6.7 Hz).

(iii) Synthesis of the compound B9

To the amide (compound B8, 3.50 g) were added 1-propanol (15 ml), tetrahydrofuran (15 ml), 10% palladium on charcoal (1.2 g) and formic acid (3.0 ml). The mixture was stirred at 45° C. for 16 hours in a nitrogen atmosphere. The catalyst was removed by filtration, and the filtrate was concentrated. Crystallization of the residue from chloroform-acetone produced a ceramide (compound B9) in an amount of 2.08 g (yield, 80.4%). $[\alpha]^{24}_D$=+3.50 (pyridine, $c$=1.87) MS: FDMS 513. mp: 104°–105° C. NMR: $^1H$ (500 MHz, $C_5D_5N$; 27° C.)

δ (ppm) 8.35 (1H, d, J=9.2 Hz), 6.36 (1H, t, J=4.9 Hz), 6.24 (1H, d, J=6.1 Hz), 4.62–4.67 (1H, m), 4.46 (1H, dt, J=4.9, 11.0 Hz), 4.25–4.33 (2H, m), 2.47 (2H, dt, J=1.8, 7.3 Hz), 1.25–1.95 (50H, m), 0.88 (6H, t, J=6.7 Hz).

(iv) Synthesis of the compound B10

To a solution of the ceramide (compound B9, 1.0 g) in tetrahydrofuran, (30 ml) were added stannous chloride (1.29 g), silver perchlorate (1.41 g) and powdery Molecular Sieves 4A (1.5 g), and the mixture was stirred for 30 minutes. The mixture was cooled to −10° C., and a solution of benzylgalactosyl fluoride (compound A13, 1.11 g) in tetrahydrofuran (10 ml) was added. The resulting mixture was allowed to warm gradually to room temperature, stirred for 2 hours, and then filtered through celite. The solids removed were washed with a small amount of acetone, and the extract was combined with the filtrate, and then concentrated and purified on a silica gel column (Wako Gel C-200, 150 g, hexane-ethyl acetate (3:1)) to give an α-galactoside (compound B10) in an amount of 646 mg (yield, 32.0%). MS: FDMS 1035. NMR: $^1H$ (500 MHz, $CDCl_3$; 27° C.)

δ (ppm) 7.23–7.37 (20H, m), 6.49 (1H, d, J=7.9 Hz), 4.92 (1H, d, J=11.3 Hz), 4.84 (1H, d, J=12.2 Hz), 4.73–4.78 (3H, m), 4.67 (1H, d, J=11.6 Hz), 4.46 (1H, d, J=11.6 Hz), 4.37 (1H, d, J=11.6 Hz), 4.03 (1H, dd, J=3.7, 9.8 Hz), 3.96 (1H, bs), 3.83–3.92 (4H, m), 3.70 (1H, dd, J=3.1, 10.4 Hz), 3.47–3.58 (3H, m), 3.40 (1H, d, J=9.8 Hz), 2.12 (2H, dt, J=1.8, 7.9 Hz), 1.25–1.61 (51H, m), 0.88 (6H, t, J=6.7 Hz).

(v) Synthesis of the compound 5

To a solution of the galactoside (compound B10, 1.59 g) in tetrahydrofuran (30 ml) was added palladium black (290 mg). After the reaction vessel was purged with hydrogen, the mixture was stirred at room temperature for 16 hours. The catalyst was removed by filtration, and the filtrate was concentrated. Purification on a silica gel column (Wako Gel C-200, 100 g), eluting with chloroform-methanol (5:1), produced the compound 5 in an amount of 984 mg (yield, 95.0 %). Data of the compound 5 $[\alpha]^{24}_D$=+57.80 (pyridine, $c$=1.69) MS: FDMS 674. IR: ($cm^{-1}$, KBr) 3400, 3270, 2920, 2850, 1640, 1550, 1465, 1135, 1075, 1045. mp: 159.0°–161.0° C., NMR: $^1H$ (500 MHz, $C_5D_5N$; 27° C.)

δ (ppm) 8.52 (1H, d, J=8.6 Hz), 6.51 (1H, m), 6.44 (1H, m), 6.33 (1H, m), 6.15 (1H, m), 5.45 (1H, d, J=3.7 Hz), 4.73 (1H, m), 4.65 (1H, m), 4.40–4.58 (6H, m), 4.36 (1H, dd, J=5.5, 10.0 Hz), 4.28 (1H, m), 2.48 (2H, t, J=7.0 Hz), 1.80–1.95 (4H, m), 1.57 (1H, m), 1.18–1.43 (49H, m), 0.88 (6H, t, J=6.7 Hz). $^{13}C$ (125 MHz, $C_5D_5N$; 27° C.)

δ (ppm) 173.4 (s), 102.2 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.02 (t), 29.97 (t), 29.91 (t), 29.87 (t), 29.8 (t), 29.7 (t), 29.6 (t), 26.6 (t), 26.4 (t), 22.9 (t), 14.3 (q).

(3) Synthetic route C

A specific synthetic route with the use of a sphingosine can be illustrated by the following reaction route scheme. While the reaction route scheme is illustrated specifically with reference to the aforementioned compounds 1 and 5, the compounds (2–4, 6–8, 14) according to the present invention can also be synthesized by applying this method. Furthermore, the compounds 15 and 35 having a double bond can be synthesized by conducting deprotection with the use of liquid ammonia and metallic sodium. [Synthesis of the compound 1 (FIG. 8)]

Abbreviations in the above scheme are the same as those in the previously described schemes.

(i) Synthesis of the compound C2

To a solution of sphingosine (25 mg) in tetrahydrofuran (1 ml) were added p-nitrophenyl tetracosanate (81.8 mg) and 4-dimethylaminopyridine (2.5 mg), and the mixture was stirred at 40° C for 12 hours. The mixture was evaporated under reduced pressure. Purification on a silica gel column (Wako Gel C-200, 10 g), eluting with chloroform-methanol (4:1), produced an amide (compound C2) in an amount of 23.2 mg (yield, 42.7%). Data of the compound C2 $[\alpha]^{23}_D= -11.3°$ (pyridine, $c$=1.03) MS: FDMS 651. IR: (cm$^{-1}$, KBr) 3280, 2910, 2840, 1635, 1540, 1465. mp: 87.5°–89.5° C. NMR: $^1$H (500 MHz, CDCl$_3$+CD$_3$OD (1drop); 27° C.)

δ (ppm) 5.76 (1H, dt, J=6.7, 15.3 Hz), 5.49 (1H, dd, J=6.7, 15.3 Hz), 4.24 (1H, bs), 3.82–3.91 (2H, m), 3.67 (1H, m), 2.21 (2H, t, J=7.6 Hz), 1.9–2.1 (2H, m), 1.62 (2H, m), 1.2–1.4 (62H, m), 0.88 (6H, t, J=6.7 Hz).

(ii) Synthesis of the compound C3

To a solution of the amide (compound C2, 33.8 mg) in tetrahydrofuran (1.5 ml) were added stannous chloride (33 mg), silver perchlorate (36 mg) and powdered Molecular Sieves 4A (140 mg), and the mixture was stirred for 30 minutes. The mixture was next cooled to −10° C., a solution of benzylgalactosyl fluoride (compound A13, 28 mg) in tetrahydrofuran (0.5 ml) was added to it. The resulting mixture was allowed to gradually warm to room temperature. After being stirred for 3 hours, the mixture was diluted with acetone and filtered through celite, and the filtrate was evaporated under reduced pressure. Purification on a silica gel column (Wako Gel C-200, 10 g) eluting with hexane-ethyl acetate (3:1), produced an α-galactoside (compound C3) in an amount of 19.7 mg (yield, 32.4%). Data of the compound C3 $[\alpha]^{23}_D$=+25.10 (CHCl$_3$, $c$=0.47) MS: FDMS 1173. IR: (cm$^{-1}$, KBr) 3210, 2920, 2850, 1640, 1590, 1545, 1495, 1465, 1450, 1335, 1290, 1110. mp: 63.0°–64.5° C. NMR: $^1$H (500 MHz, CDCl$_3$; 27° C.)

δ (ppm) 7.23–7.37 (20H, m), 6.40 (1H, d, J=7.9 Hz), 5.65 (1H, m), 5.42 (1H, dd, J=6.1, 15.3 Hz), 4.91, 4.85, 4.70, 4.55, 4.47 & 4.38 (each 1H, d, J=11.6 Hz), 4.75 (2H, s), 4.12 (1H, m), 3.95–4.06 (3H, m), 3.79–3.92 (3H, m), 3.4–3.71 (3H, m), 2.12 (2H, dt, J=3.4, 7.6 Hz), 1.90–2.01 (3H, m), 1.1–1.6 (63H, m), 0.88 (6H, t, J=6.7 Hz).

(iii) Synthesis of the compound 1

To a solution of the α-galactoside (compound C3, 9.7 mg) in tetrahydrofuran (1.0 ml) was added a 5% palladium on barium sulfate (5 mg). After the reaction vessel was purged with hydrogen, the mixture was stirred at room temperature for 16 hours, and then filtered through celite. The filtrate was concentrated and purified on a silica gel column (Wako Gel C-200, 10 g, chloroform-methanol (10:1)) to give the compound 1 in an amount of 3.0 mg (yield, 44.5 mg). Data of the compound 1 $[\alpha]^{23}_D$=+50.00 (pyridine, $c$=0.26) MS: FDMS 814. IR: (cm$^{-1}$, KBr) 3260, 2910, 2850, 1645, 1545, 1470, 1350, 1125, 1065. mp: 184.5°–186.5° C. NMR: $^1$H (500 MHz, C$_5$D$_5$N; 27° C.)

δ (ppm) 8.52 (1H, d, J=8.6 Hz), 5.46 (1H, d, J=3.7 Hz), 4.74 (1H, m), 4.66 (1H, dd, J=3.6, 9.8 Hz), 4.54–4.60 (2H, m), 4.40–4.52 (4H, m), 4.37 (1H, dd, J=5.5, 10.4 Hz), 4.29 (1H, m), 2.48 (2H, t, J=7.3 Hz), 1.8–2.0 (4H, m), 1.58 (1H, m), 1.20–1.45 (65H, m), 0.881 & 0.877 (each 3H, t, J=7.3 Hz). $^{13}$C (125 MHz, C$_5$D$_5$N; 27° C.)

δ (ppm) 173.4 (s), 102.2 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.83 (t), 29.76 (t), 29.6 (t), 26.6 (t), 26.4 (t), 22.9 (t), 14.3 (q). [Synthesis of the compound 5 (FIG. 9)]

Abbreviations in the above scheme are the same as those in the previously described schemes.

(i) Synthesis of the compound C4

To a solution of sphingosine (75 mg) in tetrahydrofuran (1.5 ml) were added p-nitrophenyl myristate (175 mg) and 4-dimethylaminopyridine (7.6 mg), and the mixture was stirred at 46° C. for 12 hours. The reaction mixture was concentrated directly and purified on a silica gel column (Wako Gel C-200, 10 g, hexane- acetone (3:1)) to give an amide (compound C4) in an amount of 112.6 mg (yield, 88.3%). Data of the compound C4 $[\alpha]^{23}_D$=−11.40° (pyridine, $c$=0.58) MS: FDMS 510. IR: (cm$^{-1}$, KBr) 3300, 2910, 2850, 1640, 1620, 1550, 1470, 1380, 1265, 1240, 1040. mp: 96.5°–98.0° C. NMR: $^1$H (500 MHz, C$_5$D$_5$N; 27° C.) δ (ppm) 8.33 (1H, d, J=8.5 Hz), 6.7 (1H, m), 6.05 (1H, dd, J=6.4, 15.9 Hz), 5.96 (1H, dt, J=6.4, 15.9 Hz), 4.85 (1H, t, J=6.7 Hz), 4.75 (1H, m), 4.47 (1H, dd, J=4.9, 11.0 Hz), 4.30 (1H, dd, J=4.0, 10.7 Hz), 2.47 (2H, t, J=7.6 Hz), 2.10 (2H, m), 1.85 (2H, m), 1.39 (4H, m), 1.20–1.33 (38H, m), 0.88 (6H, t, J=6.7 Hz). $^{13}$C (125 MHz, C$_5$D$_5$N; 27° C.)

δ (ppm) 173.5 (s), 132.4 (d), 132.3 (d), 73.3 (d), 62.2 (t), 56.9 (d), 36.9 (t), 32.7 (t), 32.1 (t), 29.99 (t), 29.96 (t), 29.93 (t), 29.87 (t), 29.8 (t), 29.7 (t), 29.61 (t), 29.55 (d), 26.4 (t), 22.9 (t), 14.3 (q).

(ii) Synthesis of the compound C5

To a solution of the amide (compound C4, 106.8 mg) in tetrahydrofuran (4.5 ml) was added a powdered Molecular Sieves 4A (400 mg), and the mixture was stirred for 10 minutes. Stannous chloride (133 mg) and silver perchlorate (146 mg) were added, and the mixture was further stirred for 30 minutes. The reaction mixture was cooled to −10° C., and a solution of benzylgalactosyl fluoride (compound A13, 113 mg) in tetrahydrofuran (1.5 ml) was added thereto. After 30 minutes, it was allowed to warm to room temperature, stirred for 30 minutes, then diluted with chloroform-methanol (1:1) and filtered through celite, and the filtrate was evaporated under reduced pressure. Purification of the residue on a silica gel column (Wako Gel C-200, 15 g), eluting with hexane-ethyl acetate (5:2), produced an α-galactoside (compound C5) in an amount of 76.0 mg (yield, 35.2%). Data of the compound C5 $[\alpha]^{24}_D$=+32.70 (CHCl$_3$, $c$=2.26) MS: FDMS 1033. IR: (cm$^{-1}$, KBr) 3320, 2920, 2850, 1640, 1615, 1545, 1465, 1450, 1350, 1105, 1045. mp: 66.0°–68.0° C. NMR: $^1$H (500 MHz, CDCl$_3$; 27° C.) (ppm) 7.25–7.37 (20H, m), 6.40 (1H, d, J=7.9 Hz), 5.66 (1H, dt, J=7.9, 15.3 Hz), 5.42 (1H, dd, J=5.5, 15.3 Hz), 4.91, 4.85, 4.70, 4.55, 4.47 & 4.38 (each 1H, d, J=11.6 Hz), 4.752 (2H, s), 4.747 (1H, d, J=4.9 Hz), 4.13 (1H, m), 4.03 (1H, dd, J=3.7, 10.4 Hz), 3.95–4.01 (2H, m), 3.79–3.89 (4H, m), 3.69 (1H, dd, J=3.7, 10.3 Hz), 3.45–3.55 (2H, m), 2.12 (2H, dt, J=3.7, 7.9 Hz), 1.99 (2H, m), 1.58 (2H, m), 1.2–1.4 (42H, m), 0.88 (6H, t, J=7.0 Hz). $^{13}$C (125 MHz, CDCl$_3$; 27° C.)

δ (ppm) 173.3 (s), 138.5 (s), 138.4 (s), 138.0 (s), 137.6 (s), 133.0 (d), 129.2 (d), 128.44 (d), 128.41 (d), 128.3 (d), 128.13 (d), 128.10 (d), 127.90 (d), 127.86 (d), 127.6 (d), 127.4 (d), 126.1 (d), 99.1 (d), 79.2 (d), 75.9 (d), 74.8 (t), 74.4 (d), 74.2 (t), 74.0 (d), 73.6 (t), 72.7 (t), 69.8 (d), 69.0 (t), 68.7 (t), 52.8 (d), 36.7 (t), 32.3 (t), 31.9 (t), 29.68 (t), 29.65 (t), 29.5 (t), 29.41 (t), 29.36 (t), 29.32 (t), 29.26 (t), 25.8 (t), 22.7 (t), 14.1 (q).

(iii) Synthesis of the compound 5

To a solution of the galactoside (compound C5, 7.3 mg) in tetrahydrofuran (2.0 ml) was added palladium black (1.5 mg). After the reaction vessel was purged with hydrogen, the mixture was stirred at room temperature for 16 hours, and then filtered through celite. The filtrate was concentrated. Purification on a silica gel column (Wako Gel C-200, 2 g), eluting with chloroform-methanol (8:1), produced the compound 5 in an amount of 4.4 mg (yield, 90.9%).

Data of the compound 5 was the same as those described above.

The compounds other than those described above (1–14) were synthesized by using appropriate carboxylic acids or combining Wittig's salts having alkyl groups of a variety of lengths in accordance with the synthetic methods of the compounds (9, 7, 5, 1) (synthetic routes A–C). The compounds 15, 35 and 29 had double bonds unreduced by conducting the reduction at the final stage with liquid ammonia and metallic sodium. Examples of the synthesis of these compounds are illustrated below.

Compound 2

The compound 2 was obtained by reacting the sphingosine C1 with p-nitrophenyl docosanoate in place of p-nitrophenyl tetracosanoate in the synthesis of the compound 1 and conducting synthesis by applying the route C.

As an alternative method, the compound 2 was obtained by reacting the amine B4 with p-nitrophenyl docosanoate in place of p-nitrophenyl octanoate in the synthesis of the compound 7 and conducting synthesis by applying the route B. [Data] $[\alpha]^{25}_D$=+50.70 (pyridine, c=0.82) MS: FDMS 787. IR: (cm$^{-1}$, KBr) 3390, 3220, 2870, 2810, 1635, 1535, 1455, 1080, 1055. mp: 147.0°–149.5° C. NMR: $^1$H (500 MHz, $C_5D_5N$; 27° C.)

δ (ppm) 8.53 (1H, d, J=8.6 Hz), 5.46 (1H, d, J=3.1 Hz), 4.74 (1H, m), 4.66 (1H, m), 4.4–4.6 (6H, m), 4.37 (1H, dd, J=5.8, 10.1 Hz), 4.29 (1H, m), 2.48 (2H, t, J=7.3 Hz), 1.80–1.97 (4H, m), 1.58 (1H, m), 1.20–1.45 (61H, m), 0.880 & 0.876 (each 3H, t, J=7.3 Hz). $^{13}$C (125 MHz, $C_5D_5N$; 27° C.)

δ (ppm) 173.4 (s), 102.2 (d), 73.1 (d), 72.0 (d), 71.7 (d), 71.0 (d), 70.6 (d), 69.7 (t), 62.7 (t), 54.9 (d), 36.8 (t), 35.1 (t), 32.1 (t), 30.2 (t), 30.1 (t), 30.0 (t), 29.95 (t), 29.92 (t), 29.83 (t), 29.76 (t), 29.62 (t), 29.61 (t), 26.6 (t), 26.4 (t), 22.9 (t), 14.3 (q).

Compound 3

The compound 3 was obtained by reacting the sphingosine C1 with p-nitrophenyl icosanoate in place of p-nitrophenyl tetracosanoate in the synthesis of the compound 1 and conducting synthesis by applying the route C.

As an alternative method, the compound 3 was obtained by reacting, the amine B4 with p-nitrophenyl icosanoate in place of p-nitrophenyl octanoate in the synthesis of the compound 7 and conducting further synthesis by applying the route B. [Data] $[\alpha]^{25}_D$=+47.3° (pyridine, c=1.76) MS: FDMS 759. IR: (cm$^{-1}$, KBr) 3390, 3220, 2880, 2810, 1635, 1530, 1455, 1080, 1055. mp: 151.5–153.0° C. NMR: $^1$H (500 MHz, $C_5D_5N$; 27° C.)

δ (ppm) 8.52 (1H, d, J=8.6 Hz), 5.46 (1H, d, J=4.3 Hz), 4.73 (1H, m), 4.66 (1H, dd, J=4.5, 10.1 Hz), 4.4–4.6 (6H, m), 4.37 (1H, dd, J=5.5, 10.4 Hz), 4.29 (1H, m), 2.48 .(2H, t, J=7.3 Hz), 1.80–1.97 (4H, m), 1.58 (1H, m), 1.20–1.42 (57H, m), 0.879 & 0.876 (each 3H, t, J=7.3 Hz). $^{13}$C (125 MHz, $C_5D_5N$; 27° C.)

δ (ppm) 173.4 (s), 102.1 (d), 73.1 (d), 71.9 (d), 71.6 (d), 71.0 (d), 70.5 .(d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 14.3 (q).

Compound 4

The compound 4 was obtained by reacting the sphingosine C1 with p-nitrophenyl stearate in place of p-nitrophenyl tetracosanoate in the synthesis of the compound 1 and conducting further synthesis by applying the route C.

As an alternative method, the compound 4 was obtained by reacting the amine B4 with p-nitrophenyl stearate in place of p-nitrophenyl octanoate in the synthesis of the compound 7 and conducting further synthesis by applying the route B. [Data] $[\alpha]^{25}_D$=+55.5° (pyridine, c=0.84) MS: FDMS 731. IR: (cm$^{-1}$, KBr) 3230, 2940, 2830, 1640, 1540, 1465, 1345, 1120, 1090, 1060. mp: 157.5°–159.5° C. NMR: $^1$H (500 MHz, $C_5D_5N$; 27° C.)

δ (ppm) 8.52 (1H, d, J=8.6 Hz), 5.46 (1H, d, J=3.7 Hz), 4.73 (1H, m), 4.66 (1H, dd, J=3.7, 9.8 Hz), 4.57 (1H, d, J=2.5 Hz), 4.55 (1H, t, J=6.1 Hz), 4.40–4.51 (4H, m), 4.37 (1H, dd, J=5.8, 10.7 Hz), 4.29 (1H, m), 2.48 (2H, t, J=7.3 Hz), 1.80–1.96 (4H, m), 1.59 (1H, m), 1.2–1.44 (53H, m), 0.88 (6H, t, J=6.7 Hz). $^{13}$C (125 MHz, $C_5D_5N$; 27° C.)

δ (ppm) 173.4 (s), 102.1 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 22.8.(t), 14.3 (q).

Compound 6

The compound 6 was obtained by reacting the sphingosine C1 with p-nitrophenyl decanoate in place of p-nitrophenyl tetracosanoate in the synthesis of the compound 1 and conducting further synthesis by applying the route C.

As an alternative method, the compound 6 was obtained by reacting the amine B4 with p-nitrophenyl decanoate in place of p-nitrophenyl octanoate in the synthesis of the compound 7 and conducting further synthesis by applying the route B. [Data] $[\alpha]^{25}_D$=+54.8° (pyridine, c=0.93) MS: FDMS 619. IR: (cm$^{-1}$, KBr) 3245, 2900, 2840, 1635, 1540, 1460, 1345, 1120, 1090, 1060. mp: 151.0–154.0° C. NMR: $^1$H (500 MHz, $C_5D_5N$; 27° C.)

δ (ppm) 8.52 (1H, d, J=9.2 Hz), 6.14 (1H, m), 5.45 (1H, d, J=3.7 Hz), 4.74 (1H, m), 4.65 (1H, dd, J=4.0, 10.1 Hz), 4.57 (1H, d, J=3.4 Hz), 4.54 (1H, t, J=5.8 Hz), 4.40–4.50 (4H, m), 4.36 (1H, dd, J=5.5, 11.0 Hz), 4.28 (1H, m), 2.47 (2H, dt, J=1.5, 7.6 Hz), 1.80–1.95 (4H, m), 1.57 (1H, m), 1.15–1.40 (37H, m), 0.87 & 0.85 (each 3H, t, J=6.7 Hz). $^{13}$C (125 MHz, $C_5D_5N$; 27° C.)

δ (ppm) 173.4 (s), 102.1 (d), 73.1 (d), 71.9 (d), 71.6 (d), 71.0 (d), 70.5 (d), 69.7 (t), 62.7 (t), 54.9 (d), 36.8 (t), 35.1 (t), 32.12 (t), 32.05 (t), 30.2 (t), 30.1 (t), 30.0 (t), 29.9 (t), 29.8 (t), 29.7 (t), 29.61 (t), 29.55 (t), 26.6 (t), 26.4 (t), 22.93 (t), 22.90 (t), 14.3 (q).

Compound 8

The compound 8 was obtained by reacting the sphingosine C1 with acetic anhydride in place of p-nitrophenyl tetracosanoate in the synthesis of the compound 1 and conducting further synthesis by applying the route C.

As an alternative method, the compound 8 was obtained by reacting the amine B4 with acetic anhydride in place of p-nitrophenyl octanoate in the synthesis of the compound 7 and conducting further synthesis by applying the route B. [Data] $[\alpha]^{25}_D=+74.3°$ (pyridine, c=1.36) MS: FDMS 507. IR: (cm$^{-1}$, KBr) 3230, 2890, 2830, 1630, 1540, 1465, 1370, 1140. mp: 171.0°–172.0° C. NMR: $^1$H (500 MHz, C$_5$D$_5$N; 27° C.)

δ (ppm) 8.63 (1H, d, J=8.6 Hz), 6.1 (2H, m), 5.43 (1H, d, J=3.7 Hz), 4.70 (1H, m), 4.64 (1H, dd, J=4.0, 10.1 Hz), 4.55 (1H, d, J=2.4 Hz), 4.52 (1H, t, J=6.1 Hz), 4.46 (1H, dd, J=3.7, 10.4 Hz), 4.38–4.44 (3H, m), 4.31 (1H, dd, J=6.1, 10.4 Hz), 4.26 (1H, m), 2.13 (3H, s), 1.77–1.90 (3H, m), 1.55 (1H, m), 1.20–1.40 (24H, m), 0.87 (3H, t, J=7.0 Hz). $^{13}$C (125 MHz, C$_5$D$_5$N; 27° C.)

δ (ppm) 170.3 (s), 102.0 (d), 73.0 (d), 71.9 (d), 71.6 (d), 70.9 (d), 70.5 (d), 69.4 (t), 62.6 (t), 55.0 (d), 35.0 (t), 32.1 (t), 30.1 (t), 30.04 (t), 29.97 (t), 29.9 (t), 29.6 (t), 26.6 (t), 23.3 (q), 22.9 (t), 14.3 (q).

Compound 10

In the synthesis of the compound 7, the aldehyde A2 was reacted with dodecanetriphenylphosphonium bromide in place of tetradecanetriphenylphosphonium bromide. Next, the amine obtained in the reduction was reacted with p-nitrophenyl myristate in place of p-nitrophenyl octanoate, and synthesis was further conducted by applying the route B to give the compound 10. [Data] $[\alpha]^{24}_D=+74.30$ (pyridine, c=0.35) MS: FDMS 646. IR: (cm$^{-1}$, KBr) 3250, 2900, 2830, 1640, 1540, 1460, 1120, 1085, 1060. mp: 153.5°–156.0° C. NMR: $^1$H (500 MHz, C$_5$D$_5$N; 27° C.)

δ (ppm) 8.52 (1H, d, J=8.6 Hz), 6.1 (1H, m), 5.47 (1H, d, J=3.7 Hz), 4.75 (1H, m), 4.67 (1H, dd, J=3.7, 9.8 Hz), 4.34–4.60 (7H, m), 4.29 (1H, m), 2.48 (2H, dt, J=1.2, 7.3 Hz), 1.80–1.95 (4H, m), 1.58 (1H, m), 1.20–1.42 (41H, m), 0.87 (6H, t, J=6.8 Hz). $^{13}$C (125 MHz, C$_5$D$_5$N; 27° C.)

δ (ppm) 173.4 (s), 102.1 (d), 73.1 (d), 72.0 (d), 71.7 (d), 71.0 (d), 70.6 (d), 69.7 (t), 62.7 (t), 54.9 (d), 36.8 (t), 35.1 (t), 32.1 (t), 30.2 (t), 30.1 (t), 30.00 (t), 29.97 (t), 29.9 (t), 29.8 (t), 29.7 (t), 29.6 (t), 26.6 (t), 26.4 (t), 22.9 (t), 14.3 (q).

Compound 11

In the synthesis of the compound 10, the (2S,3S)-aldehyde was used in place of the aldehyde A2, and the synthesis was conducted by applying the route B to give the compound 11. [Data] $[\alpha]^{24}_D=+62.00$ (pyridine, c=0.50) MS: FDMS 646. IR: (cm$^{-1}$, KBr) 3290, 2910, 2840, 1640, 1615, 1540, 1465, 1140, 1050. mp: 145.0°–147.0° C. NMR: $^1$H (500 MHz, C$_5$D$_5$N; 27° C.)

δ (ppm) 8.40 (1H, d, J=8.5 Hz), 6.28 (1H, m), 5.47 (1H, d, J=3.7 Hz), 4.66–4.76 (3H, m), 4.10–4.62 (7H, m), 2.48 (2H, dt, J=1.8, 7.3 Hz), 1.80–2.00 (3H, m), 1.70 (1H, m), 1.57 (1H, m), 1.20–1.42 (41H, m), 0.88 (6H, t, J=6.7 Hz).

Compound 12

In the synthesis of the compound 10, the (2S,3R)-aldehyde was used in place of the aldehyde A2, and the synthesis was conducted by applying the route B to give the compound 12. [Data] $[\alpha]^{23}_D=+52.50$ (pyridine, c=0.75) MS: FDMS 646. IR: (cm$^{-1}$, KBr) 3480, 3240, 2910, 2840, 1630, 1560, 1460, 1070, 1005. mp: 148.5°–152.5° C. NMR: $^1$H (500 MHz, C$_5$D$_5$N; 27° C.)

δ (ppm) 8.10 (1H, d, J=8.6 Hz), 5.46 (1H, d, J=3.7 Hz), 4.79 (1H, m), 4.66 (1H, dd, J=3.7, 9.8 Hz), 4.34–4.56 (7H, m), 4.12 (1H, t, J=6.1 Hz), 4.07 (1H, dd, J=6.1, 9.8 Hz), 2.49 (2H, t, J=6.5 Hz), 1.75–1.92 (3H, m), 1.69 (1H, m), 1.55 (1H, m), 1.20–1.42 (41H, m), 0.88 (6H, t, J=6.7 Hz). $^{13}$C (125 MHz, C$_5$D$_5$N; 27° C.)

δ (ppm) 173.6 (s), 101.4 (d), 73.0 (d), 71.8 (d), 71.1 (d), 70.6 (d), 70.4 (d), 69.8 (t), 62.8 (t), 53.1 (d), 36.8 (t), 35.3 (t), 32.1 (t), 30.2 (t), 30.0 (t), 29.93 (t), 29.89 (t), 29.8 (t), 29.7 (t), 29.6 (t), 26.6 (t), 26.5 (t), 22.9 (t), 14.3 (q).

Compound 13

In the synthesis of the compound 10, the (2R,3S)-aldehyde was used in place of the aldehyde A2, and the synthesis was conducted by applying the route B to give the compound 13. [Data] $[\alpha]^{24}_D=+80.70$ (pyridine, c=0.27) MS: FDMS 646. IR: (cm$^{-1}$, KBr) 3300, 2900, 2820, 1635, 1520, 1460, 1065, 1005. mp: 149.0°–150.5° C. NMR: $^1$H (500 MHz, C$_5$D$_5$N; 27° C.)

δ (ppm) 8.04 (1H, d, J=8.6 Hz), 6.4 (1H, m), 5.49 (1H, d, J=3.7 Hz), 4.80 (1H, m), 4.68 (1H, dd, J=3.7, 9.8 Hz), 4.65 (1H, bd, J=2.4 Hz), 4.36–4.58 (6H, m), 4.16 (1H, dd, J=6.7, 10.4 Hz), 2.50 (2H, t, J=7.3 Hz), 1.75–1.92 (3H, m), 1.69 (1H, m), 1.53 (1H, m), 1.20–1.42 (41H, m), 0.88 (6H, t, J=7.0 Hz).

Compound 14

The compound 14 was obtained by reacting the sphingosine C1 with p-nitrophenyl (R)-2-acertoxytetracosanoate in place of p-nitrophenyl tetracosanoate in the synthesis of the compound 1 and further conducting the synthesis by applying the route C.

As an alternative method, the compound 14 was obtained by reacting the amine B4 with p-nitrophenyl (R)-2-acetoxytetracosanoate in place of p-nitrophenyl octanoate in the synthesis of the compound 7 and conducting further synthesis by applying the route B. [Data] MS: FDMS 831. NMR: $^1$H (500 MHz, C$_5$D$_5$N; 27° C.)

δ (ppm) 8.45 (1H, d, J=9.2 Hz), 5.44 (1H, d, J=3.7 Hz), 4.71 (1H, m), 4.64 (2H,r m), 4.53 (3H, m), 4.40 (3H, m), 4.25 (1H, m), 2.22 (1H,r m), 2.09 (1H, m), 1.70–1.95 (4H, m), 1.54 (1H, m), 1.2–1.45 (63H, m), 0.884 & 0.876 (each 3H, t, J=6.7 Hz). $^{13}$C (125 MHz, C$_5$D$_5$N; 27° C.)

δ (ppm) 175.1 (s), 101.9 (d), 73.2 (d), 72.4 (d), 71.7 (d), 71.0 (d), 70.5 (d), 69.4 (t), 62.7 (t), 54.1 (d), 35.6 (t), 35.2 (t), 32.1 (t), 30.3 (t), 30.04 (t), 29.97 (t), 29.9 (t), 29.64 (t), 29.61 (t), 26.5 (t), 25.8 (t), 22.9 (t), 14.3 (q).

Compound 15

The compound 15 was obtained by reacting the sphingosine C1 with p-nitrophenyl stearate in place of p-nitrophenyl tetracosanoate in the synthesis of the compound 1 and further conducting the synthesis by applying the route C. The compound 15 as the deprotected derivative was obtained by conducting the deprotection at the final step by wetting the raw material with a small amount of tetrahydrofuran and adding thereto liquid ammonia and next metallic sodium. [Data] $[\alpha]^{25}_D=+41.40$ (pyridine, c=0.14) MS: FDMS 729. IR: (cm$^{-1}$, KBr) 3230, 2880, 2810, 1630, 1535, 1460, 1375, 1065, 1040. mp: 169.0°–172.0° C. NMR: $^1$H (500 MHz, C$_5$D$_5$N; 27° C.)

δ (ppm) 8.50 (1H, d, J=8.6 Hz), 6.01 (2H, bs), 5.47 (1H, d, J=3.7 Hz), 4.86 (2H, m), 4.67 (1H, dd, J=4.0, 10.1 Hz), 4.59 (1H, d, J=2.4 Hz), 4.54 (1H, t, J=5.8 Hz), 4.40–4.50 (5H, m), 4.37 (1H, m), 2.46 (2H, dt, J=3.1, 7.6 Hz), 2.09 (2H, bs), 1.84 (2H, m), 1.15–1.45 (50H, m), 0.88 (6H, t, J=6.4 Hz).

Compound 29

The synthesis was conducted by reacting the amine A7 with oleic acid in place of tetracosanoic acid in the synthesis of the compound 9 and further continuing the synthesis by applying the route C. The compound 29 as the deprotected derivative was obtained by conducting the deprotection in the final step by wetting the raw material with a small amount of tetrahydrofuran and then adding thereto liquid ammonia and metallic sodium. [Data] $[\alpha]^{24}_D$=+46.60 (pyridine, c=0.17) MS: FDMS 728. IR: (cm$^{-1}$, KBr) 3400, 2900, 2820, 1640, 1540, 1460, 1060. mp: 134°–136° C. NMR: $^1$H (500 MHz, C$_5$D$_5$N; 27° C.)

δ (ppm) 8.52 (1H, d, J=8.6 Hz), 6.54 (1H, bs), 6.45 (1H, bs), 6.35 (1H, bs), 6.15 (1H, bs), 5.44 (3H, m), 4.73 (1H, m), 4.66 (1H, dd, J=3.7, 9.8 Hz), 4.33–4.58 (7H, m), 4.27 (1H, m), 2.45 (2H, m), 2.06 (3H, m), 1.75–1.92 (2H, m), 1.55 (1H, m), 1.14–1.42 (48H, m), 0.84 (6H, m). $^{13}$C (125 MHz, C$_5$D$_5$N; 27° C.)

δ (ppm) 173.3 (s), 130.1 (d), 130.1 (d), 102.0 (d), 73.0 (d), 71.8 (d), 71.6 (d), 70.9 (d), 70.4 (d), 69.6 (t), 62.6 (t), 54.9 (d), 36.7 (t), 35.0 (t), 32.0 (t), 32.0 (t), 30.1 (t), 30.0 (t), 29.9 (t), 29.8 (t), 29.7 (t), 29.6 (t), 29.6 (t), 29.5 (t), 29.5 (t), 29.4 (t), 27.4 (t), 26.5 (t), 26.3 (t), 22.9 (t), 14.2 (q).

Compound 32

The synthesis was conducted by reacting the sphingosine C1 with p-nitrophenyl myristate in place of p-nitrophenyl tetracosanoate in the synthesis of the compound 1 and further by applying the route C. The compound 32 as the deprotected derivative was obtained by conducting the deprotection at the final step by wetting the raw material with a small amount of tetrahydrofuran and then adding thereto liquid ammonia and metallic sodium. [Data] $[\alpha]^{24}_D$= +48.90 (pyridine, c=0.45) MS: FDMS 673. IR: (cm$^{-1}$, KBr) 3320, 2920, 2855, 1640, 1545, 1470, 1345, 1150. mp: 158.0°–160.0° C. NMR: $^1$H (500 MHz, C$_5$D$_5$N; 27° C.)

δ (ppm) 8.46 (1H, d, J=7.3 Hz), 6.59 (1H, m), 6.41 (1H, m), 6.33 (1H, m), 6.00 (2H, bs), 5.46 (1H, d, J=3.7 Hz), 4.85 (2H, m), 4.65 (1H, dd, J=3.7, 9.8 Hz), 4.58 (1H, m), 4.53 (1H, t, J=6.1 Hz), 4.40–4.50 (4H, m), 4.35 (1H, dd, J=5.2, 10.1 Hz), 2.45 (2H, dt, J=3.1, 7.3 Hz), 2.08 (2H, m), 1.84 (2H, m), 1.37 (4H, m), 1.20–1.32 (38H, m), 0.88 (6H, t, J=6.7 Hz). $^{13}$C (125 MHz, C$_5$D$_5$N; 27° C.)

δ (ppm) 173.5 (s), 132.4 (d), 132.0 (d), 102.1 (d), 73.0 (d), 71.7 (d), 70.9 (d), 70.6 (d), 69.4 (t), 62.7 (t), 55.1 (d), 36.8 (t), 32.7 (t), 32.1 (t), 30.01 (t), 29.99 (t), 29.96 (t), 29.63 (t), 29.87 (t), 29.83 (t), 29.76 (t), 29.73 (t), 29.6 (t), 26.4 (t), 22.9 (t), 14.3 (q). (4) Synthetic route D The specific method for synthesizing a compound having a hydroxyl group at C-4 of the long chain base in formula (A) can be illustrated by the following reaction route scheme. Although the reaction route scheme specifically illustrates the method with reference to the compound 22, the compounds according to the present invention including 16–34 except for 22 and 29 can also be synthesized by applying the method (synthesis of the compound 22 (FIGS. 10a–10c)).

In the aforementioned scheme, the following abbreviations are used: EEDQ: 2-ethoxy-1-ethoxycarbonyl-1,2-dihydroquinoline.

The other abbreviations are the same as those in the previous reaction schemes. [$\alpha$]$^{24}_D$=+48.90 (pyridine, c=0.45) MS: FDMS 673. IR: (cm$^{-1}$, KBr) 3320, 2920, 2855, 1640, 1545, 1470, 1345, 1150. mp: 158.0°–160.0° C. NMR: $^1$H (500 MHz, C$_5$D$_5$N; 27° C.)

δ (ppm) 8.46 (1H, d, J=7.3 Hz), 6.59 (1H, m), 6.41 (1H, m), 6.33 (1H, m), 6.00 (2H, bs), 5.46 (1H, d, J=3.7 Hz), 4.85 (2H, m), 4.65 (1H, dd, J=3.7, 9.8 Hz), 4.58 (1H, m), 4.53 (1H, t, J=6.1 Hz), 4.40–4.50 (4H, m), 4.35 (1H, dd, J=5.2, 10.1 Hz), 2.45 (2H, dt, J=3.1, 7.3 Hz), 2.08 (2H, m), 1.84 (2H, m), 1.37 (4H, m), 1.20–1.32 (38H, m), 0.88 (6H, t, J=6.7 Hz). $^{13}$C (125 MHz, C$_5$D$_5$N; 27° C.)

δ (ppm) 173.5 (s), 132.4 (d), 132.0 (d), 102.1 (d), 73.0 (d), 71.7 (d), 70.9 (d), 70.6 (d), 69.4 (t), 62.7 (t), 55.1 (d), 36.8 (t), 32.7 (t), 32.1 (t), 30.01 (t), 29.99 (t), 29.96 (t), 29.63 (t), 29.87 (t), 35 29.83 (t), 29.76 (t), 29.73 (t), 29.6 (t), 26.4 (t), 22.9 (t), 14.3 (q). (4) Synthetic route D The specific method for synthesizing a compound having a hydroxyl group at C-4 of the long chain base in formula (A) can be illustrated by the following reaction route scheme. Although the reaction route scheme specifically illustrates the method with reference to the compound 22, the compounds according to the present invention including 16–34 except for 22 and 29 can also be synthesized by applying the method (synthesis of the compound 22 (FIGS. 10a–10c)).

In the aforementioned scheme, the following abbreviations are used: EEDQ: 2-ethoxy-1-ethoxycarbonyl-1,2-dihydroquinoline.

The other abbreviations are the same as those in the previous reaction schemes.

(i) Synthesis of the compound D1

The compound D1 can be synthesized by applying the method described in Agricultural and Biological Chemistry, 54 (3), 663–667, 1990.

(ii) Synthesis of the compound D3

To the Wittig's salt (compound D2, 32.07 g) was added tetrahydrofuran (40 ml), and the reaction vessel was purged with argon. A 2N solution of n-butyl lithium in hexane (30 ml) was added, and the mixture was stirred for 15 minutes. A solution of the aldehyde (compound D1, 13.18 g) in tetrahydrofuran (20 ml) was added dropwise to the mixture, which was then allowed to warm to room temperature and stirred for 15 hours. To the reaction mixture were added methanol (3 ml) followed by 20% aqueous methanol (300 ml), and the mixture was extracted thrice with n-hexane. The extracts were washed with brine and concentrated. Purification on a silica gel column (Wako Gel C-200, 400 g), eluting with hexane-ethyl acetate (9:1), produced an alcohol (compound D3) in an amount of 9.31 g (yield, 51.9%). Data of the compound D3 $[\alpha]^{24}_D$=+38.20° (CHCl$_3$, c=1.0) MS: FDMS 573, 301. NMR: $^1$H (500 MHz, CDCl$_3$; 27° C.)

δ (ppm) 7.20–7.35 (15H, m), 5.72 (1H, m), 5.46 (1H, bt, J=9.2 Hz), 4.68 (1H, d, J=11.2 Hz), 4.60 (1H, d, J=11.7 Hz), 4.47–4.52 (3H, m), 4.44 (1H, dd, J=5.5, 9.8 Hz), 4.33 (1H, d, J=11.7 Hz), 4.08 (1H, m), 3.56 (1H, dd, J=2.4, 5.5 Hz), 3.51 (2H, d, J=6.1 Hz), 3.01 (1H, d, J=5.5 Hz), 1.85–2.01 (2H, m), 1.17–1.36 (18H, m), 0.88 (3H, t, J=6.7 Hz).

(iii) Synthesis of the compound D4

To a solution of the alcohol (compound D3, 9.31 g) in tetrahydrofuran (30 ml) was added 10% palladium on charcoal (0.53 g). After the reaction vessel was purged with hydrogen, the mixture was stirred at room temperature for 15 hours, and then filtered through celite. The filtrate was concentrated to give a reduced product (compound D4) in an amount of 9.34 g (yield, quantitatively). Data of the compound D4 $[\alpha]^{24}_D$=−35.10 (CHCl$_3$, c=0.5) MS: FDMS 575. NMR: $^1$H (500 MHz, CDCl$_3$; 27° C.) δ (ppm) 7.22–7.34 (15H, m), 4.69 (1H, d, J=11.6 Hz), 4.65 (1H, d, J=11.6 Hz), 4.55 (1H, d, J=11.0 Hz), 4.52 (1H, d, J=11.6 Hz), 4.50 (1H, d, J=11.0 Hz), 4.48 (1H, d, J=12.2 Hz), 4.04 (1H, m), 3.68 (1H, m), 3.61 (1H, m), 3.54 (2H, m), 3.17 (1., d, J=4.9 Hz), 1.85 (3H, m), 1.65 (2H, m), 1.56 (1H, m), 1.41 (1H, m), 1.16–1.35 (17H, m), 0.88 (3H, t, J=7.3 Hz).

(iv) Synthesis of the compound D5

To a solution of the reduced product (compound D4, 9.34 g) in pyridine (70 ml) was added methanesulfonyl chloride (2.5 ml), and the mixture was stirred at room temperature for 2 hours, and then concentrated. After the residual acid chloride was distilled azeotropically with toluene, the residue was taken into diethyl ether and washed with brine. The organic layer was concentrated and purified on a silica gel column (Wako Gel C-200, 500 g, hexane-ethyl acetate (9:1)) to give a mesyl derivative (compound D5) in an amount of 9.74 g (yield, 91.8%). Data of the compound D5 $[\alpha]^{24}_D$=+6.50 (CHCl$_3$, c=1.0) MS: FDMS 653. NMR: $^1$H (500 MHz, CDCl$_3$; 27° C.)

δ (ppm) 7.25–7.38 (15H, m), 4.91 (1H, dt, J=3.9, 5.6 Hz), 4.76 (1H, d, J=11.2 Hz), 4.62 (1H, d, J=11.2 Hz), 4.58 (1H, d, J=11.5 Hz), 4.55 (1H, d, J=11.7 Hz), 4.48 (1H, d, J=11.2 Hz), 4.48 (1H, d, J=11.7 Hz), 3.89 (1H, t, J=4.9 Hz), 3.67–3.76 (2H, m), 3.61 (1H, m), 2.91 (3H, s), 1.72 (1H, m), 1.54 (1H, m), 1.41 (1H, m), 1.16–1.35 (21H, m), 0.88 (3H, t, J=7.3 Hz).

(v) Synthesis of the compound D6

To the solution of the mesyl derivative (compound D5, 9.74 g) in dimethylformamide (100 ml) was added sodium azide (9.70 g), and the mixture was stirred at 120° C. for 16 hours, then concentrated, taken into ethyl acetate and washed with water and brine. The organic layer was concentrated and purified on a silica gel column (Wako Gel C-200, 200 g, hexane-ethyl acetate (98:2)) to give an azide derivative (compound D6) in an amount of 6.75 g (yield, 75.4%). Data of the compound D6 $[\alpha]^{24}_D$=+8.20 (CHCl$_3$, c=1.0) MS: FDMS 600, 573, 450. NMR: $^1$H (500 MHz, CDCl$_3$; 27° C.)

δ (ppm) 7.25–7.40 (15H, m), 4.69 (1H, d, J=11.2 Hz), 4.60 (1H, d, J=11.2 Hz), 4.55 (1H, d, J=11.2 Hz), 4.48–4.53 (3H, m), 3.75–3.81 (2H, m), 3.65–3.72 (2H, m), 3.60 (1H, dt, J=3.7, 7.3 Hz), 1.66 (1H, m), 1.56 (1H, m), 1.41 (1H, m), 1.19–1.36 (21H, m), 0.88 (3H, t, J=6.7 Hz).

(vi) Synthesis of the compound D7

To the solution of the azide derivative (compound D6, 605.5 mg) in tetrahydrofuran (6 ml) was added 10% palladium on charcoal (60 mg). After the reaction vessel was purged with hydrogen, the mixture was stirred at room temperature for 15 hours, filtered through celite, and the filtrate was concentrated and purified on a silica gel column (Wako Gel C-200, 30 g, hexane-ethyl acetate (7:3)) to give an amine (compound D7) in an amount of 459.9 mg (yield, 79.4%). Data of the compound D7 $[\alpha]^{24}_D$=−7.0° (CHCl$_3$, c=0.5) MS: FDMS 574. NMR: $^1$H (500 MHz, CDCl$_3$; 27° C.)

δ (ppm) 7.23–7.36 (15H, m), 4.74 (1H, d, J=11.2 Hz), 4.63 (1H, d, J=11.5 Hz), 4.53 (1H, d, J=11.5 Hz), 4.52 (1H, d, J=11.5 Hz), 4.49 (2H, d, J=1.8 Hz), 3.71 (2H, m), 3.57 (1H, dd, J=3.7, 6.7 Hz), 3.49 (1H, m), 3.16 (1H, m), 1.82 (1H, m), 1.69 (1H, m), 1.58 (1H, m), 1.49 (1H, m), 1.20–1.35 (20H, bs), 0.88 (3H, t, J=7.3 Hz).

(vii) Synthesis of the compound D8

(R)-2-Acetoxytetracosanoic acid (compound D8) is obtained, for example, by reacting (R)-2-α-hydroxytetracosanoic acid which is synthesized by applying the method described in Agricultural and Biological Chemistry, 54 (12), 3337–3338, 1990 with acetic anhydride in pyridine. Data of the compound D8 $[\alpha]^{20}_D$=+8.50 (CHCl$_3$, c=1.0)

(viii) Synthesis of the compound D9

The amine (compound D7, 153.3 mg) and (R)-2-acetoxytetracosanoic acid (compound D8, 113.8 mg) were dissolved in tetrahydrofuran (4 ml), and 2-ethoxy-L-ethoxycarbonyl- 1,2-dihydroquinoline (EEDQ, 99.0 mg) was added to the solution. The mixture was stirred at room temperature for 60 hours, then concentrated and purified on a silica gel column (Wako Gel C-200, 10 g, hexane-ethyl acetate (9:1)) to give a benzylceramide (compound D9) in an amount of 205.6 mg (yield, 78.3%). Data of the compound D9 $[\alpha]^{23}_D$=+2.10 (CHCl$_3$, c=0.6) MS: FDMS 983. NMR: $^1$H (500 MHz, CDCl$_3$; 27° C.)

δ (ppm) 7.22–7.36 (15H, m), 6.50 (1H, d, J=9.2 Hz), 5.05 (1H, dd, J=4.9, 7.3 Hz), 4.82 (1H, d, J=11.6 Hz), 4.62 (1H, d, J=11.6 Hz), 4.55 (1H, d, J=11.6 Hz), 15 4.52 (1H, d, J=11.6 Hz), 4.42 (2H, s), 4.23 (1H, m), 3.84 (2H, m), 3.51 (1H, m), 3.48 (1H, dd, J=3.7, 9.8 Hz), 1.98 (3H, s), 1.60–1.82 (2H, m), 1.50 (1H, m), 1.20–1.35 (63H, m), 0.88 (6H, t, J=7.3 Hz).

(ix) Synthesis of the compound D10

To the solution of the benzylceramide (compound D9, 317.7 mg) in tetrahydrofuran-n-propanol (1:1) (6 ml) were added 10% palladium on charcoal (167.4 mg) and formic acid (0.6 ml). After the reaction vessel was purged with hydrogen, the mixture was stirred at 40° C. for 5 hours. The reaction mixture was diluted with chloroform (10 ml) and filtered through celite, and the filtrate was concentrated. Purification on a silica gel column (Wako Gel C-200, 15 g), eluting with chloroform-methanol (98:2), produced a ceramide (compound D10) in an amount 30 of 191.6 mg (yield, 83.2%). Data of the compound D10 $[\alpha]^{23}_D$=+6.0° (CHCl$_3$, c=0.1) MS: FDMS 713. NMR: $^1$H (500 MHz, C$_5$D$_5$N; 27° C.)

δ (ppm) 8.63 (1H, d, J=8.5 Hz), 6.56 (2H, m), 6.13 (1H, bd, J=5.7 Hz), 5.54 (1H, dd, J=5.5, 7.3 Hz), 5.07 (1H, m), 4.47 (1H, m), 4.43 (1H, m), 4.38 (1H, m), 4.28 (1H, m), 2.20 (1H, m), 2.07 (2H, m), 2.04 (3H, s), 1.90 (2H, m), 1.68 (1H, m), 1.15–1.60 (60H, m), 0.85 (6H, t, J=6.7 Hz).

(x) Synthesis of the compound D11

To the solution of the ceramide (compound D10, 99.7 mg) in pyridine (3 ml) were added triphenylmethyl chloride (390.3 mg) and 4-dimethylaminopyridine (5.0 mg), and the mixture was stirred at 60° C. for 3 hours. After dilution with chloroform (30 ml), the mixture was washed with brine and concentrated. Purification on a silica gel column (Wako Gel C-200, 5 g), eluting with chloroform, produced a trityl derivative (compound D11) in an amount of 111.7 mg (yield, 83.6%). Data of the compound D11 $[\alpha]^{23}_D$=−13.3° (CHCl$_3$, c=0.1) NMR: $^1$H (500 MHz, CDCl$_3$; 27° C.) (ppm) 7.21–7.40 (15H, m), 6.89 (1H, d, J=8.6 Hz), 5.21 (1H, dd, J=5.1, 6.6 Hz), 4.27 (1H, m), 3.60 (1H, m), 3.43 (1H, dd, J=3.2, 7.1 Hz), 3.36 (1H, dd, J=4.2, 7.1 Hz), 3.34 (1H, m), 3.01 (1H, m), 2.08 (1H, m), 2.05 (3H, s), 1.85 (1H, m), 1.75 (1H, m), 1.68 (1H, m), 1.10–1.50 (62H, m), 0.88 (6H, t, J=7.3 Hz).

(xi) Synthesis of the compound D12

To the solution of the trityl derivative (compound D11, 166.5 mg) in pyridine (3 ml) were added benzoyl chloride (0.18 ml) and 4-dimethylaminopyridine (5.0 mg). After stirring at room temperature for 36 hours, the mixture was diluted with brine, extracted with chloroform and concentrated. Purification on a silica gel column (Wako Gel C-200, 15 g), eluting with hexane-ethyl acetate (95:5), produced a benzoyl derivative (compound D12) in an amount of 193.9 mg (yield, 95.6%). Data of the compound D12 $[\alpha]^{23}_D$=+7.3° (CHCl$_3$, c=0.5) MS: FDMS 1162, 920. NMR: $^1$H (500 MHz, CDCl$_3$; 27° C.)

δ (ppm) 7.04–8.16 (25H, m), 5.91 (1H, dd, J=2.4, 9.0 Hz), 5.45 (1H, dt, J=2.9, 9.8 Hz), 5.37 (1H, t, J=7.3 Hz), 4.68 (1H, m), 3.34 (1H, dd, J=3.7, 9.8 Hz), 3.26 (1H, dd, J=2.9, 9.8 Hz), 2.02 (3H, s), 1.12–2.02 (66H, m), 0.87 (6H, m).

(xii) Synthesis of the compound D13

To the solution of benzoyl derivative (compound D12, 193.9 mg) in a solution of methylene chloride-methanol (2:1) (3 ml) was added p-toluenesulfonic acid monohydrate (63.4 mg). After being stirred at room temperature for 1.5 hours, the mixture was concentrated. The residue was dissolved in ethyl acetate and washed with aqueous sodium hydrogen carbonate and brine, and then concentrated. Purification on a silica gel column (Wako Gel C-200, 15 g), eluting with hexane-ethyl acetate (8:2), produced an alcohol (compound D13) in an amount of 113.1 mg (yield, 73.7%). Data of the compound D13 $[\alpha]^{23}_D$=+27.30 (CHCl$_3$, c=0.1) MS: FDMS 921. NMR: $^1$H (500 MHz, CDCl$_3$; 27° C.)

δ (ppm) 8.06 (2H, d, J=7.3 Hz), 7.96 (2H, d, J=7.3 Hz), 7.64 (1H, t, J=7.3 Hz), 7.54 (1H, t, J=7.6 Hz), 7.50 (2H, t, J=7.9 Hz), 7.39 (2H, t, J=7.9 Hz), 7.06 (1H, d, J=9.2 Hz), 5.48 (1H, dd, J=2.4, 9.1 Hz), 5.38 (1H, dt, J=3.1, 9.8 Hz), 5.19 (1H, t, J=6.1 Hz), 4.37 (1H, m), 3.57–3.68 (2H, m), 2.20 (3H, s), 2.02 (2H, m), 1.92 (2H, m), 1.16–1.50 (62H, m), 0.88 (6H, m).

(xiii) Synthesis of the compound D14

To the solution of the alcohol (compound D13, 113.1 mg) in tetrahydrofuran (2 ml) were added stannous chloride (54.8 mg), silver perchlorate (59.9 mg) and powdered Molecular Sieves 4A (500 mg), and the mixture was stirred at room temperature for 30 minutes. After the mixture was cooled to −10° C., a solution of benzylgalactosyl fluoride (compound A13, 313.4 mg) in tetrahydrofuran (2 ml) was added. The resulting mixture was allowed to warm to room temperature, stirred for 2 hours, then diluted with acetone, and filtered through celite. The filtrate was evaporated under reduced pressure, and the residue was suspended in ethyl acetate, washed with brine and concentrated. Purification on a silica gel column (Wako Gel C-200, 10 g) eluting with hexane-ethyl acetate (19:1) produced an α-galactoside (compound D14) in an amount of 148.0 mg (yield; 83.5%). Data of the compound D14 $[\alpha]^{23}_D$=+21.00 (CHCl$_3$, c=0.1) MS: FDMS 1443. NMR: $^1$H (500 MHz, CDCl$_3$; 27° C.)

δ (ppm) 8.03 (2H, d, J=7.9 Hz), 7.90 (2H, d, J=7.9 Hz), 7.73 (1H, d, J=8.3 Hz), 7.59 (1H, t, J=6.4 Hz), 7.50 (1H, t, J=6.4 Hz), 7.45 (2H, t, J=7.6 Hz), 7.15–7.40 (22H, m), 5.78 (1H, dd, J=2.6, 9.8 Hz), 5.40 (1H, m), 5.10 (1H, dd, J=5.2, 7.6 Hz), 4.88 (1H, d, J=11.3 Hz), 4.53–4.76 (7H, m), 4.48 (1H, d, J=11.8 Hz), 4.40 (1H, d, J=11.8 Hz), 4.09 (1H, t, J=7.2 Hz), 3.99 (1H, dd, J=3.3, 10.4 Hz), 3.93 (1H, m), 3.90 (1H, m), 3.82 (1H, dd, J=2.4, 9.8 Hz), 3.59 (1H, dd, J=2.3, 12.1 Hz), 3.53 (1H, dd, J=6.4, 8.9 Hz), 3.45 (1H, dd, J=6.7, 9.2 Hz), 2.44 (1H, bs), 2.02 (3H, s), 1.89 (3H, m), 1.40 (2H, m), 1.10–1.35 (61H, m), 0.88 (6H, m).

(xiv) Synthesis of the compound D15

To the solution of the α-galactoside (compound D14, 147.1 mg) in ethyl acetate (3 ml) was added palladium black (15 mg). After the reaction vessel was purged with hydrogen and the mixture was stirred at room temperature for 4 hours, filtered through celite, and the filtrate was concentrated to give a tetraol (compound D15) in an amount of 106.6 mg (yield, 96.6%). Data of the compound D15 $[\alpha]^{23}_D$=+26.00 (CHCl$_3$, c=0.1) MS: FDMS 1083, 921. NMR: $^1$H (500 MHz, CDCl$_3$; 27° C.)

δ (ppm) 7.99 (2H, d, J=7.9 Hz), 7.90 (2H, d, J=7.9 Hz), 7.75 (1H, d, J=8.3 Hz), 7.60 (1H, t, J=6.4 Hz), 7.53 (1H, t, J=6.4 Hz), 7.48 (2H, t, J=7.6 Hz), 7.38 (2H, t, J=7.6 Hz), 5.78 (1H, dd, J=2.4, 9.8 Hz), 5.26 (1H, m), 5.07 (1H, t, J=6.7 Hz), 4.70 (1H, d, J=3.7 Hz), 4.57 (1H, m), 3.98 (1H, bs), 3.90 (1H,-m), 3.80–3.90 (3H, m), 3.78 (1H, m), 3.70 (1H, m), 3.65 (1H, bd, J=10.4 Hz), 3.46 (2H, m), 3.13 (1H, bs), 2.78 (1H, m), 2.18 (3H, s), 1.81–1.95 (4H, m), 1.41 (2H, m), 1.16–1.35 (60H, m), 0.88 (6H, m).

(xv) Synthesis of the compound 22

To the solution of the tetraol (compound D15, 105.5 mg) in methanol (5 ml) was added slowly a 1N methanolic sodium methoxide solution (2 ml), and the mixture was stirred at room temperature for 30 minutes. A cation exchange resin (Dowex 50W, X8, manufactured by The Dow Chemical Company) was added to neutralize the mixture, and the resulting mixture was filtered. The solids removed were washed thoroughly with a chloroform-methanol (1:1) solution. The extract was combined with the filtrate, and concentrated. Purification on a silica gel column (Wako Gel C-200, 5 g) eluting with chloroform-methanol-water (90:10:1) produced a cerebroside (compound 22) in an amount of 66.7 mg (yield, 82.2%). Data of the compound 22 $[\alpha]^{23}_D$=+47.40 (Pyridine, c=4.0) MS: FDMS 833. 35 IR: (cm$^{-1}$, KBr) 3400, 2950, 2870, 1645, 1535, 1475, 1080 mp: 202°–204° C. NMR: $^1$H (500 MHz, C$_5$D$_5$N; 27° C.)

δ (ppm) 8.48 (1H, d, J=9.2 Hz), 7.53 (1H, d, J=4.9 Hz), 7.00 (1H, bs), 6.67 (1H, d, J=6.7 Hz), 6.63 (1H, bs), 6.51 (1H, bs), 6.28 (1H, bs), 6.07 (1H, d, J=5.5 Hz), 5.57 (1H, d, J=3.7 Hz), 5.26 (1H, m), 4.62 (2H, m), 4.57 (1H, m), 4.51 (1H, bs), 4.46 (2H, m), 4.28–4.40 (4H, m) 4.25 (1H, m), 2.27 (1H, m), 2.17 (1H, m), 1.98 (1H, m), 1.87 (2H, m), 1.73 (1H, m), 1.66 (2H, m), 1.16–1.46 (58H, m), 0.85 (6H, t, J=6.1 Hz). $^{13}$C (125 MHz, C$_5$D$_5$N; 27° C.)

δ (ppm) 175.0 (s), 101.2 (d), 76.5 (d), 73.0 (d), 72.3 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.8 (t), 29.5 (t), 26.4 (t), 25.8 (t), 22.9 (t), 14.2 (q).

The compounds (16–21, 23-28, 30-31, 33-34) were synthesized by using various carboxylic acids or combining a variety of Wittig's salts by applying the method for synthesizing the compound 22 (reaction route D). Synthetic examples of these compounds are herein illustrated.

Compound 16

The aldehyde D1 was reacted with tridecanetriphenylphosphonium bromide in place of the Wittig's salt in the synthesis of the compound 22. Synthesis was further conducted by applying the route D. The amine obtained by reducing an azide group was reacted with tetracosanoic acid in place of (R)-2-acetoxytetracosanoic acid D8, and the synthetic process was followed by applying the route D to obtain the compound 16. [Data] $[\alpha]^{24}_D$=+28.2° (pyridine, c=0.27) MS: FDMS 831. IR: (cm$^{-1}$, KBr) 3350, 2920, 2850, 1640, 154G, 1465. mp: 146°–147° C. NMR: $^1$H (500 MHz, C$_5$D$_5$N; 27° C.)

δ (ppm) 8.45 (1H, d, J=8.5 Hz), 5.55 (1H, d, J=3.7 Hz), 5.24 (1H, m), 4.64 (2H, m), 4.52 (1H, m), 4.48 (1H, m), 4.38 (4H, m), 4.28 (2H, bs), 2.41 (2H, t, J=6.3.Hz), 2.24 (1H, m), 1.88 (2H, m), 1.78 (2H, m), 1.64 (1H, m), 1.10–1.45 (62H, m), 0.85 (6H, t, J=6.7 Hz). $^{13}$C (125 MHz, C$_5$D$_5$N; 27° C.)

δ (ppm) 173.2 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.3 (t), 32.1 (t), 30.4 (t), 30.1 (t), 30.0 (t), 29.9 (t), 29.9 (t), 29.8 (t), 29.7 (t), 29.6 (t), 26.5 (t), 26.4 (t), 22.9 (t), 14.3 (q).

Compound 17

The amine obtained by reducing an azide group by applying the route D in the synthesis of the compound 22 was reacted with tetracosanoic acid in place of (R)-2- acetoxytetracosanoic acid D8, and the synthetic process was followed by applying the route D to obtain the compound 17. [Data] $[\alpha]^{23}{}_D$=+42.40 (pyridine, c=0.8) MS: FDMS 817. IR: (cm$^{-1}$, KBr) 3400, 2950, 2870, 1645, 1535, 1475, 1080. mp: 166°–168° C. NMR: $^1$H (500 MHz, C$_5$D$_5$N; 27° C.)

δ (ppm) 8.43 (1H, d, J=8.6 Hz), 5.55 (1H, d, J=3.7 Hz), 5.23 (1H, m), 4.64 (1H, dd, J=5.5, 10.4 Hz), 4.62 (1H, dd, J=4.3, 10.4 Hz), 4.52 (1H, m), 4.49 (1H, bt, J=6.1 Hz), 4.33–4.42 (4H, m), 4.30 (2H, m), 2.42 (2H, dd, J=6.7, 7.3 Hz), 2.26 (1H, m), 1.86 (2H, m), 1.78 (2H, m), 1.65 (1H, m), 1.16–1.46 (60H, m), 0.85 (6H, t, J=6.7 Hz). $^{13}$C (125 MHz, C$_5$D$_5$N; 27° C.)

δ (ppm) 173.2 (s), 101.5 (d), 76.7 (d), 73.0 (d), 72.4 (d), 71.5 (d), 70.9 (d), 70.2 (d), 68.6 (t), 62.6 (t), 51.4 (d), 36.7 (t), 34.3 (t), 32.1 (t), 30.3 (t), 30.1 (t), 30.0 (t), 29.9 (t), 29.8 (t), 29.8 (t), 29.7 (t), 29.7 (t), 29.5 (t), 26.4 (t), 26.3 (t), 22.9 (t), 14.2 (q).

Compound 18

The aldehyde D1 was reacted with decanetriphenylphosphonium bromide in place of the Wittig's salt D2 in the synthesis of the compound 22. The subsequent synthetic process was followed by applying the route D. The amine obtained by reducing the azide group was reacted with tetracosanoic acid in place of (R)-2-acetoxytetracosanoic acid D8, and the subsequent steps were followed by applying the route D to obtain the compound 18. [Data] $[\alpha]^{24}{}_D$=+30.00 (pyridine, c=0.2) MS: FDMS 789. IR: (cm$^{-1}$, KBr) 3350, 2920, 2840, 1640, 1540, 1465. mp: 154°–155° C. NMR: $^1$H (500 MHz, C$_5$D$_5$N; 27° C.)

δ (ppm) 8.45 (1H, d, J=8.5 Hz), 5.55 (1H, d, J=3.7 Hz), 5.24 (1H, m), 4.64 (2H, m), 4.53 (1H, m), 4.49 (1H, m), 4.39 (4H, m), 4.30 (2H, bs), 2.42 (2H, t, J=6.7 Hz), 2.25 (1H, m), 1.88 (2H, m), 1.78 (2H, m), 1.64 (1H, m), 1.15–1.45 (56H, m), 0.85 & 0.84 (each 3H, t, J=7.3 Hz). $^{13}$C (125 MHz, C$_5$D$_5$N; 27° C.)

δ (ppm) 173.3 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.3 (t), 32.1 (t), 30.3 (t), 29.6–30.1, 26.5 (t), 26.4 (t), 22.9 (t), 14.3 (q).

Compound 19

The aldehyde D1 was reacted with hexanetriphenylphosphonium bromide in place of the Wittig's salt D2 in the synthesis of the compound 22. The subsequent synthetic process was followed by applying the route D. The amine obtained by reducing the azide group was reacted with tetracosanoic acid in place of (R)-2-acetoxytetracosanoic acid D8, and the subsequent steps were followed by applying the route D to obtain the compound 19. [Data] MS: FDMS 732. NMR: $^1$H (500 MHz, C$_5$D$_5$N; 27° C.)

δ (ppm) 8.45 (1H, d, J=8.6 Hz), 6.97 (1H, bs), 6.62 (1H, bs), 6.52 (1H, m), 6.43 (1H, bs), 6.29 (1H, d, J=3.7 Hz), 6.06 (1H, bs), 5.58 (1H, d, J=3.7 Hz), 5.26 (1H, m), 4.66–4.68 (2H, m), 4.55 (1H, bs), 4.51 (1H, m), 4.38–4.42 (4H, m), 4.30 (1H, bs), 2.44 (2H, t, J=7.3 Hz), 1.80–1.88 (4H, m), 1.19–1.59 (50H, m), 0.88 & 0.81 (each 3H, t, J=6.7 Hz).

Compound 20

Synthesis was conducted by applying the route D in the synthesis of the compound 22. The amine obtained by reducing the azide group was reacted with hexacosanoic acid in place of (R)-2-acetoxytetracosanoic acid D8, and the subsequent steps were followed by applying the route D to obtain the compound 20. [Data] $[\alpha]^{25}{}_D$=+37.70 (pyridine, c=0.97) MS: FDMS 845. IR: (cm$^{-1}$, KBr) 3380, 2920, 2840, 1635, 1545, 1465, 1065. mp: 156°–158° C. NMR: $^1$H (500 MHz, C$_5$D$_5$N; 27° C.)

δ (ppm) 8.46 (1H, d, J=8.6 Hz), 6.42 (1H, m), 6.09 (1H, m), 5.57 (1H, d, J=3.7 Hz), 5.26 (1H, m), 4.66 (2H, m), 4.55 (1H, m), 4.51 (1H, t, J=5.8 Hz), 4.41 (4H, m), 4.32 (2H, m), 2.44 (2H, t, J=7.0 Hz), 2.28 (1H, m), 1.90 (2H, m), 1.81 (2H, m), 1.68 (1H, m), 1.15–1.45 (64H, m), 0.88 (6H, t, J=6.7 Hz). $^{13}$C (125 MHz, C$_5$D$_5$N; 27° C.)

δ (ppm) 173.2 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.4 (t), 32.1 (t), 30.4 (t), 30.1 (t), 30.03 (t), 29.99 (t), 29.93 (t), 29.87 (t), 29.81 (t), 29.76 (t), 29.6 (t), 26.5 (t), 26.4 (t), 22.9 (t), 14.3 (q).

Compound 33

In the synthesis of Compound 22, the aldehyde D1 was treated with, instead of the Wittig salt D2, tridecanetriphenylphosphonium bromide, and the amine synthesized in accordance with the route D, with an azide group reduced was treated with, instead of the (R)-2-acetoxytetracosanic acid D8, hexacosanic acid. After this, the synthesis was continued in accordance with the route D to give Compound 33. [Data] $[\alpha]^{23}{}_D$=+43.90 (pyridine, c=0.81) MS: negative FAB-MS 857 [(M-H)$^-$] IR: (cm$^{-1}$, KBr) 3300, 2980, 2850, 1640, 1540, 1470, 1070. mp: 130°–135° C. NMR: $^1$H (500 MHz, C$_5$D$_5$N; 27° C.)

δ (ppm) 8.47 (1H, d, J=8.5 Hz), 6.97 (1H, d, J=1.8Hz), 6.63 (1H, bs), 6.54 (1H, m), 6.44 (1H, d, J=5.5 Hz), 6.32 (1H, bs), 6.09 (1H, d, J=5.0 Hz), 5.58 (1H, d, J=3.7 Hz), 5.27 (1H, m), 4.65–4.70 (2H, m), 4.56 (1H, bs), 4.52 (1H, t, J=5.5 Hz), 4.37–4.47 (4H, m), 4.31–4.35 (2H, m), 2.45 (2H, t, J=7.3 Hz), 1.78–1.97 (4H, m), 1.26–1.69 (68H, m), 0.88 (6H, t, J=6.7 Hz). $^{13}$C (125 MHz, C$_5$D$_5$N; 27° C.)

δ (ppm) 173.2 (s), 101.5 (d), 76.7 (d), 73.0 (d), 72.5 (d), 71.6 (d), 71.0 (d), 70.3 (d), 68.7 (t), 62.7 (t), 51.4 (d), 36.8 (t), 34.4 (t), 32.1 (t), 30.4 (t), 10 30.2 (t), 30.0 (t), 30.0 (t) 29.9 (t), 29.9 (t), 29.8 (t), 29.6 (t), 26.5 (t), 26.4 (t), 22.9 (t), 14.3 (q).

Compound 34

In the synthesis of Compound 22, the amine synthesized in accordance with the route D, with an azide group remained was treated with, instead of the (R)-2-acetoxytetracosanic acid D8, octacosanic acid. After this, the synthesis was continued in accordance with the route D to give Compound 34. [Data] $[\alpha]^{24}{}_D$=+46.80° (pyridine, c=0.47) MS: negative FAB-MS 871 [(M-H)$^-$]. IR: (cm$^{-1}$, KBr) 3350, 2930, 2850, 1640, 1540, 1470, 1080. mp: 142°–145° C. NMR: $^1$H (500 MHz, C$_5$D$_5$N; 27° C.)

δ (ppm) 8.46 (1H, d, J=7.9 Hz), 6.92–6.98 (1H, m), 6.59–6.63 (1H, m), 6.53 (1H, bs), 6.44 (1H, d, J=5.5 Hz), 6.33 30 (1H, bs), 6.07 (1H, d, J=5.5 Hz), 5.58 (1H, d, J=3.7 Hz), 5.25–5.30(1H, m), 4.62–4.70 (2H, m), 4.56 (1H, bs), 4.52 (1H, t, J=6.1 Hz), 4.36–4.47 (3H, m), 4.29–4.35 (2H, m), 2.44 (2H, t, J=6.7 Hz), 1.78–1.97 (4H, m), 1.25–1.72 (70H, m), 0.88 (6H, t, J=6.7 Hz). $^{13}$C (125 MHz, C$_5$D$_5$N; 27° C.)

δ (ppm) 173.2 (s), 101.5 (d), 76.7 (d), 73.0 (d), 72.5 (d), 71.6 (d), 71.0 (d), 70.3 (d), 68.6 (t), 62.6 (t), 51.4 (d), 36.8 (t), 34.3 (t), 32.1 (t), 30.3 (t), 30.1 (t), 30.0 (t), 30.0 (t), 29.9 (t), 29.9 (t), 29.8 (t), 29.7 (t), 29.6 (t), 26.5 (t), 26.4 (t), 22.9 (t), 14.3 (q).

Compound 21

In the synthesis of Compound 22, the aldehyde D1 was treated with, instead of the Wittig salt D2, tridecanetriphenylphosphonium bromide. After this, the synthesis was continued in accordance with the route D to give Compound 21. [Data] MS: FDMS 847. IR: (cm$^{-1}$, KBr) 3400, 2950, 2870, 1645, 1535, 1475, 1080. NMR: $^1$H (500 MHz, C$_5$D$_5$N; 27° C.)

δ (ppm) 8.50 (1H, d, J=9.2 Hz), 5.59(1H, d, J=3.7 Hz), 5.27 (1H, m), 4.64 (2H, m), 4.58 (1H, m), 4.53 (1H, m), 4.48 (2H, m), 4.30–4.42 (4H, m), 4.27 (1H, m), 2.29 (1H, m), 2.18 (1H, m), 1.98 (1H, m), 1.87 (2H, m), 1.74 (1H, m), 1.67 (2H, m), 1.15–1.46 (60H, m), 0.84 (6H, t, J=6.7 Hz). $^{13}$C (125 MHz, C$_5$D$_5$N; 27° C.)

δ (ppm) 174.9 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.5 (t), 26.4 (t), 25.8 (t), 22.9 (t), 14.2 (q).

Compound 23

In the synthesis of Compound 22, the aldehyde D1 was treated with, instead of the Wittig salt D2, decanetriphenylphosphonium bromide. After this, the synthesis was continued in accordance with the route D to give Compound 23. [Data] [α]$^{24}_D$=+59.20 (pyridine, c=0.1) MS: FDMS 805. IR: (cm$^{-1}$, KBr) 3400, 2950, 2870, 1645, 1535, 1475, 1080. mp: 193°–194° C. NMR: $^1$H (500 MHz, C$_5$D$_5$N; 27° C.)

δ (ppm) 8.50 (1H, d, J=9.2 Hz), 5.59 (1H, d, J=3.7 Hz), 5.28 (1H, m), 4.64 (2H, m), 4.58 (1H, m), 4.53 (1H, m), 4.48 (2H, m), 4.30–4.42 (4H, m), 4.27 (1H, m), 2.29 (1H, m), 2.18 (1H, m), 1.98 (1H, m), 1.87 (2H, m), 1.74 (1H, m), 1.66 (2H, m), 1.15–1.46 (54H, m), 0.84 (6H, t, J=6.7 Hz). $^{13}$C (125 MHz, C$_5$D$_5$N; 27° C.)

δ (ppm) 174.9 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.5 (t), 26.4 (t), 25.8 (t), 22.9 (t), 14.2 (q).

Compound 24

In the synthesis of Compound 22, the aldehyde D1 was treated with, instead of the Wittig salt D2, hexanetriphenylphosphonium bromide. After this, the synthesis was continued in accordance with the route D to give Compound 24. [Data] [α]$^{23}_D$=+67.1° (pyridine, c=1.32) MS: FDMS 749. IR: (cm$^{-1}$, KBr) 3300, 2870, 2800, 1630, 1605, 1515, 1455, 1060. mp: 145°–147° C. NMR: $^1$H (500 MHz, C$_5$D$_5$N; 27° C.) δ (ppm) 8.50 (1H, d, J=9.2 Hz), 6.70 (2H, bd, J=6.1 Hz), 6.53 (1H, bs), 6.31 (1H, bs), 6.08 (1H, bs), 5.61 (1H, d, J=3.7 Hz), 5.29 (1H, m), 4.64–4.67 (2H, m), 4.59 (1H, m), 4.54 (1H, m), 4.47–4.51 (2H, m), 4.32–4.43 (4H, m), 4.26 (1H, m), 1.64–2.27 (4H, m), 1.20–1.40 (50H, m), 0.87 & 0.82 (each 3H, t, J=6.7 Hz). $^{13}$C (125 MHz, C$_5$D$_5$N; 27° C.)

δ (ppm) 175.0 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.0 (t), 30.2 (t), 29.9 (t), 29.8 (t), 29.7 (t), 29.5 (t), 26.3 (t), 25.8 (t), 22.9 (t), 22.8 (t), 14.21 (q), 14.18 (q).

Compound 25

In the synthesis of Compound 22, the aldehyde D1 was treated with, instead of the Wittig salt D2, tridecanetriphenylphosphonium bromide, and the amine synthesized in accordance with the route D, with an azide group reduced was treated with, instead of the (R)-2-acetoxytetracosanic acid D8, (R)-2-acetoxyhexacosanic acid. After this, the synthesis was continued in accordance with the route D to give Compound 25. [Data] [α]$^{23}_D$=+45.20 (pyridine, c=1.0) MS: FDMS 875. IR: (cm$^{-1}$, KBr) 3400, 2950, 2870, 1645, 1535, 1475, 1080. mp: 198°–199° C. NMR: $^1$H (500 MHz, C$_5$D$_5$N; 27° C.)

δ (ppm) 8.49 (1H, d, J=9.2 Hz), 7.53 (1H, bs), 7.02 (1H, bs), 6.70 (1H, d, J=6.1 Hz), 6.65 (1H, bs), 6.53 (1H, bs), 6.30 (1H, bs), 6.08 (1H, d, J=5.5 Hz), 5.57 (1H, d, J=3.7 Hz), 5.26 (1H, m), 4.62 (2H, dd, J=4.9, 10.4 Hz), 4.58 (1H, m), 4.51 (1H, bs), 4.46 (2H, m), 4.28–4.41 (4H, m), 4.26 (1H, m), 2.27 (1H, m), 2.17 (1H, m), 1.98 (1H, m), 1.87 (2H, m), 1.74 (1H, m), 1.66 (2H, m), 1.16–1.46 (64H, m), 0.85 (6H, t, J=6.1 Hz). $^{13}$C (125 MHz, C$_5$D$_5$N; 27° C.)

δ (ppm) 175.0 (s), 101.2 (d), 76.5 (d), 73.0 (d), 72.4 (d), 72.3 (d), 71.6 (d), 70.9 (d), 70.1 (d), 68.2 (t), 62.6 (t), 50.5 (d), 35.5 (t), 34.4 (t), 32.1 (t), 30.3 (t), 30.1 (t), 29.9 (t), 29.9 (t), 29.6 (t), 26.4 (t), 25.8 (t), 22.9 (t), 14.2 (q).

Compound 26

In the synthesis of Compound 22, the aldehyde D1 was treated with, instead of the Wittig salt D2, tetradecanetriphenylphosphonium bromide, and the amine synthesized in accordance with the route D, with an azide group reduced was treated with, instead of the (R)-2-acetoxytetracosanic acid D8, (R)-2-acetoxyhexacosanic acid. After this, the synthesis was continued in accordance with the route D to give Compound 26. [Data] [α]$^{23}_D$=+46.50 (pyridine, c=0.7) MS: FDMS 889. IR: (cm$^{-1}$, KBr) 3400, 2950, 2870, 1645, 1535, 1475, 1080. mp: 205°–206° C. NMR: $^1$H (500 MHz, C$_5$D$_5$N; 27° C.)

δ (ppm) 8.50 (1H, d, J=9.2 Hz), 7.56 (1H, bs), 7.04 (1H, bs), 6.71 (1H, d, J=6.7 Hz), 6.66 (1H, bs), 6.54 (1H, bs), 6.32 (1H, bs), 6.10 (1H, d, J=5.5 Hz), 5.58 (1H, d, J=3.7 Hz), 5.27 (1H, m), 4.63 (2H, m), 4.58 (1H, m), 4.52 (1H, bs), 4.47 (2H, m), 4.28–4.41 (4H, m), 4.27 (1H, m), 2.27 (1H, m), 2.18 (1H, m), 1.99 (1H, m), 1.88 (2H, m), 1.74 (1H, m), 1.66 (2H, m), 1.16–1.46 (66H, m), 0.85 (6H, t, J=6.7 Hz). $^{13}$C (125 MHz, C$_5$D$_5$N; 27° C.)

δ (ppm) 175.0 (s), 101.2 (d), 76.5 (d), 73.0 (d)r 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 29.9 (t), 29.9 (t), 29.5 (t), 26.4 (t), 25.8 (t), 22.9 (t), 14.2 (q).

Compound 27

In the synthesis of Compound 22, the aldehyde D1 was treated with, instead of the Wittig salt D2, heptadecanetriphenylphosphonium bromide, and the amine synthesized in accordance with the route D, with an azide group reduced was treated with, instead of the (R)-2-acetoxytetracosanic acid D8, (R)-2-acetoxyhexacosanic acid. After this, the synthesis was continued in accordance with the route D to give Compound 27. [Data] [α]$^{23}_D$=+46.00 (pyridine, c=0.8) MS: FDMS 903. IR: (cm$^{-1}$, KBr) 3400, 2950, 2870, 1645, 1535, 1475, 1080. mp: 200°–201° C. NMR: $^1$H (500 MHz, C$_5$D$_5$N; 27° C.)

δ (ppm) 8.49 (1H, d, J=9.2 Hz), 7.54 (1H, bs), 7.02 (1H, bs), 6.69 (1H, d, J=6.7 Hz), 6.66 (1H, bs), 6.53 (1H, bs), 6.30 (1H, bs), 6.08 (1H, d, J=4.9 Hz), 5.57 (1H, d, J=3.7 Hz), 5.25 (1H, m), 4.62 (2H, dd, J=4.9, 10.4 Hz), 4.57 (1H, m), 4.51 (1H, bs), 4.46 (2H, m), 4.28–4.40 (4H, m), 4.26 (1H, m), 2.26 (1H, m), 2.17 (1H, m), 1.98 (1H, m), 1.87 (2H, m), 1.73 (1H, m), 1.65 (2H, m), 1.16–1.46 (68H, m), 0.86 (6H, t, J=6.7 Hz). $^{13}$C-(125 MHz, C$_5$D$_5$N; 27° C.)

δ (ppm) 175.0 (s), 101.2 (d), 76.4 (d), 73.0 (d), 72.4 (d), 72.3 (d), 71.5 (d), 70.9 (d), 70.1 (d), 68.1 (t), 62.6 (t), 50.5 (d), 35.5 (t), 34.3 (t), 32.1 (t), 30.3 (t), 30.1 (t), 29.9 (t), 29.6 (t), 26.4 (t), 25.8 (t), 22.9 (t), 14.2 (q).

In another method for synthesizing Compounds 25, 26 and 27, Cereblin E was used. In the synthesis of Compound 22, Cereblin E (a product of Alfred Baker Chemicals or K & K Laboratories, Inc.), a tetraol, was used instead of the triol D10, and a mixture of Compounds 25, 26 and 27 was obtained in accordance with the route D. This mixture was subjected to a high performance liquid chromatography ("D-ODS-5" manufactured by YMC Co., Ltd., solvent: 100% methanol, 45° C.) for separation. Thus, each compound was obtained.

Compound 28

In the synthesis of Compound 22, the amine 15 synthesized in accordance with the route D, with an azide group reduced was treated with, instead of the (R)-2-acetoxytetracosanic acid D8, (S)-2-acetoxytetracosanic acid. After this, the synthesis was continued in accordance with the route D to give Compound 28. [Data] $[\alpha]^{23}_D$=+36.8° (pyridine, c=2.0) MS: FDMS 833.

IR: (cm$^{-1}$, KBr) 3400, 2950, 2870, 1645, 1535, 1475, 1080. mp: 174°–176° C. NMR: $^1$H (500 MHz, C$_5$D$_5$N; 27° C.)

δ (ppm) 8.55 (1H, d, J=8.5 Hz), 5.61 (1H, d, J=4.3 Hz), 5.26 (1H, m), 4.68 (1H, dd, J=5.5, 10.4 Hz), 4.63 (1H, 30 dd, J=3.7, 9.8 Hz), 4.56 (2H, bs), 4.49 (1H, t, J=5.5 Hz), 4.46 (1H, dd, J=3.7, 9.8 Hz), 4.38 (2H, m), 4.34 (1H, dd, J=4.3, 11.0 Hz), 4.31 (1H, bd, J=8.6 Hz), 4.20 (1H, dd, J=3.7, 7.9 Hz), 2.26 (1H, m), 2.19 (1H, m), 1.99 (1H, m), 1.84 (2H, m), 1.74 (1H, m), 1.58–1.70, (2H, m), 1.16–1.46 (58H, m), 0.85 (6H, t, J=6.7 Hz). $^{13}$C (125 MHz, C$_5$D$_5$N; 27° C.)

δ (ppm) 175.0 (s), 101.2 (d), 76.7 (d), 73.0 (d), 72.5 (d), 72.4 (d), 71.6 (d), 70.9 (d), 70.1 (d), 68.0 (t), 62.6 (t), 50.5 (d), 35.6 (t), 34.6 (t), 32.1 (t), 30.3 (t), 30.1 (t), 29.9 (t), 29.9 (t), 29.6 (t), 26.3.(t), 25.8 (t), 22.9 (t), 14.2 (q).

Compound 30

In the synthesis of Compound 22, the aldehyde D1 was treated with, instead of the Wittig salt D2, 11-methyl-9-dodecentriphenylphosphonium bromide, and the amine synthesized in accordance with the route D, with an azide group reduced was treated with, instead of the (R)-2-acetoxytetracosanic acid D8, (S)-2-acetoxytetracosanic acid. After this, the synthesis was continued in accordance with the route D to give Compound 30. [Data] $[\alpha]^{25}_D$=+46.20 (pyridine, c=1.0) MS: FDMS 847. IR: (cm$^{-1}$, KBr) 3400, 3250, 2870, 2810, 1640, 1525, 1455, 1355, 1320, 1275, 1145, 1060. mp: 169.0°–171.0° C. NMR: $^1$H (500 MHz, C$_5$D$_5$N; 27° C.)

δ (ppm) 8.57 (1H, d, J=9.2 Hz), 6.64 (2H, m), 6.45 (1H, m), 6.30 (1H, m), 6.11 (2H, m), 5.65 (1H, d, J=3.7 Hz), 5.29 (2H, m), 4.65–4.75 (2H, m), 4.59 (2H, m), 4.51 (2H, m), 4.30–4.45 (4H, m), 4.22 (1H, m), 2.30 (1H, m), 2.21 (1H, m), 2.02 (1H, m), 1.6–2.0 (5H, m), 1.49 (1H, m), 1.15–1.35 (56H, m), 0.89 (3H, t, J=6.1 Hz), 0.87 (6H, d, J=6.1 Hz). $^{13}$C (125 MHz, C$_5$D$_5$N; 27° C.)

δ (ppm) 175.0 (s), 101.3 (d), 76.7 (d), 73.0 (d), 72.4 (d), 72.3 (d), 71.6 (d), 70.9 (d), 70.1 (d), 68.0 (t), 62.6 (t), 50.6 (d), 39.2 (t), 35.6 (t), 34.6 (t), 32.1 (t), 30.3 (t), 30.2 (t), 30.1 (t), 30.0 (t), 29.9 (t), 29.6 (t), 28.1 (d), 27.7 (t), 26.3 (t), 25.8 (t), 22.9 (t), 22.7 (q), 14.2 (q).

Compound 31

In the synthesis of Compound 22, the aldehyde D1 was 5 treated with, instead of the Wittig salt D2, 11-methyl-9-dodecentriphenylphosphonium bromide, and the amine synthesized in accordance with the route D, with an azide group reduced was treated with, instead of the (R)-2-acetoxytetracosanic acid D8, tetracosanic acid. After this, the synthesis was continued in accordance with the route D to give Compound 31. [Data] $[\alpha]^{25}_D$=+43.6° (pyridine, c=0.44) MS: FDMS 831. IR: (cm$^{-1}$, KBr) 3300, 2880, 2810, 1630, 1535, 1455, 1055. mp: 197.0°–198.5° C. NMR: $^1$H (500 MHz, C$_5$D$_5$N; 27° C.)

δ (ppm) 20 8.44 (1H, d, J=8.6 Hz), 5.57 (1H, d, J=3.7 Hz), 5.25 (1H, m), 4.63–4.70 (2H, m), 4.54 (1H, d, J=3.1 Hz), 4.50 (1H, t, J=6.1 Hz), 4.35–4.45 (4H, m), 4.31 (2H, m), 2.44 (2H, t, J=7.3 Hz), 2.28 (1H, m), 1.90 (2H, m), 1.81 (2H, m), 1.68 (1H, m), 1.49 (1H, m), 1.2–1.45 (56H, m), 1.15 (2H, m), 0.88 (3H, t, J=6.7 Hz), 0.87 (6H, d, J=6.7 Hz). $^{13}$C (125 MHz, C$_5$D$_5$N; 27° C.)

δ (ppm) 173.2 (s), 101.5 (d), 76.7 (d), 73.0 (d), 72.5 (d), 30 71.6 (d), 71.0 (d), 70.3 (d), 68.7 (t), 62.7 (t), 51.4 (d), 39.3 (t), 36.8 (t), 34.4 *(t), 32.1 (t), 30.4 (t), 30.23 (t), 30.15 (t), 30.03 (t), 30.00 (t), 29.91 (t), 29.87 (t), 29.81 (t), 29.75 (t), 29.6 (d), 28.2 (d), 27.7 (t), 26.5 (t), 26.4 (t), 22.9 (t), 22.8 (q), 14.3 (q).

EXAMPLES

The following are experimental examples of the present invention. However, the present invention is not limited by the following examples.

Pharmacological Test 1: Proliferation-Stimulating Effect on Marrow Cell of Mouse Marrow cells were prepared from the thigh bone of a 7 week old female BALB/c mouse purchased from Japan SLC Co., Ltd., and a mononuclear cell fraction (MNF) obtained by fractionation using a lympholyte-M (Cedar Lane, Ontario, Canada), was used in the following experiment.

The concentration of the MNF was adjusted to 1.5×10$^6$ cells/ml by using 10% FCS RPMI 1640 (Nissui Pharmaceutical Co., Ltd., Tokyo, Japan) as a culture medium. 10 μl/well of a sample with a predetermined concentration and 100 μl/well of the above-prepared MNF were placed on a round-bottomed 96 well plate, and incubated under the conditions of 37° C. and 5% CO$_2$ for 72 hours. Thereafter, 0.5 μCi/well of $^3$H-thymidine ($^3$H-TdR) was added. After 8 hour incubation, the cells were harvested, and the amount of the 3H-TdR taken in the nuclei was measured by a liquid scintillation counter.

The percentages of the values of experimental plot to the value of control are shown in Table 1.

TABLE 1

| Sample/Concentration | Uptake of $^3$H-TdR (%) | | | |
|---|---|---|---|---|
| (μg/ml) | 10$^0$ | 10$^{-1}$ | 10$^{-2}$ | 10$^{-3}$ |
| 1 | 1348 | 465 | 263 | 134 |
| 5 | 1143 | 377 | 261 | 234 |
| 8 | 1056 | 232 | 81 | 129 |
| 7 | 972 | 631 | 351 | 313 |
| 32 | 871 | 405 | 151 | 115 |
| 29 | 865 | 382 | 187 | 97 |
| 14 | 1184 | 511 | 132 | 134 |
| 17 | 1140 | 462 | 149 | 159 |
| 18 | 1157 | 472 | 124 | 129 |
| 16 | 1244 | 495 | 152 | 115 |
| 19 | 1326 | 499 | 207 | 173 |
| 9 | 1236 | 547 | 103 | 134 |
| 4 | 1332 | 297 | 75 | 151 |
| 15 | 979 | 292 | 101 | 69 |
| 6 | 1639 | 391 | 196 | 71 |
| 20 | 982 | 466 | 201 | 67 |
| 2 | 915 | 295 | 92 | 123 |
| 3 | 1098 | 234 | 87 | 84 |
| 10 | 1036 | 356 | 90 | 77 |
| 31 | 624 | 326 | 104 | 101 |
| 24 | 576 | 197 | 79 | 77 |
| 23 | 761 | 312 | 89 | 81 |
| 30 | 712 | 293 | 105 | 92 |
| 21 | 799 | 244 | 96 | 84 |
| 22 | 613 | 226 | 116 | 104 |
| 28 | 1051 | 192 | 170 | 130 |
| 25 | 1370 | 331 | 161 | 153 |
| 26 | 1564 | 271 | 183 | 156 |
| 27 | 1091 | 220 | 165 | 156 |

TABLE 1-continued

| Sample/Concentration | Uptake of $^3$H-TdR (%) | | | |
|---|---|---|---|---|
| (μg/ml) | $10^0$ | $10^{-1}$ | $10^{-2}$ | $10^{-3}$ |
| 33 | 1253 | 460 | 330 | 175 |
| 34 | 1085 | 272 | 183 | 150 |

As shown in Table 1, all of the samples showed a remarkable marrow-cell-proliferation-accelerating effect.

Pharmacological Test 2: Effect on Marrow Cell of Monkey

Marrow cells were prepared from the humerus of a croo monkey, and an MNF obtained by fractionation using a Lymphoprep (Nycomed Pharma AS, Oslo, Norway) was used in the following experiment.

The MNF was suspended in an RPMI 1640 medium added with 10% blood plasma of a croo monkey to make its concentration $1\times10^6$ cells/ml.

10 μl/well of a sample with a predetermined concentration and 100 μl/well of the above-prepared MNF were placed on a round-bottomed 96 well plate, and incubated under the conditions of 37° C. and 5% $CO_2$ for 4 days. Thereafter, 0.5 μCi/well of $^3$H-TdR was added. After 6 hours, the cells were harvested, and the amount of the $^3$H-TdR taken in the nuclei was measured by a liquid scintillation counter. The percentages of the values of experimental plot to the value of control are shown in Table 2.

TABLE 2

| Sample/Concentration | Uptake of $^3$H-TdR (%) | |
|---|---|---|
| μg/ml | $10^{-1}$ | $10^{-2}$ |
| 25 | 184 | 186 |
| 33 | 177 | 194 |

As shown in Table 2, both of the samples showed a remarkable 3H-TdR-uptake-accelerating effect.

Pharmacological Test 3: Proliferation-Stimulating Effect on Mononuclear Cell Fraction of Human Umbilical Cord Blood It is extremely difficult to obtain human marrow cells. In addition, human umbilical cord blood contains stem cells (Nakahata, T. & Ogwa, M., J. Clin. Inveet. 70, 1324–1328 (1982)), so that it can be a good source of hematopoietic stem/progenitor cell supply (H. E. Broxneyer et al, Proc. Natl. Acad. Sci. USA, 86, 3828–3832 (1989)). For these reasons, the effect on human was examined by using, instead of human marrow cells, human umbilical cord blood.

To human umbilical cord blood was, added an equal amount of RPMI 1640. This was placed-on a Lymphoprep and centrifuged. The mononuclear cell fraction (MNF) thus obtained was used in the following experiment.

The concentration of the MNF was adjusted to $1\times10^6$ cells/ml by using an RPMI 1640 added with 10% auto-blood plasma as a culture medium. 10 μl/well of a sample with a predetermined concentration and 100 μl/well of the above-prepared MNF were placed on a round-bottomed 96 well plate and incubated under the conditions of 37° C. and 5% $CO_2$ for 4 days. Thereafter, 0.5 μCi/well of $^3$H-TdR was added. After 8 hour incubation, the cells were harvested, and the amount of the 3H-TdR taken in the nuclei was measured by a liquid scintillation counter.

The percentages of the values of experimental plot to the value of control are shown in Table 3.

TABLE 3

| Sample/Concentration | Uptake of $^3$H-TdR (%) | | |
|---|---|---|---|
| (μg/ml) | $10^{-1}$ | $10^{-2}$ | $10^{-3}$ |
| 27 | 450 | 486 | 344 |
| 23 | 402 | 344 | 197 |
| 21 | 552 | 530 | 305 |
| 20 | 692 | 474 | 507 |
| 22 | 362 | 357 | 204 |
| 28 | 356 | 331 | 182 |
| 14 | 233 | 141 | 96 |
| 18 | 298 | 177 | 135 |
| 16 | 311 | 204 | 216 |
| 17 | 318 | 233 | 98 |
| 25 | 336 | 319 | 229 |
| 33 | 409 | 256 | 228 |
| 34 | 467 | 258 | 291 |

The data was divided by a horizontal line with every series of experiments..

As shown in Table 3, all of the samples showed a remarkable 3H-TdR-uptake-accelerating effect.

From the above results, it was clearly proved that the compounds represented by the formula (A) have a stimulating effect on proliferation of the marrow cells or umbilical cord blood cells of mouse, monkey and human.

Pharmacological Test 4: Life-Span-Increasing Effect on Irradiation of a Lethal Dose of Radiation An experiment was carried out by using 6 week old female BDF1 mice purchased from Japan SLC Co., Ltd., with 10 mice made one group. The entire bodies of the mice were irradiated with 9 GY of X-rays by using a Hitachi X-ray irradiator (MBR-1520R), and the day on which the X-ray was irradiated was referred to as "day 0". On days 0, 4 and 8, each sample was administered to the caudal vein of the mice at a dose of 0.1 mg/kg, and the mice were observed with respect to their life or death for 40 days.

The numbers of surviving mice on days 10, 15, 20, 25, 30, 35 and 40 are shown in Table 4.

TABLE 4

Radiation-Protecting Effect

| | Number of Surviving Mice | | | | | | |
|---|---|---|---|---|---|---|---|
| Compound No. | 10 | 15 | 20 | 25 | 30 | 35 | 40 (days) |
| Control | 10 | 8 | 4 | 3 | 1 | 0 | 0 |
| 5 | 10 | 9 | 9 | 9 | 9 | 9 | 9 |
| Control | 10 | 9 | 5 | 3 | 1 | 0 | 0 |
| 1 | 10 | 10 | 10 | 9 | 9 | 9 | 9 |
| 6 | 9 | 6 | 2 | 2 | 2 | 2 | 2 |
| 7 | 10 | 8 | 6 | 5 | 5 | 5 | 5 |
| 10 | 10 | 8 | 7 | 7 | 7 | 7 | 7 |
| Control | 10 | 5 | 1 | 0 | 0 | 0 | 0 |
| 14 | 10 | 10 | 10 | 9 | 9 | 9 | 9 |
| 18 | 10 | 10 | 8 | 7 | 7 | 7 | 7 |
| 19 | 10 | 10 | 10 | 10 | 10 | 10 | 10 |
| 9 | 10 | 8 | 6 | 6 | 6 | 6 | 6 |
| 4 | 10 | 10 | 8 | 7 | 5 | 5 | 5 |
| 8 | 10 | 5 | 1 | 1 | 1 | 1 | 1 |
| 2 | 10 | 10 | 9 | 9 | 9 | 9 | 8 |
| 3 | 10 | 9 | 8 | 8 | 8 | 8 | 8 |
| 32 | 10 | 9 | 4 | 3 | 3 | 3 | 3 |
| Control | 10 | 5 | 2 | 0 | 0 | 0 | 0 |
| 24 | 10 | 9 | 9 | 9 | 9 | 9 | 9 |
| 23 | 10 | 10 | 9 | 9 | 9 | 9 | 9 |
| 21 | 10 | 10 | 10 | 10 | 10 | 10 | 10 |
| 22 | 10 | 10 | 10 | 9 | 8 | 8 | 8 |
| 17 | 10 | 10 | 9 | 9 | 9 | 9 | 9 |
| 16 | 10 | 6 | 6 | 6 | 6 | 6 | 6 |

TABLE 4-continued

Radiation-Protecting Effect

| Compound No. | Number of Surviving Mice |||||||
| --- | --- | --- | --- | --- | --- | --- | --- |
| | 10 | 15 | 20 | 25 | 30 | 35 | 40 (days) |
| 15 | 10 | 9 | 6 | 6 | 6 | 6 | 6 |
| 20 | 10 | 8 | 7 | 7 | 6 | 6 | 6 |
| 25 | 10 | 10 | 7 | 7 | 5 | 5 | 5 |
| Control | 10 | 7 | 3 | 2 | 0 | 0 | 0 |
| 31 | 10 | 10 | 9 | 9 | 9 | 9 | 9 |
| 30 | 10 | 10 | 10 | 10 | 10 | 10 | 10 |
| 28 | 10 | 10 | 10 | 8 | 8 | 8 | 8 |
| 26 | 10 | 9 | 9 | 8 | 8 | 8 | 8 |
| 27 | 10 | 10 | 9 | 9 | 9 | 9 | 9 |
| 29 | 10 | 9 | 8 | 8 | 8 | 8 | 8 |
| Control | 8 | 1 | 0 | 0 | 0 | 0 | 0 |
| 33 | 10 | 8 | 7 | 5 | 5 | 5 | 5 |
| 34 | 10 | 10 | 10 | 9 | 9 | 9 | 9 |

Pharmacological Test 5: Thrombocytopenia-Inhibiting Effect

The thrombocytopenia-inhibiting effect of each sample upon an X-ray-irradiated mouse, which is one of models with a decreased number of blood platelets, was examined.

An experiment was carried out by using 6 week old female $BDF_1$ mice purchased from Japan SLC Co., Ltd., with 6 mice made one group.

5 Gy of X ray was irradiated to the entire body of the mice by a Hitachi X-ray irradiator CMBR-1520R). Within 2 hours after the irradiation, each sample was administered to the caudal vein of the mice at an amount of 0.1 mg/kg.

After 10 days, blood was collected from the fundus vein of the mice, and the number of blood platelets was measured by a sequential multi-channel hemocytometer E-2500/cs (Toa Iyo Denshi Kabushiki Kaisha). The number of blood platelets of the non-treated group, that of the medium-administered group, and that of the sample-administered group are shown in Table 5.

TABLE 5

| Compound No. | Number of Blood Platelets ($\times 10^4/\mu l$) Mean value ± Standard deviation |
| --- | --- |
| Non-treatment | 68.2 ± 6.5 |
| Vehicle | 10.3 ± 4.1 |
| 31 | 27.7 ± 5.4 |
| 14 | 22.3 ± 6.6 |
| 24 | 21.6 ± 7.2 |
| 23 | 21.0 ± 5.9 |
| 30 | 22.5 ± 3.5 |
| 21 | 22.7 ± 3.7 |
| 1 | 25.4 ± 6.8 |
| 25 | 15.6 ± 5.3 |
| 34 | 24.4 ± 5.6 |
| 33 | 23.9 ± 6.5 |
| Non-treatment | 96.9 ± 11.6 |
| Vehicle | 6.8 ± 2.5 |
| 22 | 25.4 ± 5.1 |
| 28 | 20.4 ± 4.5 |
| 5 | 20.3 ± 4.5 |
| 18 | 24.3 ± 8.6 |
| 16 | 21.1 ± 6.2 |
| 19 | 23.4 ± 4.2 |
| 9 | 17.6 ± 3.4 |
| 4 | 14.3 ± 4.7 |
| 15 | 17.8 ± 2.4 |
| 6 | 15.4 ± 3.2 |
| Non-treatment | 73.0 ± 2.0 |
| Vehicle | 6.7 ± 1.2 |
| 17 | 18.5 ± 4.4 |
| 20 | 19.8 ± 7.3 |
| 8 | 8.1 ± 2.6 |
| 2 | 21.5 ± 5.4 |
| 3 | 20.6 ± 4.5 |
| 7 | 12.3 ± 4.0 |
| 26 | 19.8 ± 4.3 |
| 27 | 16.0 ± 4.1 |
| 10 | 19.6 ± 4.0 |
| 32 | 16.4 ± 3.2 |
| 29 | 18.1 ± 5.0 |

As shown in Table 5, all of the samples showed a remarkable blood-platelet-decrease-inhibitory effect.

From the above results, it was clearly proved that the compounds represented by the formula (A) have a remarkable blood-platelet-decrease-inhibitory effect upon irradiation of radiation.

Subsequently, the effect on blood platelet was examined using normal mice.

Pharmacological Test 6: Blood-Platelet-Increasing Effect upon Mouse

An experiment was carried out by using 6 week old female $BDF_1$ mice purchased from Japan SLC Co., Ltd., with 5 mice made one group.

Each sample was administered to the caudal vein of the mice at a dose of 0.1 mg/kg. After 6 days, blood was collected from the fundus vein of the mice, and the number of blood platelets was measured by a sequential multi-channel hemocytometer E-2500/cs (Toa Iyo Denshi Kabushiki Kaisha). The number of blood platelets of the vehicle-administered group, and that of the sample-administered group are shown in Table 6.

TABLE 6

| Compound No. | Number of Blood Platelets ($\times 10^4/\mu l$) Mean value ± Standard deviation |
| --- | --- |
| Vehicle | 58.2 ± 7.1 |
| 31 | 108.0 ± 7.0 |
| 14 | 101.6 ± 8.3 |
| 24 | 102.6 ± 9.9 |
| 23 | 108.7 ± 14.8 |
| 30 | 106.2 ± 9.0 |
| 21 | 94.8 ± 7.7 |
| 1 | 112.2 ± 6.5 |
| 34 | 110.1 ± 9.0 |
| 22 | 104.1 ± 7.7 |
| 28 | 103.6 ± 8.8 |
| 17 | 92.1 ± 11.3 |
| 18 | 111.7 ± 5.4 |
| 16 | 114.7 ± 13.0 |
| 19 | 106.4 ± 12.7 |
| Vehicle | 63.0 ± 7.0 |
| 9 | 100.5 ± 8.3 |
| 4 | 83.1 ± 6.5 |
| 15 | 84.7 ± 6.0 |
| 6 | 93.0 ± 12.1 |
| 20 | 110.9 ± 10.6 |
| 8 | 96.6 ± 3.2 |
| 2 | 96.3 ± 7.3 |
| 3 | 102.0 ± 10.8 |
| 7 | 76.0 ± 5.1 |
| 26 | 113.7 ± 7.1 |
| 27 | 101.3 ± 7.1 |
| 10 | 87.2 ± 4.0 |
| 32 | 88.3 ± 4.2 |

TABLE 6-continued

| Compound No. | Number of Blood Platelets ($\times 10^4/\mu l$) Mean value ± Standard deviation |
|---|---|
| 29 | 86.3 ± 3.1 |
| Vehicle | 71.1 ± 4.4 |
| 5 | 106.0 ± 9.0 |
| 25 | 124.1 ± 14.7 |
| 33 | 142.3 ± 10.2 |

As shown in Table 6, all of the samples clearly showed a blood-platelet-increasing effect.

As shown in Table 6, it was clearly proved that the compounds represented by the formula (A) have a remarkable blood-platelet-increasing effect upon a normal mouse.

Subsequently, in order to examine the effect on Primates, the effect of Compound 33 was examined as a representative of the compounds represented by the formula (A), by using normal croo monkeys.

Pharmacological Test 7: Blood-Platelet-Increasing Effect upon Monkey

Six croo monkeys (female, 3 to 5 years old, 2.3 to 2.8 kg), 2 monkeys in one group were used. A vehicle, 0.1 mg/body of the compound 33 or 1 mg/body of the compound 33 was intravenously administered to the monkeys. 6 and 9 days after the administration, blood was collected by using a blood-collecting tube EDTA-2K, and the numbers of blood platelets, white blood cells and red blood cells contained in the peripheral blood were measured by using an E-2500/cs. The results are shown in Tables 7-1, 7-2 and 7-3, respectively.

TABLE 7-1

| Compound | dose mg/body | Number of Blood Platelets ($\times 10^{-4}/\mu l$) | |
|---|---|---|---|
| | | after 6 days | after 9 days |
| Vehicle | — | 37.8 ± 8.5 | 37.4 ± 12.4 |
| 33 | 0.1 | 56.4 ± 5.2 | 52.4 ± 9.0 |
| 33 | 1 | 62.1 ± 15.9 | 64.7 ± 23.7 |

TABLE 7-2

| Compound | dose mg/body | Number of White Blood Cells ($\times 10^{-2}/\mu l$) | |
|---|---|---|---|
| | | after 6 days | after 9 days |
| Vehicle | — | 91 ± 31 | 94 ± 57 |
| 33 | 0.1 | 156 ± 1 | 105 ± 15 |
| 33 | 1 | 150 ± 37 | 169 ± 21 |

TABLE 7-3

| Compound | dose mg/body | Number of Red Blood Cells ($\times 10^{-4}/\mu l$) | |
|---|---|---|---|
| | | after 6 days | after 9 days |
| Vehicle | — | 516 ± 6 | 506 ± 1 |
| 33 | 0.1 | 498 ± 18 | 538 ± 2 |
| 33 | 1 | 569 ± 40 | 574 ± 37 |

As shown in Table 7-1, it was clearly proved that Compound 33 shows a remarkable blood-platelet-increasing effect even when administered at a dose of 0.1 mg/body, which effect is almost equal to the effect obtained when the compound is administered at a dose of 1mg/body.

Further, as shown in Table 7-2, Compound 33 showed a remarkable white-blood-cell-increasing effect 6 days after the administration at a dose of 0.1 mg/body, which effect was equal to the effect obtained when the compound was administered at a dose of 1 mg/body.

Furthermore, as shown in Table 7-3, a red-blood-cell-increasing effect was clearly found, 9 days after the administration, in the group administered with 0.1 mg/body of Compound 33.

In addition, by the observation conducted until 10 days after the administration, no abnormality in body weight and in general condition was found even in the group administered with 1 mg/body of Compound 33.

Preparation Example 1 (Injection)

| (1) Compound of formula (A) | 1 mg |
|---|---|
| (2) Polysorbate | 100 mg |
| (3) Distilled water for injection | suitable amount |
| Total | 1 ml |

In accordance with the above formulation, (1) and (2) are dissolved in (3), and the solution is filtered through a sterilizer. The resultant is then charged in a vial or an ampoule to give an injection.

Preparation Example 2 (Tablet)

| (1) Compound of formula (A) | 1 mg |
|---|---|
| (2) Lactose | 80 mg |
| (3) Corn starch | 30 mg |
| (4) Hydroxypropylcellulose | 3 mg |
| (5) Magnesium stearate | 1 mg |
| Total | 115 mg |

In accordance with the above formulation, (1) to (4) are admixed and granulated to obtain granule to be used for preparing tablets. To this granule is added (5), and the mixture is made into a homogeneous powder which is subjected to compression molding by using a compressor to give tablets.

[Test Examples]

Test Example 1: Cytotoxicity

100 µl/well of B16 mouse melanoma cells with a concentration of $1 \times 10^5$ cells/ml and 10 µl/well of one of Compounds 1 to 34 with a predetermined concentration were placed on a flat-bottomed 96 well microplate. Incubation was conducted under the conditions of 37° C. and 5% $CO_2$ for 42 hours, and 0.5 µCi/well of $^3$H-TdR was then added. After further 8 hours, the cells were harvested, and the amount of $^3$H-TdR taken in the cells was measured. It was found that all of the compounds had no influence upon cell proliferation even at the final concentration of 10 µg/ml.

Test Example 2: Acute Toxicity 0.1, 1.0 or 10 mg/kg of Compound 5 or 33 was intravenously administered to Crj:CD rats (male, 5 weeks old), 6 rats in one group. 7 days after the administration, a toxicity test was carried out.

As a result, it was found that the rats did not die even when the compound was administered at a dose of 10 mg/kg. Moreover, no abnormality was found by a post-mortem examination. Therefore, the $LD_{50}$ value is 10 mg/kg or more.

Industrial Applicability

The medicine of the present invention has extremely excellent cell-proliferation-accelerating effect, radioprotec-

49 tive effect, blood-platelet-increasing effect, and blood-platelet-decrease-inhibitory effect. It is therefore useful for accelerating marrow cell proliferation, for protecting human against radiation damage, and for the treatment of thrombocytopenia.

What is claimed is:

1. A method for treatment of damage to bone marrow caused by radiation said radiation being gamma-ray or X-ray comprising administering to a human in need of such treatment an effctive amount of an α-galactosylceramide selected from the group consisting of the following compounds:

(1) (2S,3R)-1-(α-D-galactopyransyloxy)-2-tetracosanoylamino-3-octadecanol, (2) (2S,3R)-2-docosanoylamino-1-(α-D-galactopyranosyloxy)-3-ectadecanol, (3) (2S,3R)-1-(α-D-galactopyranosyloxy)-2-icosanoylamino-3-octadecanol, (4) (2S,3R)-1-(α-D-galactopyranosyloxy)-2-octadecanoylamino-3-octadecanol, (5) (2S,3R)-1-(α-D-galactopyranosyloxy)-2-tetradecanoylamino-3-octadecanol, (6) (2S,3R)-1-(α-D-galactopyranosyloxy)-2-octanoylamino-3-octadecanol, (7) (2S3R)-1-(α-D-galactopyrarosyloxy)-2-tetracosanoylamino-3-tetradecanole (8) (2S3R)-1-(α-D-galactopyranosyloxy)-2-tetradecanoylamino-3-hexadecanol, (9) (2S,3R)-1-(α-D-galactopyranosyloxy)-2-[(R)-2-hydroxy-tetracosanoylamino]-3-octadecanol,

(10) (2S,3S4R)-1-(α-D-galactopyranosyloxy(-2-tetracosanoyl-amino-3,4-octadecanediol,

(11) (2S,3S,4R)-1-(α-D-galactopyranosyloxy)-2-tetracosanoyl-amino-3,4-heptadecanediol,

(12) (2S,3S,4R)-1-(α-D-galactopyranosyloxy)-2-tetracosanoyl-amino-3,4-pentadecanediol,

(13) (2S,3S,4R)-1-(α-D-galactopyranosyloxy)-2-tetracosanoyl-amino-3,4-undecanediol, (14). (2S,3S4R)-1-(α-D-galactopyranosyloxy)-2-hexacosanoyl-amino-3,4-heptadecanediol,

(15) (2S,3S4R)-1-(α-D-galactopyranosyloxy)-2-[(R)-2-hydroxy-tetracosanoylamino]-3,4-octadecanediol,

(16) (2S,3S,4R)-1-(α-D-galactopyranosyloxy)-2-[(R)-2-hydroxy-tetracosanoylamino]-3,4-heptadecanediol,

(17) (2S,3S,4R)-1-(α-D-galactopyranosyloxy)-2-[(R)-2-hydroxy-tetracosanoylamino]-3,4-pentadecanediol,

(18) (2S,3S,4R)-1-(α-D-galactopyranosyloxy)-2-[(R)-2-hydroxy-tetracosanoylamino]-3,4-undecanediol,

(19) (2S,3S,4R)-1-(α-D-galactopyranosyloxy)-2-[(R)-2-hydroxy-hexacosanoylamino]-3,4-octadecanediol,

(20) (2S,3S,4R)-1-(α-D-galactopyranosyloxy)-2-[(R)-2-hydroxy-hexacosanoylamino]-3,4-nonadecanediol,

(21) (2S,3S,4R)-1-(α-D-galactopyranosyloxy)-2-[(R)-2-hydroxy-hexacosanoylamino]3-3,4-icosanediol,

(22) (2,S,3S,4R)-1-(α-D-galactopyranosyloxy)-2-[(S)-2-hydroxy-tetracosanoylamino]-3,4-haptadecanediol,

(23) (2S,3S,4R)-1-(α-D-galactopyranosyloxy)-2-[(S)-2-hydroxy-tetracosanoylamino]-16-methyl-3,4-heptadecanediol,

(24) (2S,3S,4R)-1-(α-D-galactopyranosyloxy)-16-methyl-2-tetracosanoylamino-3,4-heptadecanediol,

(25) (2S,3R)-1-(α-D-galactopyranosyloxy)-2-oleoylamino-3-octadecanol,

50

(26) (2S,3S,4R)-1-(α-D-galactopyranosyloxy)-2-hexacosanoyl-amino-3,4-octadecanediol, and

(27) (2S,3S,4R)-1-(α-D-galactopyranosyloxy)-2-octacosanoyl-amino-3,4-haptadecanediol.

2. A method according to claim 1 wherim the α-galactosylceramide is selected from the group consisting of the following compounds:

(1) (2S,3S,4R)-17-(α-D-galactopyranosyloxy)-2-tetracosanoyl-amino-3,4-octadecanediol, (2) (2S,3S,4R) -1-(α-D-galactopyranosyloxy)-2-tetracosanoyl-amino-3,4-heptadecanediol, (3) (2S,3S,4R)-1-(α-D-galactopyranosyloxy)-2-tetracosanoyl-amino-3,4-pentadecanediol, (4) (2S,3S,4R)-1-(α-D-galactopyranosyloxy)-2-tetracosanoyl-amino-3,4-undecanediol, (5) (2S,3S,4R)-1-(α-D-galactopyranosyloxy)-2-hexacosanoyl-amino-3,4-heptadecanediol, (6) (2S,3S,4R)-1-(α-D-galactopyranosyloxy)-2-hexacosanoyl-amino-3,4-octadecanediol, and (7) (2S,3S,4R)-1-(α-D-galactopyranosyloxy)-2-octacosanoyl-amino-3,4-heptadecanediol.

3. A method according to claim 2 wherein α-galactosylceramide is (2S,3S,4R)-1-(α-galactopyransyloxy)-2-hexacosanoylamino-3,4-octadecanediol.

4. A method according to claim 1 wherein the radiation is X-ray.

5. A method according to claim 2 wherein the radiation is X-ray.

6. A method according to claim 3 wherein the radiation is X-ray.

7. A method for treatment of damage to bone marrow caused by radiation said radiation being gamma-ray or X-ray comprising administering to a human in need of such treatment an effective amount of an α-galactosylceramide represented by the following formula (II):

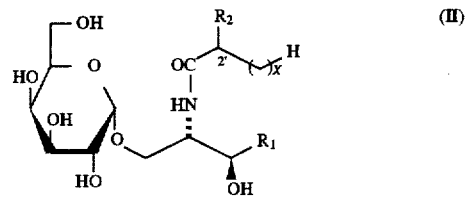

wherein $R_1$ represents —CH(OH)(CH$_2$)$_Y$CH$_3$ or —CH(OH)(CH$_2$)$_Y$CH(CH$_3$)$_2$; $R_2$ represents H or OH; X is an integer of 18 to 26 and Y is an integer of 5 to 17 with the proviso that when $R_1$ represents —CH(OH)(CH$_2$)$_Y$CH$_3$, and $R_2$ is H, X is an integer of 18 to 26 and Y is an integer of 5 to 15; when $R_1$ represents —CH(OH)(CH$_2$)$_Y$CH$_3$ $R_2$ is OH, X is an integer of 18 to 26 and Y is an integer of 5 to 17; or when $R_1$ represents —CH(OH)(CH$_2$)$_Y$CH(CH$_3$)$_2$, $R_2$ is H, X is an integer of 20 to 24 and Y is an integer of 9 to 13.

8. A method for treatment of damage to bone marrow caused by radiation said radiation being gamma-ray or X-ray comprising administering to a human in need of such an effective amount of an α-galactosylceramide represented by the following formula (VII);

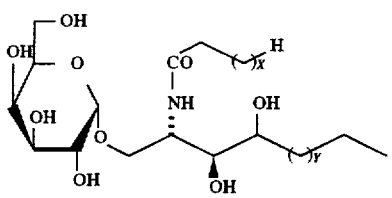

wherein X is an integer of 18 to 26, and Y is an integer of 5 to 15.

9. A method according to claim 8, wherein X in the formula (VII) is an integer of 21 to 25 and Y in the formula (VII) is an integer of 6 to 14.

10. A method for treatment of damage to bone marrow caused by radiation said radiation being gamma-ray or X-ray comprising administering to a human in need of such treatment an effective amount of an α-galactosylceramide represented by the following formula (VIII):

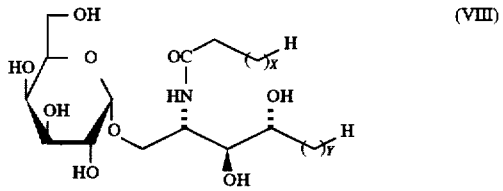

(VIII)

wherein X is an integer of 18 to 26, and Y is an integer of 5 to 15.

11. A method according to claim 10, wherein X in the formula (VIII) is an integer of 21 to 25 and Y in the formula (VIII) is an integer of 6 to 14.

12. A method for treatment of damage to bone marrow caused by radiation said radiation being gamma-ray or X-ray comrising administering to a human in need of such an effective amount of an α-galactosylceramide represented by the following formula (IX):

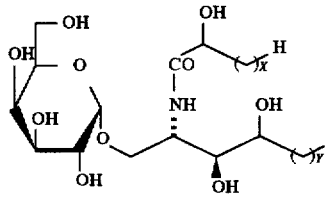

wherein X is an integer of 18 to 26, and Y is an integer of 5 to 17.

13. A method for treatment of damage to bone marrow caused by radiation said radiation being gamm-ray or X-ray comprising administering to a human in need of such an effective amount of an α-galactosylceramide represented by the following formula (XI):

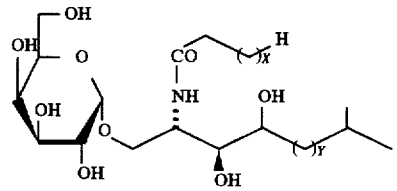

wherein X is an integer of 20 to 24, and Y is an integer of 9 to 13.

14. A method for treatment of damage to bone marrow caused by radiation said radiation being gamma-ray or X-ray comprising administering to a human in need of such an effective amount of an α-galactosylceramide represented by the following formula (XIII):

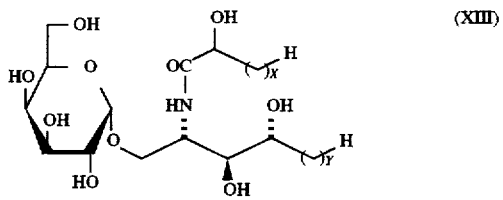

(XIII)

wherein X is an integer of 20 to 24, and Y is an integer of 9 to 13.

15. A method according to claim 7 wherein the radiation is X-ray.

16. A method according to claim 8 wherein the radiation is X-ray.

17. A method according to claim 9 wherein the radiation ix X-ray.

18. A method according to claim 10 wherein the radiation is X-ray.

19. A method according to claim 11 wherein the radiation is X-ray.

20. A method according to claim 12 wherein the radiation is X-ray.

21. A method according to claim 13 wherein the radiation is X-ray.

22. A method according to claim 14 wherein the radiation is X-ray.

* * * * *